United States Patent
Lu et al.

(10) Patent No.: US 10,980,835 B2
(45) Date of Patent: *Apr. 20, 2021

(54) ARSENIC TRIOXIDE FOR TREATMENT OF PIN1-ASSOCIATED DISORDERS

(71) Applicant: Beth Israel Deaconess Medical Center, Inc., Boston, MA (US)

(72) Inventors: Kun Ping Lu, Newton, MA (US); Xiao Zhen Zhou, Newton, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/829,467

(22) Filed: Dec. 1, 2017

(65) Prior Publication Data

US 2018/0153934 A1 Jun. 7, 2018

Related U.S. Application Data

(60) Provisional application No. 62/429,588, filed on Dec. 2, 2016.

(51) Int. Cl.
| | | |
|---|---|---|
| *A61K 33/36* | (2006.01) | |
| *A61P 35/00* | (2006.01) | |
| *A61P 19/02* | (2006.01) | |
| *A61K 31/203* | (2006.01) | |
| *A61P 29/00* | (2006.01) | |
| *A61K 9/00* | (2006.01) | |

(52) U.S. Cl.
CPC ............ *A61K 33/36* (2013.01); *A61K 9/0002* (2013.01); *A61K 31/203* (2013.01); *A61P 19/02* (2018.01); *A61P 29/00* (2018.01); *A61P 35/00* (2018.01)

(58) Field of Classification Search
None
See application file for complete search history.

(56) References Cited

U.S. PATENT DOCUMENTS

| 9,439,884 | B2 * | 9/2016 | Lu | ........................ A61K 31/203 |
| 9,968,579 | B2 * | 5/2018 | Lu | ........................ A61K 31/203 |
| 10,265,288 | B2 * | 4/2019 | Lu | ........................ A61K 45/06 |
| 10,351,914 | B2 * | 7/2019 | Lu | |
| 2014/0086909 | A1 * | 3/2014 | Lu | ........................ A61K 45/06 424/133.1 |
| 2014/0219957 | A1 * | 8/2014 | Lu | ........................ A61K 31/203 424/85.4 |
| 2015/0044278 | A1 * | 2/2015 | Lu | ........................ A61K 45/06 424/450 |
| 2015/0218195 | A1 * | 8/2015 | Miodragovic | ........ C07F 19/005 514/504 |
| 2016/0022674 | A1 * | 1/2016 | Steggerda | ........... A61K 31/7068 514/248 |

FOREIGN PATENT DOCUMENTS

WO WO 2016/011265 * 1/2016

OTHER PUBLICATIONS

Mehmeti et al. Breast Cancer Research vol. 17:130. (Year: 2015).*
Wei et al. Nature Medicine vol. 21, No. 5. (Year: 2015).*
Lin et al. World J. Gasteroenterol, vol. 11, No. 36, pp. 5633-5637. (Year: 2005).*
Cicconi and Lo-Coco. Annals of Oncology, vol. 27, No. 8, pp. 1474-1481. (Year: 2016).*
Deng et al. Cell Cycle, vol. 11, No. 2, pp. 367-376. (Year: 2012).*
Zannini et al. Frontiers in Oncology vol. 9, Article 94. (Year: 2019).*
Frith, "Arsenic—the 'Poison of Kings' and the 'Saviour of Syphilis'", Journal of Military and Veterans' Health. 21(4):11-7 (2013).
Waxman et al., "History of the development of arsenic derivatives in cancer therapy," Oncologist. 6(Suppl 2):3-10 (2001).

* cited by examiner

*Primary Examiner* — Katherine Peebles
(74) *Attorney, Agent, or Firm* — Goodwin Procter LLP

(57) ABSTRACT

The present invention relates to the treatment of Pin1-associated disorders (e.g., disorders characterized by elevated Pin1 activity) with arsenic trioxide, optionally in combination with a retinoic acid compound. Pin1-associated disorders may include, for example, proliferative disorders (e.g., cancers), inflammatory conditions, and autoimmune disorders associated with aberrant levels of Pin1 activity.

1 Claim, 22 Drawing Sheets
(7 of 22 Drawing Sheet(s) Filed in Color)

Fig. 2A-C

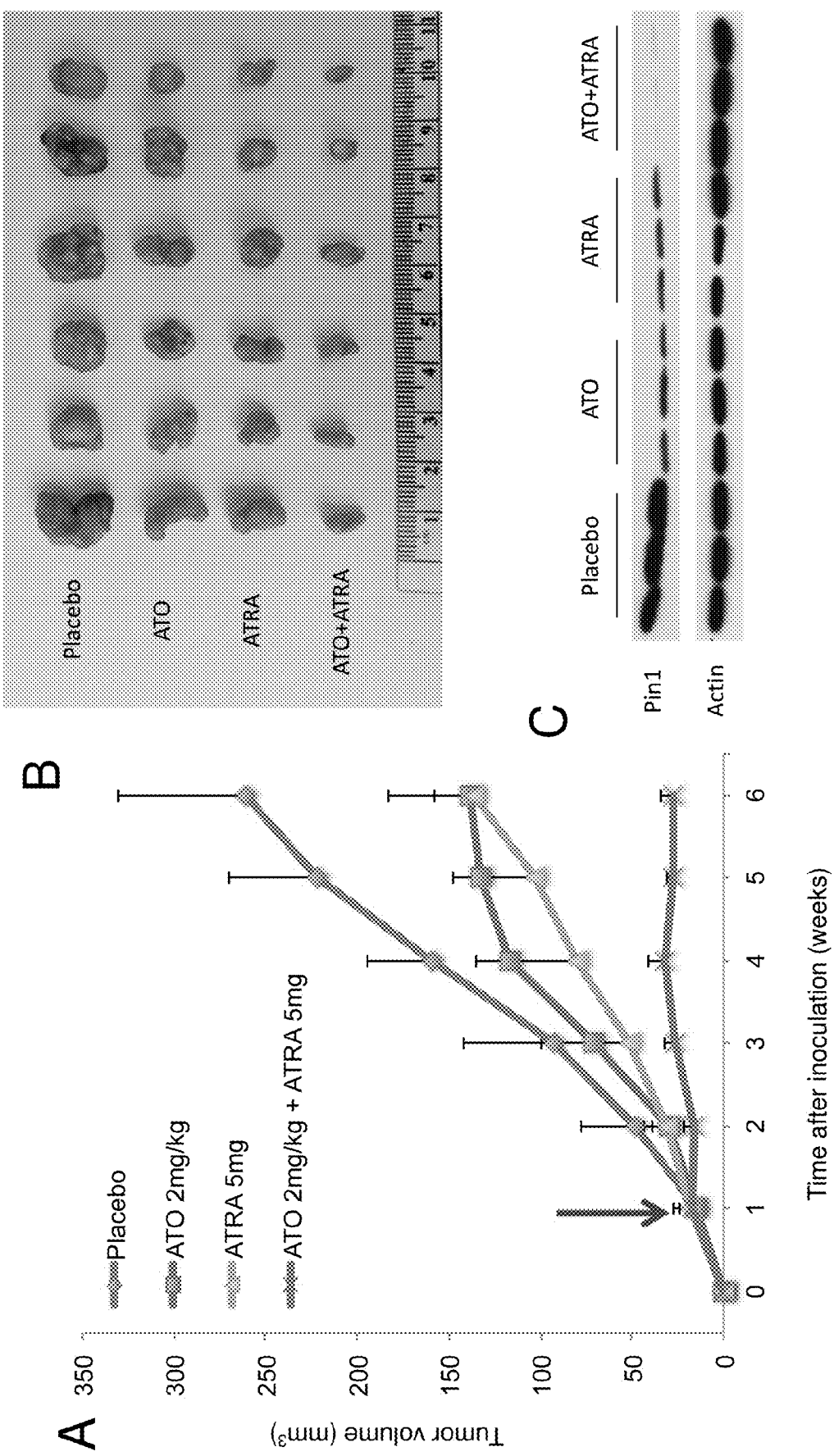
Fig. 13A-C

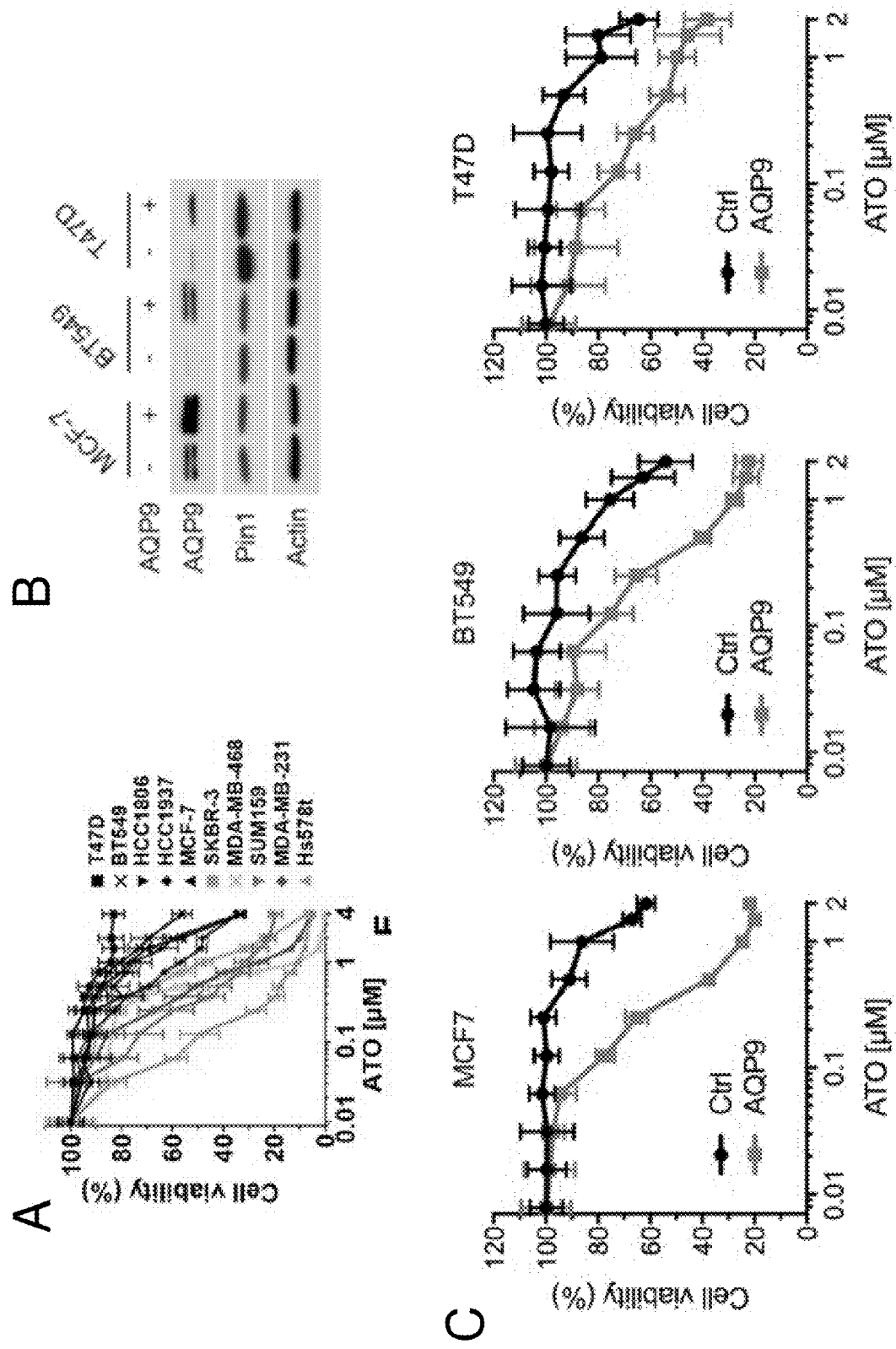
Fig. 14A-C

Fig. 15A-B
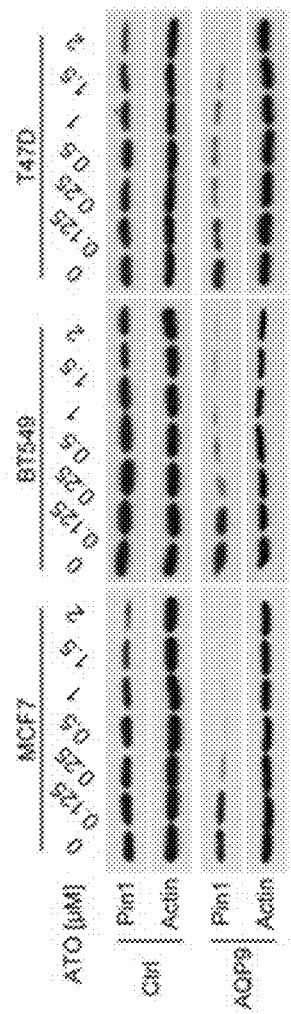
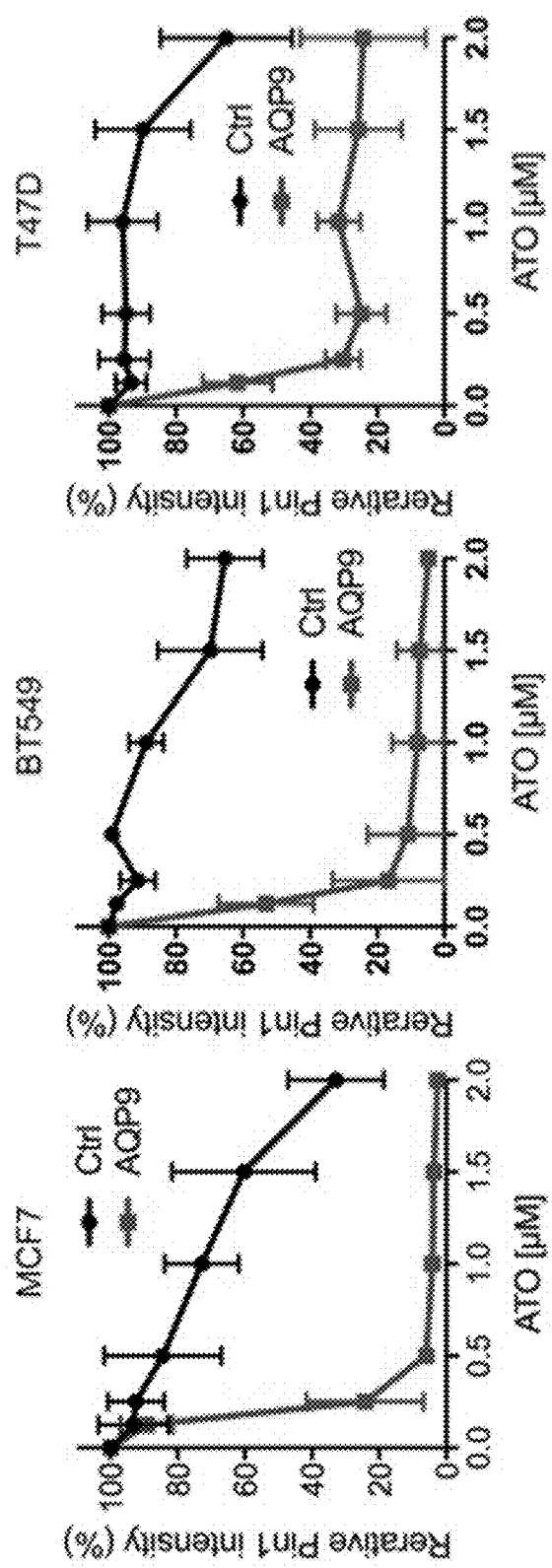

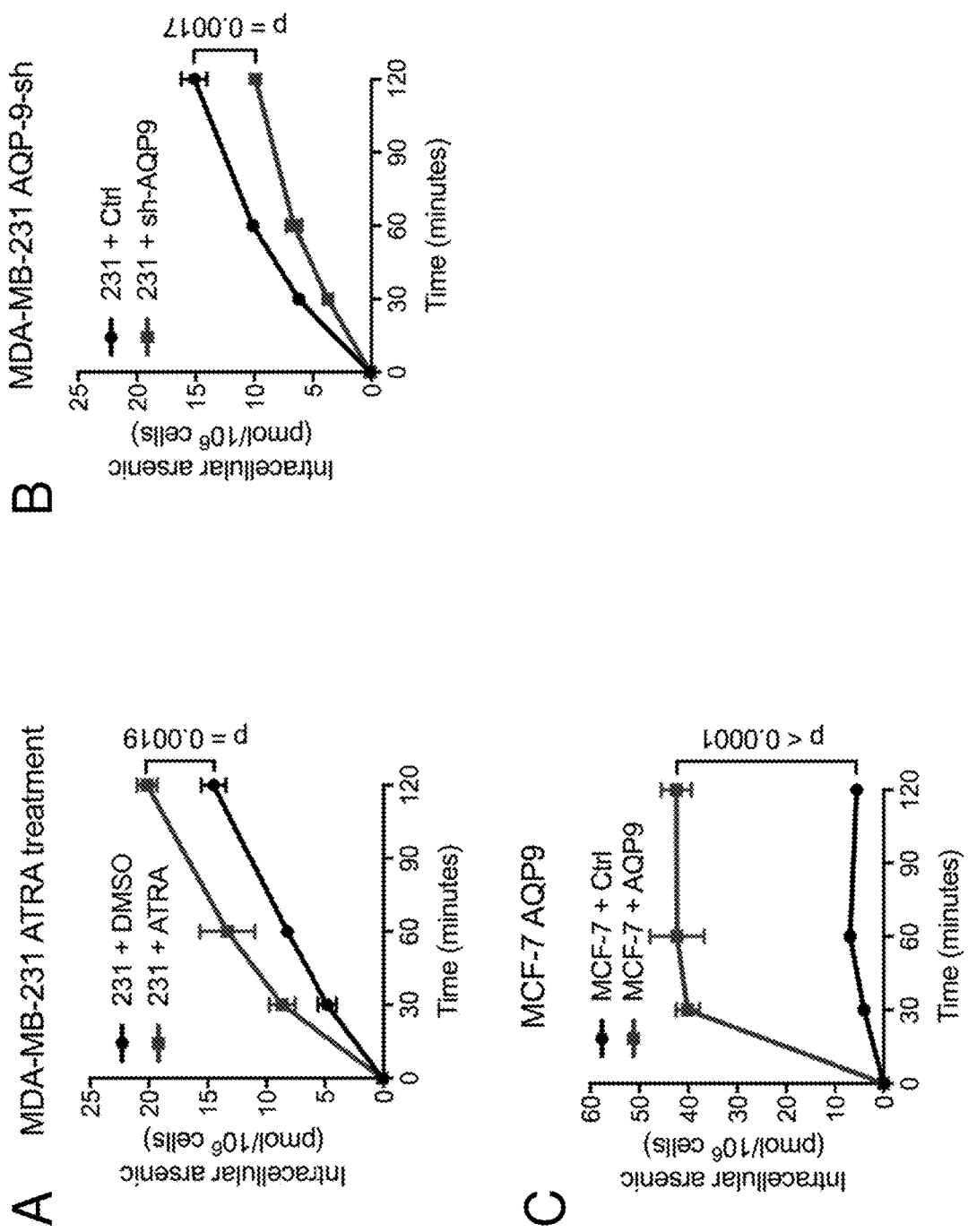
Fig. 16A-C

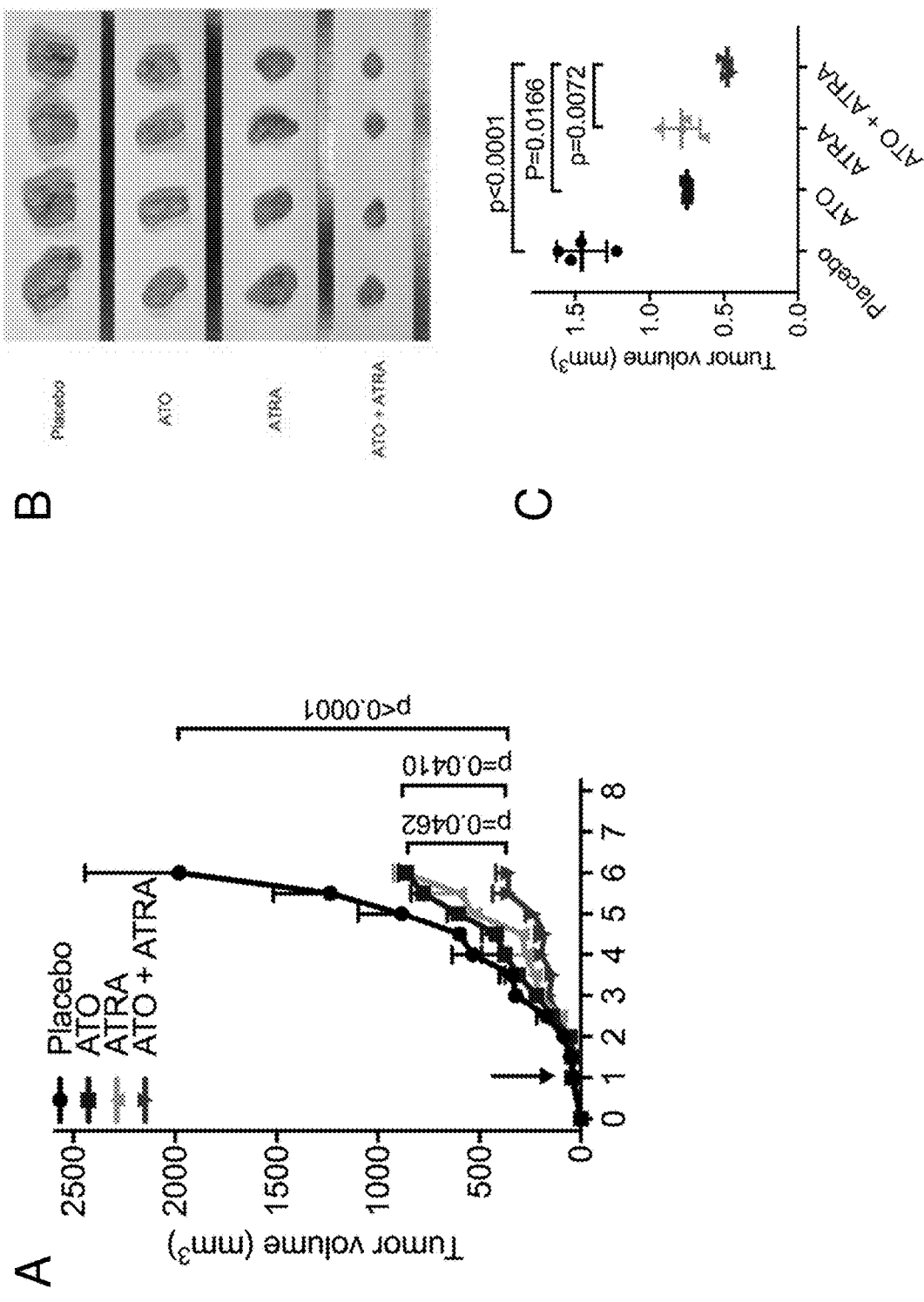
Fig. 17A-C

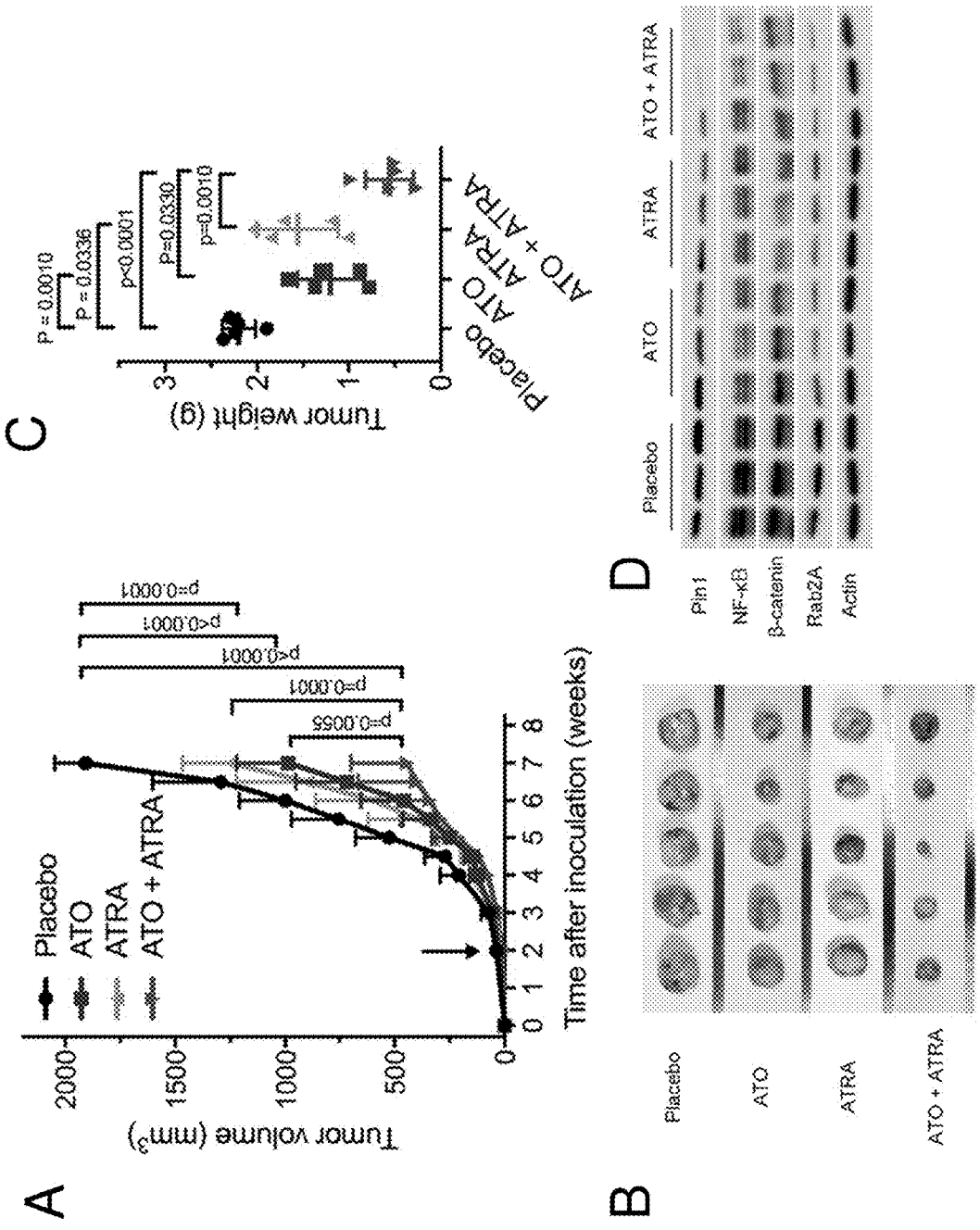
Fig. 18A-D

Fig. 19A-C
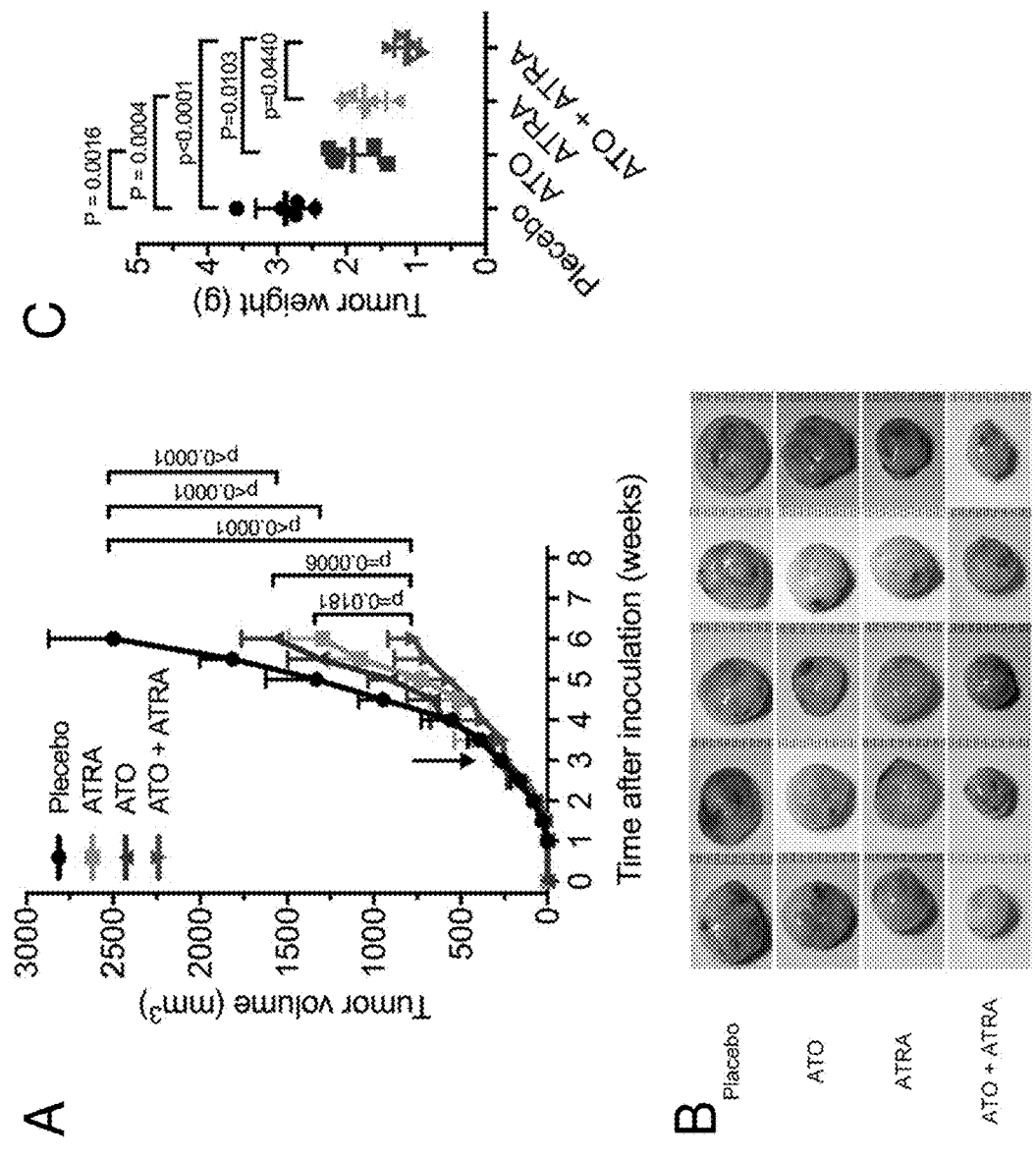

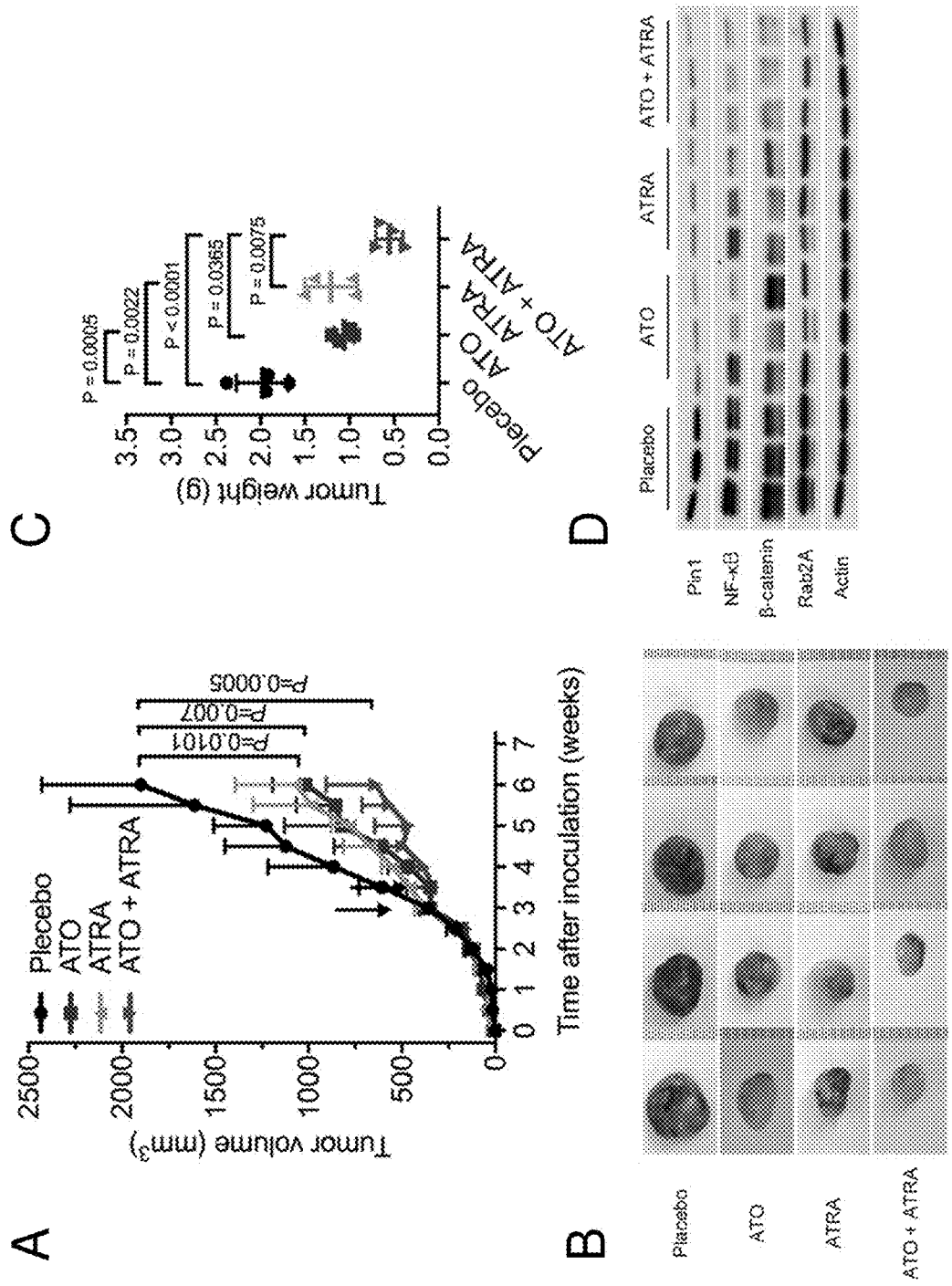
Fig. 20A-D

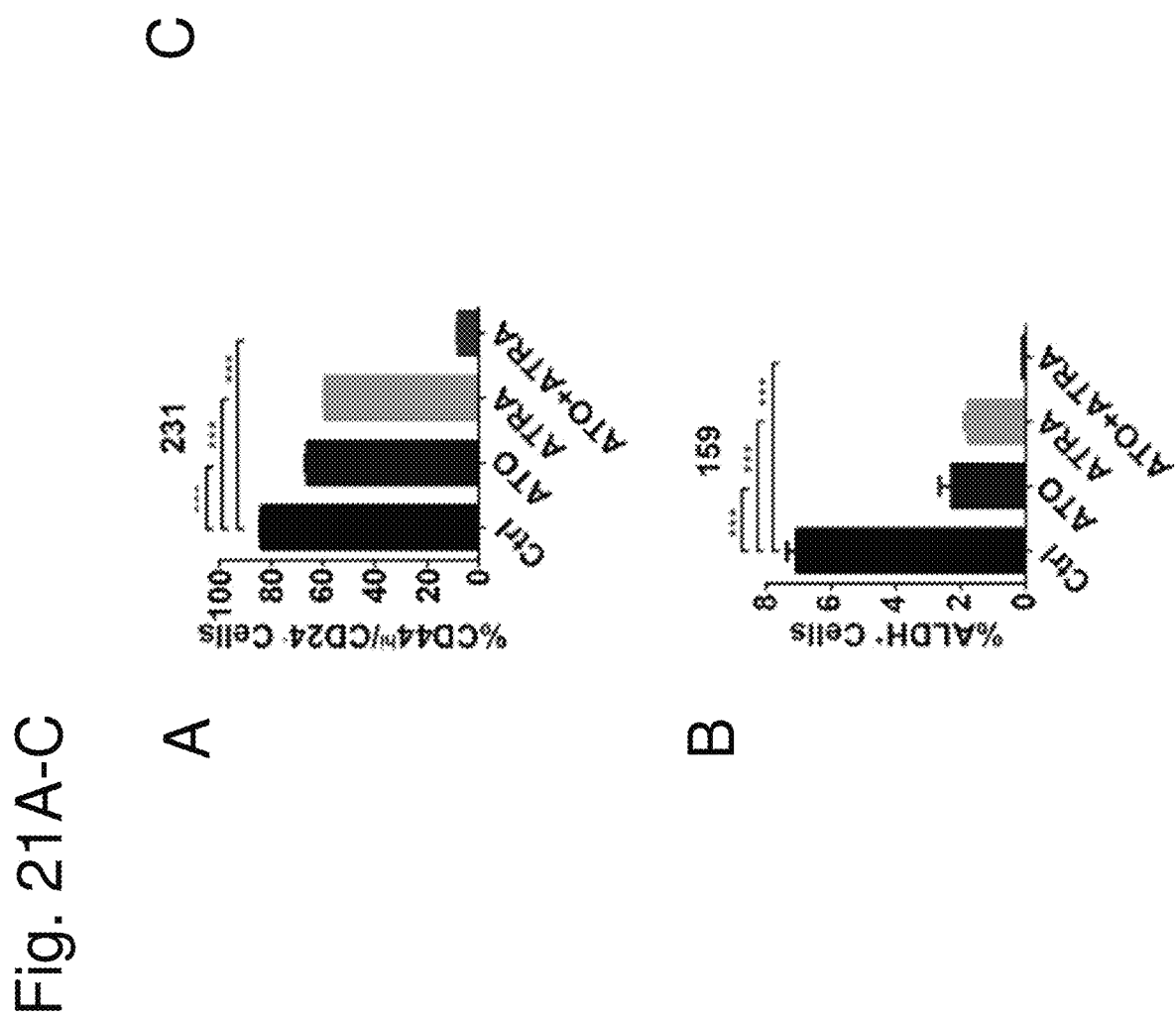
Fig. 21A-C

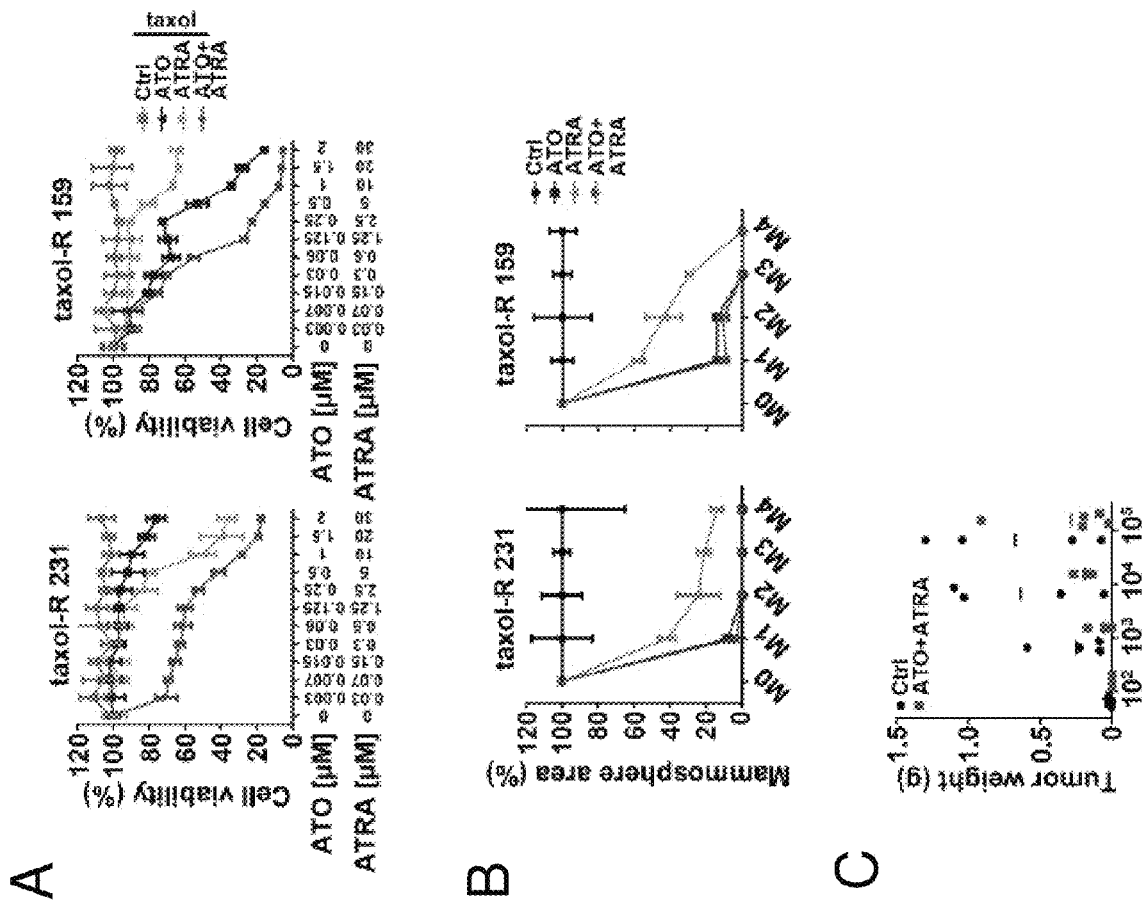
Fig. 22A-C

US 10,980,835 B2

ARSENIC TRIOXIDE FOR TREATMENT OF PIN1-ASSOCIATED DISORDERS

STATEMENT AS TO FEDERALLY FUNDED RESEARCH

This invention was made with government support under Grant No. CA167677 and HL111430 awarded by the National Institutes of Health. The government has certain rights in the invention.

BACKGROUND

Phosphorylation on serine/threonine-proline motifs restrains cis/trans prolyl isomerization, and also creates a binding site for the essential protein Pin1. Pin1 binds and regulates the activity of a defined subset of phosphoproteins, as well as participating in the timing of mitotic progression. Both structural and functional analyses have indicated that Pin1 contains a phosphoserine/threonine-binding module that binds phosphoproteins, and a catalytic activity that specifically isomerizes the phosphorylated phosphoserine/threonine-proline. Both of these Pin1 activities are essential for Pin1 to carry out its function in vivo.

Pin1 is highly conserved and contains a protein-interacting module, called WW domain, and a catalytically active peptidyl-prolyl isomerase (PPIase). Pin1 is structurally and functionally distinct from members of two other well-characterized families of PPIases, the cyclophilins and the FKBPs. PPIases are ubiquitous enzymes that catalyze the typically slow prolyl isomerization of proteins, allowing relaxation of local energetically unfavorable conformational states. Phosphorylation on Ser/Thr residues immediately preceding Pro not only alters the prolyl isomerization rate, but also creates a binding site for the WW domain of Pin1. The WW domain acts a novel phosphoserine-binding module targeting Pin1 to a highly conserved subset of phosphoproteins. Furthermore, Pin1 displays a unique phosphorylation-dependent PPIase that specifically isomerizes phosphorylated Ser/Thr-Pro bonds and regulates the function of phosphoproteins.

Pin1-catalyzed cis-trans isomerization of phosphorylated Ser/Thr-Pro motifs has been shown to be involved in an increasing number of diseases. For example, Pin1 is overexpressed and/or overactivated in numerous cancers and elevated Pin1 can be correlated with poor clinical prognosis. Pin1 polymorphisms that lower Pin1 expression are associated with reduced risk for multiple cancers. Moreover, Pin1-null mice are highly resistant to tumorigenesis even after overexpression of an oncogene such as HER2, RAS, Myc, Notch3, mutant p53, or deletion of a tumor suppressor such as p53. Conversely, Pin1 overexpression has been shown to disrupt cell cycle coordination and lead to chromosome instability and tumorigenesis. Pin1 activates over 40 oncogenes and inactivates over 20 tumor suppressors, many of which have a major role in cancer stem cells (CSCs). For example, it has been shown that Pin1 is fundamental for driving CSC expansion, tumorigenesis, and metastasis. Thus, Pin1 inhibitors may have the desirable ability to simultaneously block multiple cancer-driving pathways in CSCs and non-CSC tumor cells for treating aggressive cancer and overcoming drug resistance, with limited toxicity. As such, there exists a need in the art for new and improved Pin1 inhibitors.

SUMMARY OF THE INVENTION

The present invention provides methods of treating cellular phenotypes associated with elevated Pin1 activity using an arsenic trioxide compound. Contacting a cell exhibiting elevated Pin1 activity with arsenic trioxide may result in a decrease in Pin1 activity in the cell. The cell may be present within a subject. In some embodiments, the subject is administered arsenic trioxide to reduce Pin1 activity in the subject. Such reduction of Pin1 activity may result in treatment of a Pin1-associated disorder in the subject. In addition, the invention features administration of arsenic trioxide in combination with a retinoic acid compound. Such a combination of arsenic trioxide and a retinoic acid compound may synergistically reduce Pin1 activity. Also provided are methods for reducing Pin1 activity in one or more cells by contacting the cells with arsenic trioxide and/or a retinoic acid compound.

In some aspects, the invention features a method of inhibiting, reducing, or reversing a phenotype associated with elevated Pin1 activity in a cell. This method includes administering an effective amount of arsenic trioxide to a cell having elevated levels of Pin1 activity, wherein the elevated levels of Pin1 activity indicates that the cell is susceptible to inhibition of the phenotype upon administration of arsenic trioxide.

In some embodiments, the phenotype associated with elevated levels of Pin1 activity in a cell includes increased cell death, an oncogenic transformation, and/or an autoimmune phenotype (e.g., overproduction of cytokines and/or the overproduction of autoantibodies).

In some embodiments the cell is an oncogenic transformed cell or an autoimmune cell. In some embodiments, the cell is an oncogenic transformed cell and the cell becomes a non-transformed (e.g., not oncogenic) cell upon administration of the arsenic trioxide.

In some aspects, the invention features a method for reducing Pin1 activity in a cell (e.g., reducing Pin1 activity by at least about 1%, 2%, 3%, 4%, 5%, 6%, 7%, 8%, 9%, 10%, 15%, 20%, 25%, 30%, 40%, 50%, 60%, 70%, 80%, 90%, 100%, 200%, 500%, 1000%, or greater). This method may include administering arsenic trioxide to a cell in an amount sufficient to increase degradation of Pin1 in the cell (e.g., increase Pin1 degradation by at least about 1%, 2%, 3%, 4%, 5%, 6%, 7%, 8%, 9%, 10%, 15%, 20%, 25%, 30%, 40%, 50%, 60%, 70%, 80%, 90%, 100%, 200%, 500%, 1000%, or greater).

In some embodiments of any of the foregoing aspects, the method further includes administering an effective amount of a retinoic acid compound to the cell. The retinoic acid compound and the arsenic trioxide may operate synergistically to reduce Pin1 activity in the cell. Administration of arsenic trioxide and a retinoic acid compound may be more effective for reducing Pin1 activity in the cell than administration of the same quantities of either the arsenic trioxide or the retinoic acid compound alone.

In some embodiments of any of the foregoing aspects, arsenic trioxide and the retinoic acid compound may be administered concurrently (e.g., within about 1 min, 2 min, 5 min, 10 min, 20 min, 30 min, or 60 min) or separately. The arsenic trioxide may be administered either prior to or after the retinoic acid compound.

In some embodiments of any of the foregoing aspects, the retinoic acid compound is all-trans retinoic acid (ATRA), 13-cis-retinoic acid, retinol, retinyl acetate, retinal, or AC-55640, or is a compound structurally similar to retinoic acid.

In some embodiments, the retinoic acid compound is a Table 1 Compound. By "Table 1 Compound" is meant any of the compounds listed in Table 1, or any compound falling within the corresponding generic formula as set forth below.

TABLE 1

Additional retinoic acid compounds

| No. | STRUCTURE | Formula |
|---|---|---|
| 1 | 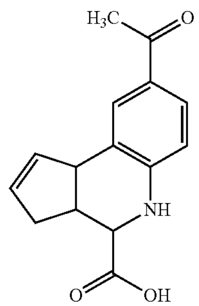 [SMILES: CC(=O)c1ccc2c(c1)C1C=CCC1C(C(=O)O)N2] | (I) |
| 2 | 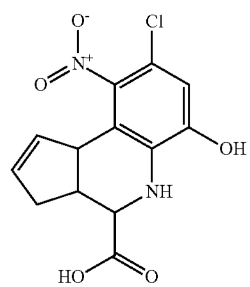 [SMILES: O=C(O)C1Nc2c(O)cc(Cl)c([N+](=O)[O-])c2C2C=CCC12] | (I) |
| 3 | 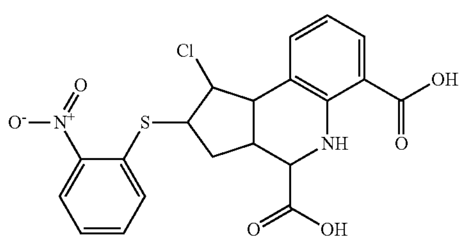 [SMILES: O=C(O)c1cccc2c1NC(C(=O)O)C1CC(Sc3ccccc3[N+](=O)[O-])C(Cl)C21] | (I) |
| 4 | 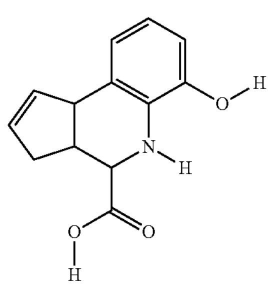 [SMILES: O=C(O)C1Nc2c(O)cccc2C2C=CCC12] | (I) |
| 5 | 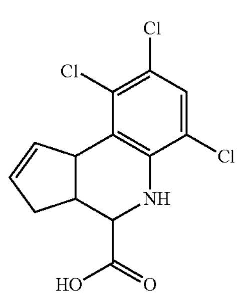 [SMILES: O=C(O)C1Nc2c(Cl)cc(Cl)c(Cl)c2C2C=CCC12] | (I) |

TABLE 1-continued
Additional retinoic acid compounds
| No. | STRUCTURE | Formula |
|---|---|---|
| 6 | 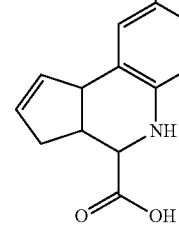 | (I) |
| 7 | 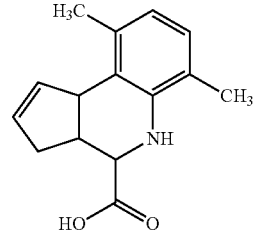 [SMILES: Cc1ccc(C)c2c1NC(C(=O)O)C1CC=CC21] | (I) |
| 8 | 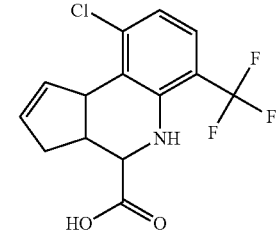 [SMILES: O=C(O)C1Nc2c(C(F)(F)F)ccc(Cl)c2C2C=CCC12] | (I) |
| 9 | 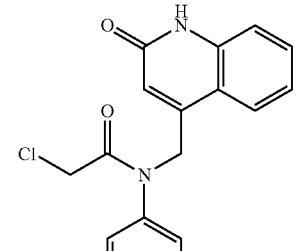 | (II) |
| 10 | 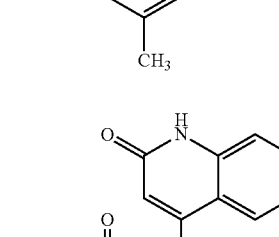 | (II) |

TABLE 1-continued

Additional retinoic acid compounds

| No. | STRUCTURE | Formula |
|---|---|---|
| 11 | 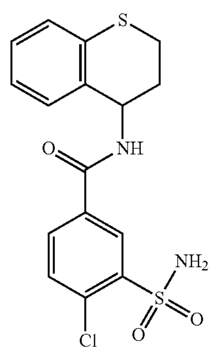 [SMILES: NS(=O)(=O)c1cc(C(=O)NC2CCSc3ccccc32)ccc1Cl] | |
| 12 | 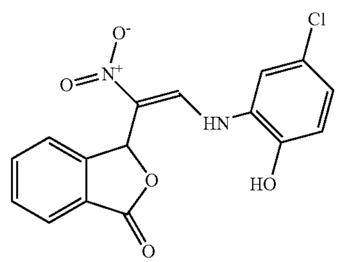 [SMILES: O=C1OC(/C(=C\Nc2cc(Cl)ccc2O)[N+](=O)[O-])c2ccccc21] | |
| 13 | 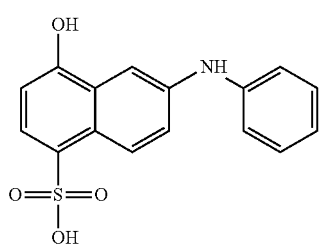 [SMILES: O=S(=O)(O)c1ccc(O)c2cc(Nc3ccccc3)ccc12] | (III) |
| 14 | 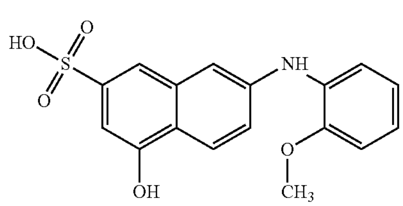 [SMILES: COc1ccccc1Nc1ccc2c(O)cc(S(=O)(=O)O)cc2c1] | (III) |
| 15 | 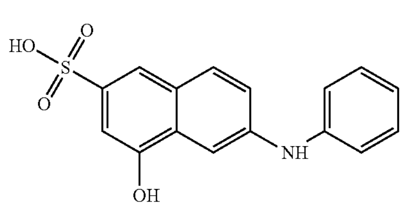 [SMILES: O=S(=O)(O)c1cc(O)c2cc(Nc3ccccc3)ccc2c1] | (III) |

TABLE 1-continued
Additional retinoic acid compounds
| No. | STRUCTURE | Formula |
|---|---|---|
| 16 | 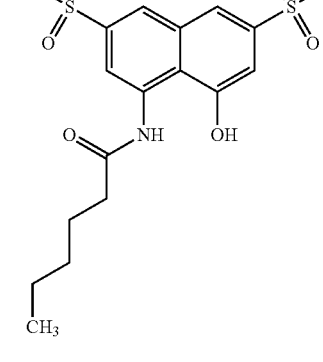 | |
| 17 | 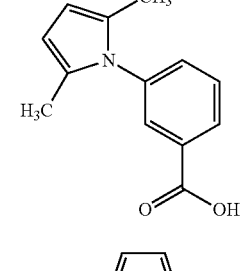 | (IV) |
| 18 | 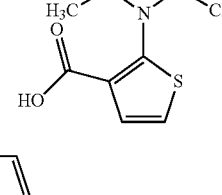 | (IV) |
| 19 | 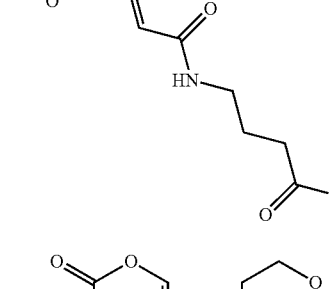 | |
| 20 | 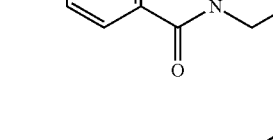 | |
| 21 | 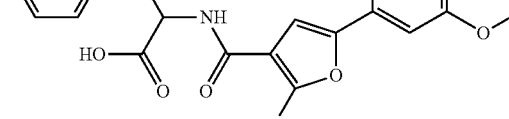 | |

TABLE 1-continued

Additional retinoic acid compounds

| No. | STRUCTURE | Formula |
|---|---|---|
| 22 | 7-nitro-1H-indole-2-carboxylic acid | |
| 23 | 2-(4-hydroxy-1H-indol-3-yl)acetic acid | |
| 24 | N-(4-(3-chlorothiophen-2-yl)thiazol-2-yl)-2,5-dichlorobenzenesulfonamide | |
| 25 | 2-(N-methyl-3-(1H-pyrrol-1-yl)benzamido)-N-(p-tolyl)acetamide | |
| 26 | 2-(N-methyl-5,6-dihydro-4H-cyclopenta[b]thiophene-2-carboxamido)-N-(4-methoxyphenyl)acetamide | |

TABLE 1-continued

Additional retinoic acid compounds

| No. | STRUCTURE | Formula |
|---|---|---|
| 27 | 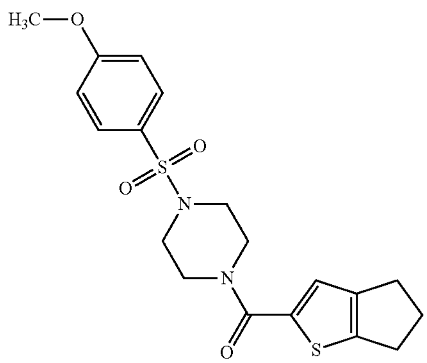 [SMILES: COc1ccc(S(=O)(=O)N2CCN(C(=O)c3cc4c(s3)CCC4)CC2)cc1] | |
| 28 | 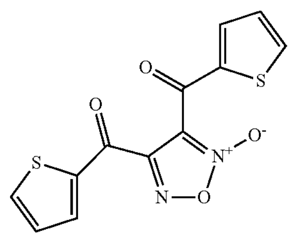 [SMILES: O=C(c1cccs1)c1no[n+]([O-])c1C(=O)c1cccs1] | (V) |
| 29 | 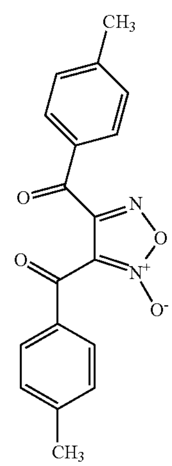 [SMILES: Cc1ccc(C(=O)c2no[n+]([O-])c2C(=O)c2ccc(C)cc2)cc1] | (V) |
| 30 | 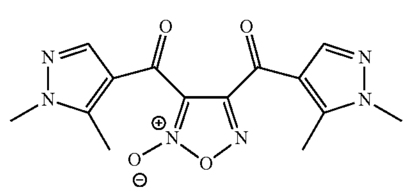 | (V) |
| 31 | 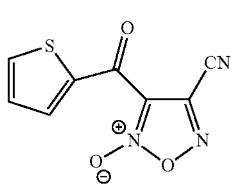 [SMILES: N#Cc1no[n+]([O-])c1C(=O)c1cccs1] | (V) |

TABLE 1-continued
| | Additional retinoic acid compounds | |
|---|---|---|
| No. | STRUCTURE | Formula |
| 32 | 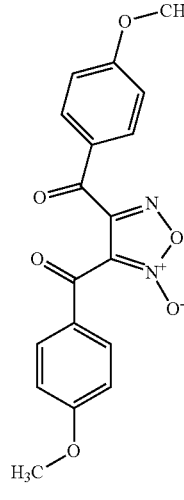 | (V) |
| 33 | 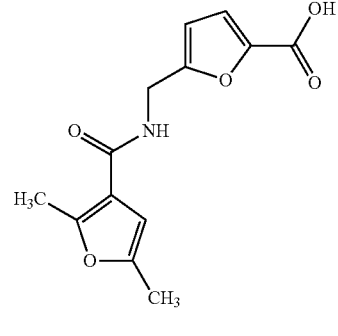 [SMILES: Cc1cc(C(=O)NCc2ccc(C(=O)O)o2)c(C)o1] | |
| 34 | 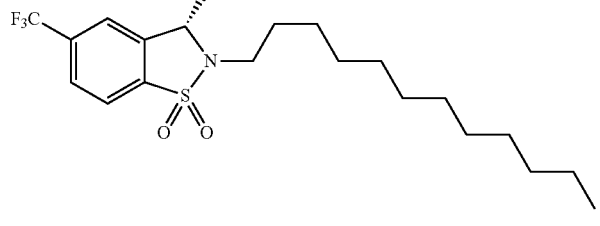 | |
| 35 | 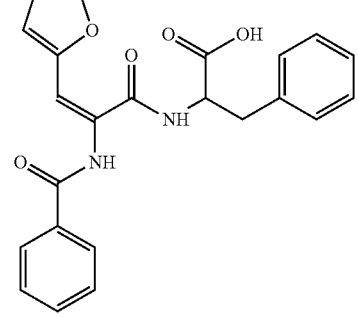 | |

TABLE 1-continued
Additional retinoic acid compounds
| No. | STRUCTURE | Formula |
|---|---|---|
| 36 | 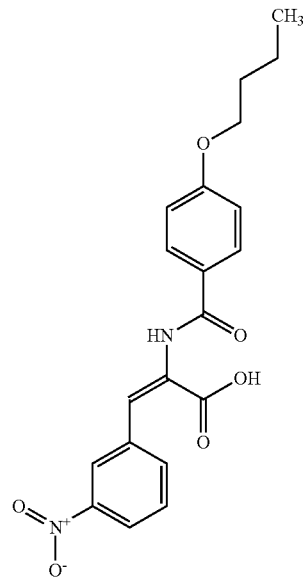 [SMILES: CCCCOc1ccc(C(=O)N/C(=C/c2cccc([N+](=O)[O-])c2)C(=O)O)cc1] | |
| 37 | 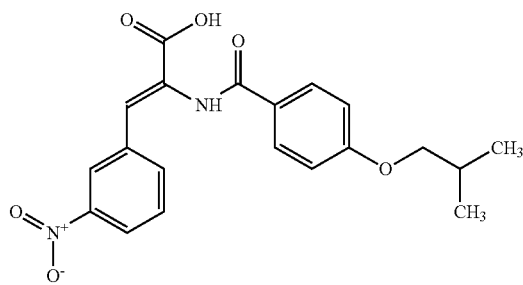 [SMILES: CC(C)COc1ccc(C(=O)N/C(=C\c2cccc([N+](=O)[O-])c2)C(=O)O)cc1] | |
| 38 | 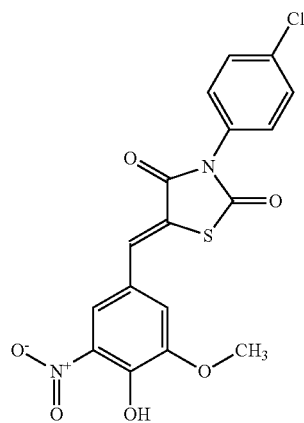 [SMILES: COc1cc(/C=C2\SC(=O)N(c3ccc(Cl)cc3)C2=O)cc([N+](=O)[O-])c1O] | |

TABLE 1-continued
Additional retinoic acid compounds
| No. | STRUCTURE | Formula |
|-----|-----------|---------|
| 39 | 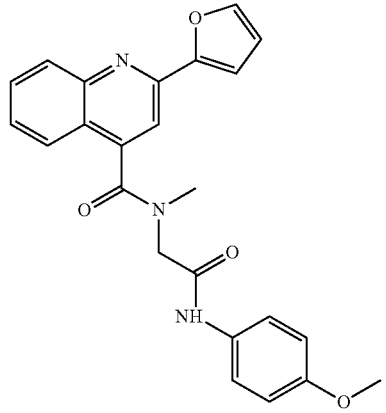 [SMILES: COc1ccc(NC(=O)CN(C)C(=O)c2cc(-c3ccco3)nc3ccccc23)cc1] | |
| 40 | 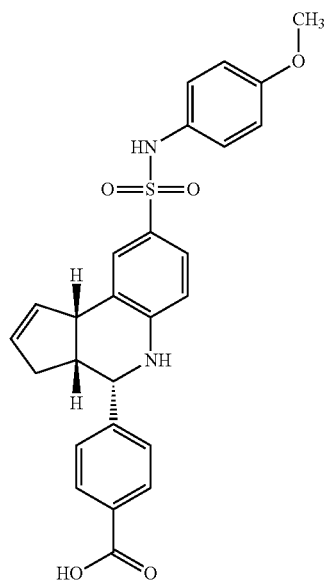 [SMILES: COc1ccc(NS(=O)(=O)c2ccc3c(c2)[C@H]2C=CC[C@H]2[C@@H](c2ccc(C(=O)O)cc2)N3)cc1] | |
| 41 | 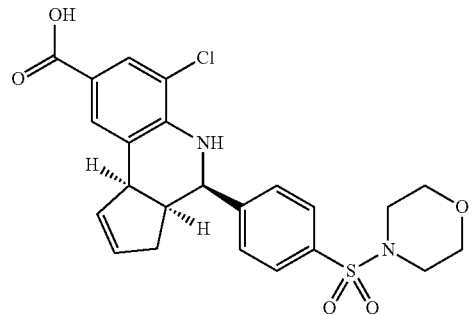 [SMILES: O=C(O)c1cc(Cl)c2c(c1)[C@@H]1C=CC[C@@H]1[C@H](c1ccc(S(=O)(=O)N3CCOCC3)cc1)N2] | |

TABLE 1-continued

Additional retinoic acid compounds

| No. | STRUCTURE | Formula |
|---|---|---|
| 42 | 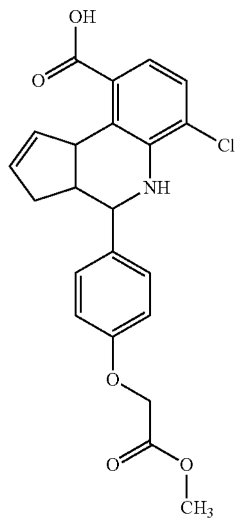 [SMILES: COC(=O)COc1ccc(C2Nc3c(Cl)ccc(C(=O)O)c3C3C=CCC32)cc1] | |
| 43 | 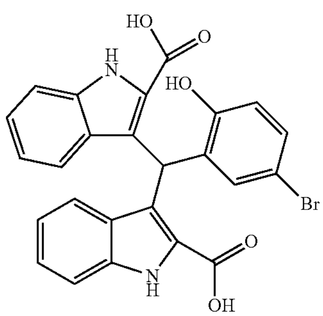 [SMILES: O=C(O)c1[nH]c2ccccc2c1C(c1cc(Br)ccc1O)c1c(C(=O)O)[nH]c2ccccc12] | |
| 44 | 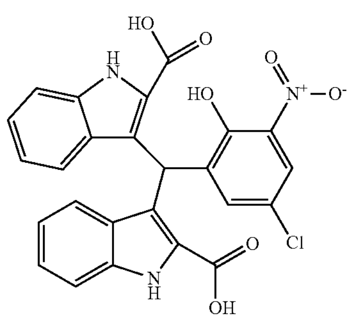 [SMILES: O=C(O)c1[nH]c2ccccc2c1C(c1cc(Cl)cc([N+](=O)[O-])c1O)c1c(C(=O)O)[nH]c2ccccc12] | |
| 45 | 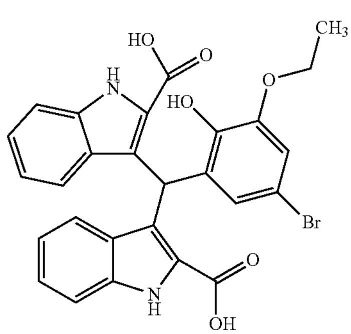 [SMILES: CCOc1cc(Br)cc(C(c2c(C(=O)O)[nH]c3ccccc23)c2c(C(=O)O)[nH]c3ccccc23)c1O] | |

TABLE 1-continued

Additional retinoic acid compounds

| No. | STRUCTURE | Formula |
|---|---|---|
| 46 | 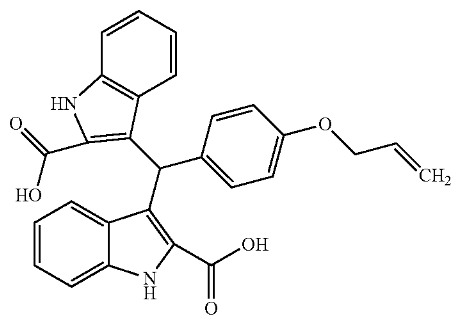 [SMILES: C=CCOc1ccc(C(c2c(C(=O)O)[nH]c3ccccc23)c2c(C(=O)O)[nH]c3ccccc23)cc1] | |
| 47 | 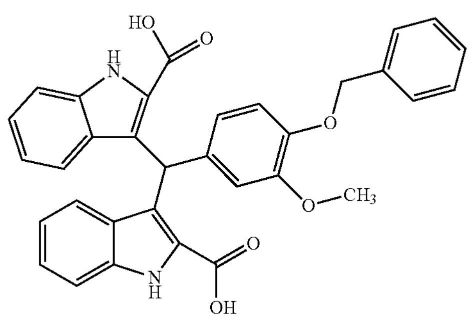 [SMILES: COc1cc(C(c2c(C(=O)O)[nH]c3ccccc23)c2c(C(=O)O)[nH]c3ccccc23)ccc1OCc1ccccc1] | |
| 48 | 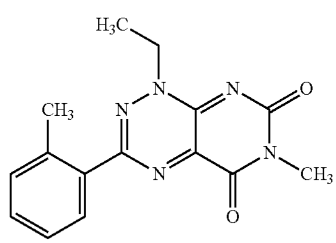 [SMILES: CCn1nc(-c2ccccc2C)nc2c(=O)n(C)c(=O)nc1-2] | |
| 49 | 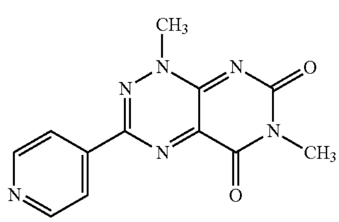 [SMILES: Cn1nc(-c2ccncc2)nc2c(=O)n(C)c(=O)nc1-2] | |
| 50 | 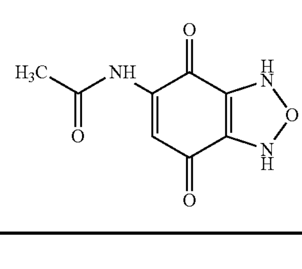 | |

In some embodiments, the retinoic acid compound has a structure according to the following formula,

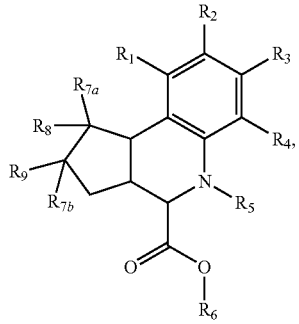

(I)

or a stereoisomer thereof, or a pharmaceutically acceptable salt thereof, where each of $R_1$, $R_2$, $R_3$, and $R_4$ is, independently, H, optionally substituted C1-C6 alkyl, OH, optionally substituted C1-C6 alkoxy, halogen, nitro, optionally substituted C1-C6 acyl, or $CO_2R_{10}$;

each of $R_5$, $R_6$, and $R_{10}$ is, independently, H or optionally substituted C1-C6 alkyl;

$R_{7a}$ and $R_{7b}$ are both H, or $R_{7a}$ and $R_{7b}$ combine to form a carbon-carbon double bond; and each of $R_8$ and $R_9$ is, independently, H, optionally substituted C1-C6 alkyl, OH, optionally substituted C1-C6 alkoxy, optionally substituted aryloxy, SH, optionally substituted thioaryloxy, halogen, optionally substituted C1-C6 acyl.

In some embodiments, not more than one of $R_1$-$R_4$ can be nitro.

In some embodiments, at least one of $R_1$-$R_4$ is OH, halogen (e.g., F, Cl, or Br), optionally substituted C1-C6 alkyl (e.g., $CH_3$ or $CF_3$), optionally substituted C1-C6 acyl (e.g., $CO_2Me$) or $CO_2R_{10}$ (e.g., $CO_2H$).

In some embodiments, 1, 2, or 3 of $R_1$-$R_4$ is halogen (e.g., F, Cl, or Br).

In some embodiments, $R_5$ and $R_6$ are both H.

In some embodiments, $R_{7a}$ and $R_{7b}$ combine to form a carbon-carbon double bond. In further embodiments, both $R_8$ and $R_9$ are H.

In some embodiments, $R_{7a}$ and $R_{7b}$ are both H.

In some embodiments, the retinoic acid compound is any of Compounds 1-8 of Table 1.

In some embodiments, the retinoic acid compound has a structure according to the following formula,

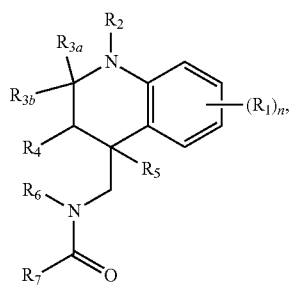

(II)

or a stereoisomer thereof, or a pharmaceutically acceptable salt thereof, wherein n is 0, 1, 2, 3, or 4;

each $R_1$, when present, is, independently, optionally substituted C1-C6 alkyl, OH, optionally substituted C1-C6 alkoxy, halogen, nitro, or optionally substituted C1-C6 acyl;

$R_2$ is H or optionally substituted C1-C6 alkyl;

$R_{3a}$ and $R_{3b}$ are both H, or $R_{3a}$ and $R_{3b}$ combine to form a carbon-oxygen double bond;

$R_4$ and $R_5$ are both H, or $R_4$ and $R_5$ combine to form a carbon-carbon double bond;

$R_6$ is optionally substituted phenyl; and $R_7$ is optionally substituted C1-C6 alkyl.

In some embodiments, n is 0. In other embodiments, $R_{3a}$ and $R_{3b}$ combine to form a carbon-oxygen double bond. In still other embodiments, $R_2$ is H. In certain embodiments, $R_4$ and $R_5$ combine to form a carbon-carbon double bond. In other embodiments, $R_7$ is optionally substituted C1 alkyl (e.g., $CH_2Cl$). In other embodiments, $R_6$ is phenyl having 1, 2, 3, 4, or 5 substituents (e.g., $R_6$ is tolyl).

In some embodiments, the retinoic acid compound is any of compounds 9-10 in Table 1.

In some embodiments, the retinoic acid compound has a structure according to the following formula,

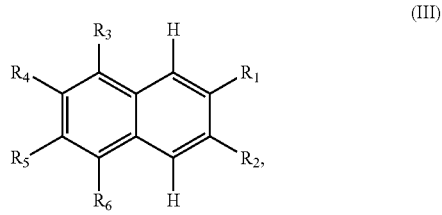

(III)

or a stereoisomer thereof, or a pharmaceutically acceptable salt thereof, where one of $R_1$ and $R_2$ is H, and the other is —NH (optionally substituted phenyl); and each of $R_3$, $R_4$, $R_5$, and $R_6$ is, independently, H, $OR_7$, or $SO_3R_8$;

each of $R_7$ and $R_8$ is, independently, H or optionally substituted C1-C6 alkyl; and wherein one and only one of $R_3$, $R_4$, $R_5$, and $R_6$ is $SO_3R_8$, and wherein one and only one of $R_3$, $R_4$, $R_5$, and $R_6$ is $OR_7$.

In some embodiments, the optionally substituted phenyl has 1, 2, 3, 4, or 5 substituents. In other embodiments, the phenyl is unsubstituted.

In some embodiments, one of $R_3$ or $R_6$ is OH, and one of $R_4$ or $R_5$ is $SO_3R_8$ (e.g., $SO_3H$).

In some embodiments, the retinoic acid compound is one of Compounds 13-15 of Table 1.

In some embodiments, the retinoic acid compound has a structure according to the following formula,

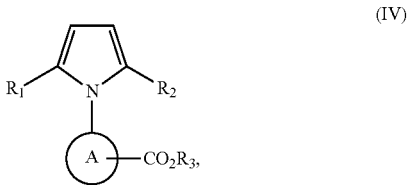

(IV)

or a stereoisomer thereof, or a pharmaceutically acceptable salt thereof, where each of $R_1$ and $R_2$ is, independently, optionally substituted C1-C6 alkyl; and A is a phenyl or 5-membered heteroaryl comprising a carboxyl substituent according to the substructure $CO_2R_3$, and where A comprises 0, 1, 2, or 3 substituent groups.

In some embodiments, each of $R_1$ and $R_2$ is, independently, unsubstituted C1-C6 alkyl (e.g., $CH_3$).

In other embodiments, the $CO_2R_3$ substituent is adjacent to the atom of substructure A that is covalently attached to the pyrrole nitrogen. In other embodiments, when A is phenyl, the $CO_2R_3$ substituent may be ortho, meta, or para to the pyrrole group.

In still other embodiments, $R_3$ is H.

In certain embodiments, A is phenyl or thienyl.

In some embodiments, the retinoic acid compound is any of compounds 17-19 of Table 1.

In still other embodiments, the retinoic acid compound has a structure according to the following formula,

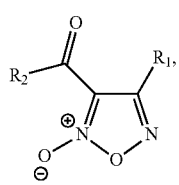

(V)

or a stereoisomer thereof, or a pharmaceutically acceptable salt thereof, where $R_1$ is CN or C(=O)$R_3$; and each $R_2$ and $R_3$ is, independently, optionally substituted phenyl or an optionally substituted 5-to-6-membered heteroaryl.

In some embodiments, $R_1$ is C(=O)$R_3$. In further embodiments, both $R_2$ and $R_3$ are the same group. In some embodiments, both $R_2$ and $R_3$ are phenyl having 0, 1, 2, or 3 substituents (e.g., methyl or methoxy). In other embodiments, both $R_2$ and $R_3$ are optionally substituted five-membered heteroaryls (e.g., optionally substituted pyrazolyl groups).

In some embodiments, $R_1$ is CN. In further embodiments, $R_3$ is an optionally substituted five-membered heteroaryl group (e.g., thienyl).

In some embodiments, the retinoic acid compound is any of compounds 28-32 of Table 1.

In some embodiments of any of the foregoing aspects, the arsenic trioxide and the retinoic acid compound are administered to a subject having a Pin1-associated disorder, wherein the subject has one or more cells with elevated levels of Pin1 activity (e.g., relative to a wild-type cell of the same cell type as the cell of interest).

In some embodiments of any of the foregoing aspects, administration of a combination of arsenic trioxide and a retinoic acid compound is sufficient to inhibit and/or degrade Pin1 in the subject. In some embodiments, this may include an increase in degradation of Pin1 of at least about 1%, 2%, 3%, 4%, 5%, 6%, 7%, 8%, 9%, 10%, 15%, 20%, 25%, 30%, 40%, 50%, 60%, 70%, 80%, 90%, 100%, 200%, 500%, 1000%, or greater relative to Pin1 activity prior to treatment with arsenic trioxide. In some embodiments, this may include a reduction in Pin1 activity of at least about 1%, 2%, 3%, 4%, 5%, 6%, 7%, 8%, 9%, 10%, 15%, 20%, 25%, 30%, 40%, 50%, 60%, 70%, 80%, 90%, 100%, 200%, 500%, 1000%, or greater relative to Pin1 activity prior to treatment with arsenic trioxide. In some embodiments, the administration of arsenic trioxide and a retinoic acid compound is more effective for inhibiting and/or degrading Pin1 in the subject than administration of the same quantities of either arsenic trioxide or the retinoic acid compound alone. In some embodiments, the administration of the arsenic trioxide and the retinoic acid compound is more effective for treating the Pin1-associated disorder than administration of the same quantities of either the arsenic trioxide or the retinoic acid compound alone.

In some embodiments of any of the foregoing aspects, the retinoic acid compound is administered in a low dose such as about 5 mg/kg body weight or less (e.g., about 0.1, 0.2, 0.5, 0.75, 1, 2, 3, 4, or 5 mg/kg body weight or less), 1.5 ug/g body weight or less (e.g., about 0.1, 0.2, 0.5, 0.75, 1, or 1.5 ug/g body weight or less), less than about 25 mg/m$^2$ (e.g., less than about 1, 2, 3, 4, 5, 6, 7, 8, 9, 10, 11, 12, 13, 14, 15, 16, 17, 18, 19, 20, 21, 22, 23, 24, or 25 mg/m$^2$), or between 25 mg/m$^2$ and 45 mg/m$^2$ (e.g., 25, 26, 27, 28, 29, 30, 31, 32, 33, 34, 35, 36, 37, 38, 39, 40, 41, 42, 43, 44, or 45 mg/m$^2$). In some embodiments, the low dose of the retinoic acid compound is a nontoxic dose of the retinoic acid compound.

In some embodiments of any of the foregoing aspects, the cell is in a solution or an explant. The method may further include administering an effective amount of the arsenic trioxide to a plurality of cells in the solution or explant. In some embodiments, the method includes administration of arsenic trioxide in an amount sufficient to reduce Pin1 activity in the plurality of cells and/or to increase degradation of Pin1 in the plurality of cells.

A subject may have a cell having a phenotype associated with elevated levels of Pin1 activity. Arsenic trioxide may be administered to the subject for the purpose of inhibiting, reducing, or reversing the phenotype in the cell. Accordingly, in some aspects, the invention features a method of inhibiting, reducing, or reversing a phenotype associated with elevated Pin1 activity in a cell, in a subject. This method includes: (a) providing a subject with a cell having a phenotype associated with elevated levels of Pin1 activity, and (b) administering arsenic trioxide to the subject only if the subject has been previously determined to have elevated levels of Pin1 activity (e.g., for the purpose of inhibiting the phenotype in the cell). In some embodiments, the subject has been previously determined to lack elevated levels of Pin1 activity and the subject is deemed less likely to be responsive to administration of arsenic trioxide (e.g., for the purpose of inhibiting the phenotype in the cell). In some embodiments, wherein the subject is deemed less likely to be responsive to administration of arsenic trioxide, arsenic trioxide is not administered to the subject.

In some embodiments, the phenotype associated with elevated levels of Pin1 activity in a cell includes increased cell death, an oncogenic transformation, and/or an autoimmune phenotype (e.g., overproduction of cytokines and/or the overproduction of autoantibodies).

In some embodiments, the cell is an oncogenic transformed cell or an autoimmune cell. In some embodiments, the cell is an oncogenic transformed cell and the cell becomes a non-transformed (e.g., not oncogenic) cell upon administration of the arsenic trioxide.

In some aspects, the invention features a method of treating a subject having a Pin1-associated disorder. This method includes: (a) providing a subject with a Pin1-associated disorder, and (b) administering arsenic trioxide to the subject only if the subject has been previously determined to have elevated levels of Pin1 activity (e.g., for the purpose of treating the Pin1-associated disorder). In some embodiments, the subject has been previously determined to lack elevated levels of Pin1 activity and the subject is deemed less likely to be responsive to administration of arsenic trioxide (e.g., for the purpose of treating the Pin1-associated disorder). In some embodiments, wherein the subject is deemed less likely to be responsive to administration of arsenic trioxide, arsenic trioxide is not administered to the subject. In some embodiments, the Pin1-associated disorder is not acute promyelocytic leukemia. In some embodiments, the subject lacks a PML-RARα fusion (e.g., the subject has been previously determined to lack a PML-RARα fusion).

In some aspects, the invention features a method of treating a Pin1-associated disorder in a subject. This method includes: (a) providing a subject with a Pin1-associated disorder, and (b) administering arsenic trioxide and a retinoic acid compound to the subject only if the subject has been previously determined to have elevated levels of Pin1 activity (e.g., for the purpose of treating the Pin1-associated disorder). In some embodiments, the subject has been previously determined to lack elevated levels of Pin1 activity and the subject is deemed less likely to be responsive to administration of arsenic trioxide and/or a retinoic acid compound (e.g., for the purpose of treating the Pin1-associated disorder). In some embodiments, wherein the subject is deemed less likely to be responsive to administration of arsenic trioxide, arsenic trioxide is not administered to the subject. In some embodiments, wherein the subject is deemed less likely to be responsive to administration of arsenic trioxide and/or a retinoic acid compound, arsenic trioxide and/or a retinoic acid compound is not administered to the subject. In some embodiments, the Pin1-associated disorder is not acute promyelocytic leukemia. In some embodiments, the subject lacks a PML-RARα fusion (e.g., the subject has been previously determined to lack a PML-RARα fusion).

In some embodiments, the retinoic acid compound is administered in a low dose such as about 5 mg/kg body weight or less (e.g., about 0.1, 0.2, 0.5, 0.75, 1, 2, 3, 4, or 5 mg/kg body weight or less), 1.5 ug/g body weight or less (e.g., about 0.1, 0.2, 0.5, 0.75, 1, or 1.5 ug/g body weight or less), less than about 25 mg/m$^2$ (e.g., less than about 1, 2, 3, 4, 5, 6, 7, 8, 9, 10, 11, 12, 13, 14, 15, 16, 17, 18, 19, 20, 21, 22, 23, 24, or 25 mg/m$^2$), or between 25 mg/m$^2$ and 45 mg/m$^2$ (e.g., 25, 26, 27, 28, 29, 30, 31, 32, 33, 34, 35, 36, 37, 38, 39, 40, 41, 42, 43, 44, or 45 mg/m$^2$). In some embodiments, the low dose of the retinoic acid compound is a nontoxic dose of the retinoic acid compound.

In some embodiments, arsenic trioxide and the retinoic acid compound may be administered concurrently (e.g., within about 1 min, 2 min, 5 min, 10 min, 20 min, 30 min, or 60 min) or separately. The arsenic trioxide may be administered either prior to or after the retinoic acid compound.

In some embodiments, the retinoic acid compound is all-trans retinoic acid (ATRA), 13-cis-retinoic acid, retinol, retinyl acetate, retinal, or AC-55640, or is a compound structurally similar to retinoic acid. In some embodiments, the retinoic acid compound is a Table 1 compound.

In some embodiments, administration of a combination of arsenic trioxide and a retinoic acid compound is sufficient to inhibit and/or degrade in1 in the subject. In some embodiments, this may include an increase in degradation of Pin1 of at least about 1%, 2%, 3%, 4%, 5%, 6%, 7%, 8%, 9%, 10%, 15%, 20%, 25%, 30%, 40%, 50%, 60%, 70%, 80%, 90%, 100%, 200%, 500%, 1000%, or greater relative to Pin1 activity prior to treatment with arsenic trioxide. In some embodiments, this may include a reduction in Pin1 activity of at least about 1%, 2%, 3%, 4%, 5%, 6%, 7%, 8%, 9%, 10%, 15%, 20%, 25%, 30%, 40%, 50%, 60%, 70%, 80%, 90%, 100%, 200%, 500%, 1000%, or greater relative to Pin1 activity prior to treatment with arsenic trioxide. In some embodiments, the administration of arsenic trioxide and a retinoic acid compound is more effective for inhibiting and/or degrading Pin1 in the subject than administration of the same quantities of either arsenic trioxide or the retinoic acid compound alone. In some embodiments, the administration of the arsenic trioxide and the retinoic acid compound is more effective for treating the Pin1-associated disorder than administration of the same quantities of either the arsenic trioxide or the retinoic acid compound alone.

In some aspects, the invention features a method of diagnosing and treating a Pin1-associated disorder in a subject. This method includes: (a) detecting whether elevated Pin1 activity is present in a sample obtained from the subject, (b) diagnosing the subject with a Pin1-associated disorder when the presence of elevated Pin1 activity is detected in the sample, and (c) administering arsenic trioxide to the diagnosed subject.

In some embodiments of the foregoing aspect, the detecting step (a) includes determining the levels of a Pin1 marker, wherein elevated levels of the Pin1 marker is indicative of elevated Pin1 activity.

In some embodiments, the method further includes administering a retinoic acid compound to the diagnosed subject. In some embodiments, the retinoic acid compound is administered in a low dose such as about 5 mg/kg body weight or less (e.g., about 0.1, 0.2, 0.5, 0.75, 1, 2, 3, 4, or 5 mg/kg body weight or less), 1.5 ug/g body weight or less (e.g., about 0.1, 0.2, 0.5, 0.75, 1, or 1.5 ug/g body weight or less), less than about 25 mg/m$^2$ (e.g., less than about 1, 2, 3, 4, 5, 6, 7, 8, 9, 10, 11, 12, 13, 14, 15, 16, 17, 18, 19, 20, 21, 22, 23, 24, or 25 mg/m$^2$), or between 25 mg/m$^2$ and 45 mg/m$^2$ (e.g., 25, 26, 27, 28, 29, 30, 31, 32, 33, 34, 35, 36, 37, 38, 39, 40, 41, 42, 43, 44, or 45 mg/m$^2$). In some embodiments, the low dose of the retinoic acid compound is a nontoxic dose of the retinoic acid compound.

In some embodiments, arsenic trioxide and the retinoic acid compound may be administered concurrently (e.g., within about 1 min, 2 min, 5 min, 10 min, 20 min, 30 min, or 60 min) or separately. The arsenic trioxide may be administered either prior to or after the retinoic acid compound.

In some embodiments, the retinoic acid compound is all-trans retinoic acid (ATRA), 13-cis-retinoic acid, retinol, retinyl acetate, retinal, or AC-55640, or is a compound structurally similar to retinoic acid. In some embodiments, the retinoic acid compound is a Table 1 compound.

In some embodiments, administration of a combination of arsenic trioxide and a retinoic acid compound is sufficient to inhibit and/or degrade Pin1 in the subject. In some embodiments, this may include an increase in degradation of Pin1 of at least about 1%, 2%, 3%, 4%, 5%, 6%, 7%, 8%, 9%, 10%, 15%, 20%, 25%, 30%, 40%, 50%, 60%, 70%, 80%, 90%, 100%, 200%, 500%, 1000%, or greater relative to Pin1 activity prior to treatment with arsenic trioxide. In some embodiments, this may include a reduction in Pin1 activity of at least about 1%, 2%, 3%, 4%, 5%, 6%, 7%, 8%, 9%, 10%, 15%, 20%, 25%, 30%, 40%, 50%, 60%, 70%, 80%, 90%, 100%, 200%, 500%, 1000%, or greater relative to Pin1 activity prior to treatment with arsenic trioxide. In some embodiments, the administration of arsenic trioxide and a retinoic acid compound is more effective for inhibiting and/or degrading Pin1 in the subject than administration of the same quantities of either arsenic trioxide or the retinoic acid compound alone. In some embodiments, the administration of the arsenic trioxide and the retinoic acid compound is more effective for treating the Pin1-associated disorder than administration of the same quantities of either the arsenic trioxide or the retinoic acid compound alone.

In some of embodiments of any of the foregoing aspects, the method includes administration of arsenic trioxide and/or a retinoic acid compound in an amount sufficient to reduce Pin1 activity in a cell to about the level of Pin1 activity present in a wild-type cell (e.g., a wild-type cell of the same cell type as a cell of interest) and/or to reduce Pin1 activity in a subject. In some embodiments of any of the foregoing aspects, the method includes administration of arsenic trioxide in an amount sufficient to inhibit and/or degrade Pin1 in a cell and/or a subject. In some embodiments, this may include an increase in degradation of Pin1 of at least about 1%, 2%, 3%, 4%, 5%, 6%, 7%, 8%, 9%, 10%, 15%, 20%, 25%, 30%, 40%, 50%, 60%, 70%, 80%, 90%, 100%, 200%, 500%, 1000%, or greater relative to Pin1 activity prior to treatment with arsenic trioxide. In some embodiments, this may include a reduction in Pin1 activity of at least about 1%, 2%, 3%, 4%, 5%, 6%, 7%, 8%, 9%, 10%, 15%, 20%, 25%, 30%, 40%, 50%, 60%, 70%, 80%, 90%, 100%, 200%, 500%, 1000%, or greater relative to Pin1 activity prior to treatment with arsenic trioxide.

In some embodiments of any of the foregoing aspects, Pin1 activity may be reduced in a cell and/or a subject to a therapeutically desirable level (e.g., a reduction in Pin1 activity of at least about 1%, 2%, 3%, 4%, 5%, 6%, 7%, 8%, 9%, 10%, 15%, 20%, 25%, 30%, 40%, 50%, 60%, 70%, 80%, 90%, 100%, 200%, 500%, 1000%, or greater, or to about the level of Pin1 activity present in a wild-type cell).

In some embodiments of any of the foregoing aspects, arsenic trioxide is administered in a low dose, such as 2 mg/kg body weight or less (e.g., about 0.01, 0.02, 0.03, 0.032, 0.04, 0.05, 0.06, 0.07, 0.08, 0.09, 0.1, 0.15, 0.16, 0.2, 0.3, 0.4, 0.5, 0.6, 0.7, 0.8, 0.9, 1.0, 1.25, 1.5, 1.75, or 2 mg/kg body weight or less), between about 0.5 mg/kg and about 12 mg/kg body weight (e.g., about 0.5, 0.6, 0.7, 0.8, 0.9, 1, 2, 3, 4, 5, 6, 7, 8, 9, 10, 11, or 12 mg/kg body weight), or less than about 6 ug/g body weight (e.g., less than about 0.1, 0.2, 0.5, 0.75, 1, 2, 3, 4, 5, or 6 ug/g body weight). In some embodiments, a low dose of arsenic trioxide is about 0.15, about 0.16, or about 0.032 mg/kg body weight. In some embodiments, the low dose of the arsenic trioxide is a nontoxic dose of the arsenic trioxide. In some embodiments, the low dose of arsenic trioxide is administered in combination with a low dose of a retinoic acid compound. In some embodiments the low dose of arsenic trioxide and the low dose of retinoic acid compound are nontoxic.

In some embodiments of any of the foregoing aspects, arsenic trioxide and/or the retinoic acid compound may be formulated for controlled or extended release. Many strategies can be pursued to obtain controlled and/or extended release in which the rate of release outweighs the rate of metabolism of the therapeutic compound. For example, controlled release can be obtained by the appropriate selection of formulation parameters and ingredients (e.g., appropriate controlled release compositions and coatings). Examples include single or multiple unit tablet or capsule compositions, oil solutions, suspensions, emulsions, microcapsules, microspheres, nanoparticles, patches, and liposomes. The release mechanism may be controlled such that the arsenic trioxide and/or the retinoic acid compound is released at period intervals, the release could be simultaneous, or a delayed release of one of the agents of the combination can be affected, when the early release of one particular agent is preferred over the other. Wherein arsenic trioxide is administered to a subject, it may be formulated for controlled or extended release. Wherein arsenic trioxide and a retinoic acid compound are administered to a subject, the arsenic trioxide may be formulated for controlled or extended release, the retinoic acid compound may be formulated for controlled or extended release, or both the arsenic trioxide and the retinoic acid compound may be formulated for controlled or extended release.

In some embodiments of any of the foregoing aspects, arsenic trioxide and/or the retinoic acid compound is administered to a subject having a Pin1-associated disorder, wherein the subject has one or more cells with elevated levels of Pin1 activity (e.g., relative to a wild-type cell of the same cell type as the cell of interest). In some embodiments of any of the foregoing aspects, reduction of Pin1 activity in the subject may treat the Pin1-associated disorder in the subject.

In some embodiments of any of the foregoing aspects, wherein arsenic trioxide and/or a retinoic acid are administered to a subject, the subject may be a mammal (e.g., a human, cat, dog, horse, cow, pig, monkey). In the preferred embodiment, the subject is a human.

In some embodiments of any of the foregoing aspects, the method further includes monitoring Pin1 activity after the administration of arsenic trioxide and/or a retinoic acid compound. Monitoring may include determining the level of a Pin1 marker, wherein the level of the Pin1 marker is indicative of the level of Pin1 activity.

In some embodiments of any of the foregoing aspects, the levels of Pin1 activity in the subject may be determined by measuring the levels of at least one Pin1 marker, wherein elevated levels of the Pin1 marker is indicative of elevated Pin1 activity. Non-limiting examples of Pin1 markers include nucleic acid molecules (e.g., mRNA, DNA) that correspond to some or all of a Pin1 gene, peptide sequences (e.g., amino acid sequences) that correspond to some or all of a Pin1 protein, nucleic acid sequences which are homologous to Pin1 gene sequences, peptide sequences which are homologous to Pin1 peptide sequences, alteration of Pin1 protein, antibodies to Pin1 protein, substrates of Pin1 protein, binding partners of Pin1 protein, alteration of Pin1 binding partners, and activity of Pin1. In some embodiments, alteration of a Pin1 protein may include a post-translational modification (e.g., phosphorylation, acetylation, methylation, lipidation, or any other post-translational modification known in the art) of Pin1. In some embodiments, a Pin1 marker is the level of Pin expression (e.g., Pin1 protein expression levels and/or Pin1 mRNA expression levels) in a subject. Elevated levels of a Pin1 marker include, for example, levels at least about 1%, 2%, 3%, 4%, 5%, 6%, 7%, 8%, 9%, 10%, 15%, 20%, 25%, 30%, 40%, 50%, 60%, 70%, 80%, 90%, 100%, 200%, 500%, 1000%, or greater than the marker levels measured in a normal (e.g., wild-type and/or disease fee) subject, tissue, or cell.

Pin1 markers include aberrant post-translational modifications of Pin1, such as reduced phosphorylation of S71 of Pin1, deacetylation of K13 of Pin1, deacetylation of K46 of Pin1, dephosphorylation of S16 of Pin1, desumoylation of K63 of Pin1, phosphorylation of S65 of Pin1, and/or phosphorylation of S138 of Pin1. Pin1 markers may further include Pin1 mRNA expression level, Pin1 protein expression level, and/or expression of a downstream effector of Pin1.

In some embodiments of any of the foregoing aspects, the cell and/or subject has an inherited trait or a somatic mutation. In some embodiments, the elevated Pin1 activity level is due to an inherited trait or a somatic mutation. Non-limiting examples an inherited traits or a somatic mutation include a Q33K, E100D, R36P, G39C, T143M, and/or E145K mutation of Pin1.

In some embodiments of any of the foregoing aspects, the method further includes determining the Pin1 activity in a subject and/or cell after administration of arsenic trioxide and/or a retinoic acid compound (e.g., by determining the level of a Pin1 marker in a sample obtained from the subject, wherein the level of the Pin1 marker is indicative of the level of Pin1 activity).

In some embodiments of any of the foregoing aspects, wherein a subject has a Pin1-associated disorder, the Pin1-associated disorder is a proliferative disease, an inflammatory condition, or an autoimmune disorder.

In some embodiments of any of the foregoing aspects, wherein a subject has a Pin1-associated disorder, the proliferative disease is a cancer, such as breast cancer (e.g., triple-negative breast cancer), liver cancer (e.g., HBV-related liver cancer), colon cancer, pancreatic cancer, ovarian cancer, prostate cancer, cervical cancer, uterine cancer, testicular cancer, lung cancer, brain cancer, throat cancer, leukemia, Hodgkin's disease, non-Hodgkin's disease, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, or retinoblastoma. Preferably, the cancer is breast cancer (e.g., triple-negative breast cancer) or liver cancer (e.g., HBV-related liver cancer).

In some embodiments of any of the foregoing aspects, wherein a subject has a Pin1-associated disorder, the inflammatory condition is arthritis, asthma, osteoarthritis, joint inflammation, inflammatory joint pain, inflammatory pain relayed via dorsal root ganglia (DRG), an infectious disease, an autoimmune disease, peripheral nerve injury, neuropathic pain, temporomandibular joint (TMJ) disorder, fibromyalgia, hyperalgesia, mechanical allodynia, chronic/persistent pain, acute pain, postoperative pain, acute lung injury (ALI), acute respiratory distress syndrome (ARDS), cystic fibrosis, chronic obstructive pulmonary disease (COPD), allergic asthma, severe asthma, bronchial mucosal inflammation, acute inflammatory response, chronic inflammation, abscess, thrombosis, allergic inflammation, sepsis, septic shock, ischemia-reperfusion injury, inflammatory bowel disease, colitis, intestinal inflammation, gastroesophageal reflux disease, ocular neovascularisation, posterior ocular inflammation, retinopathy, psoriasis, eczema, periodontitis, peritonitis, celiac disease, chronic prostatitis, benign prostatichypertrophy, glomerulonephritis, hypersensitivities, inflammatory bowel diseases, pelvic inflammatory disease, sarcoidosis, transplant rejection, vasculitis, interstitial cystitis, sterile inflammation, gout, silicosis, siderosis, joint loosening, or asbestosis. Preferably, the inflammatory condition is arthritis or asthma.

In some embodiments of any of the foregoing aspects, wherein a subject has a Pin1-associated disorder, the autoimmune disorder is lupus erythematosus, rheumatoid arthritis, multiple sclerosis (MS), encephalomyelitis, Addison's disease, agammaglbulinemia, alopecia areata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmunehemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo concentric sclerosis, Behcet's disease, Berger's disease, Bickerstaff's encephalitis, Blau syndrome, bullous pemphigoid, chronic bronchitis, Castleman's disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's syndrome, cutaneous leukocytoclastic vasculitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritis, epidermolysis bullosa acquisita, erythema nodosum, erythroblastosis fetalis, essential mixed cryoglubulinemia, Evan's syndrome, fibrodysplasia ossificans progressive, fibrosing alveolitis, gastritis, gastrointestinal pemphigoid, giant cell arteritis, glomerulonephritis, Goodpasture's syndrome, Grave's disease, Guillain-Barre syndrome, Hashimoto's encephalopathy, Hashimoto's thyroiditis, Henoch-Schonlein purpura, herpes gestationis, hidradenitis suppurativa, Hughes-Stovin syndrome, hypertension, hypogammaglobulinemia, idiopathic inflammatory demyelinating diseases, idiopathic pulmonary fibrosis, idiopathic thrombocytopenic purpura, IgA nephropathy, inclusion body myositis, chronic inflammatory demyelinating polyneuropathy, interstitial cystitis, juvenile idiopathic arthritis, Kawasaki's disease, Lambert-Eaton myasthenic syndrome, leukocytoclastic vasculitis, lichen planus, lichen sclerosus, linear IgA disease, Majeed syndrome, Meniere's disease, microscopic polyangiitis, mixed connective tissue disease, morphea, Mucha-Habermann disease, myasthenia gravis, myositis, narcolepsy, neuromyelitis optica, neuromyotonia, ocular cicatricial pemphigoid, opsoclonus myoclonus syndrome, Ord's thyroiditis, palindromic rheumatism, PANDAS, paraneoplastic cerebellar degeneration, paroxysmal nocturnal hemoglobinuria, Parry Romberg syndrome, Parsonage-Turner syndrome, pars planitis, pemphigus vulgaris, pernicious anaemia, perivenous encephalomyelitis, peripheral vascular disease, POEMS syndrome, polyarteritis nodosa, polymyalgia rheumatic, polymyositis, primary biliary cirrhosis, primary sclerosing cholangitis, progressive inflammatory neuropathy, psoriatic arthritis, psoriasis, pyoderma gangrenosum, pure red cell aplasia, Rasmussen's encephalitis, raynaud phenomenon, relapsing polychondritis, Reiter's syndrome, restless leg syndrome, retroperitoneal fibrosis, rheumatic fever, rheumatoid arthritis, Schnitzler syndrome, scleritis, scleroderma, serum sickness, chronic sinusitis, Sjogren's syndrome, spondyloarthropathy, stiff person syndrome, subacute bacterial endocarditis, Susac's syndrome, Sweet's syndrome, sympathetic ophthalmia, Takayasu's arteritis, temporal arteritis, thrombocytopenia, Tolosa-Hunt syndrome, transverse myelitis, ulcerative colitis, undifferentiated connective tissue disease, undifferentiated spondyloarthropathy, vitiligo, or Wegener's granulomatosis. Preferably, the autoimmune disorder is lupus erythematosus.

In some embodiments of any of the foregoing aspects, the Pin1-associated disorder is not acute promyelocytic leukemia.

In some embodiments of any of the foregoing aspects, the subject lacks a PML-RARα fusion (e.g., the subject has been previously determined to lack a PML-RARα fusion).

Definitions

As used herein, "Pin1 activity" refers to binding of the protein Pin1 to a substrate (e.g., a substrate protein) and Pin1-catalyzed isomerization of the substrate. Pin1 generally acts as a peptidyl-prolyl isomerase (PPIase) that catalyzes prolyl isomerization of the substrate (e.g., conversion of a peptidyl-prolyl group on the substrate from a trans conformation to a cis conformation, or vice versa). "Elevated Pin1 activity" or "elevated levels of Pin1 activity," as used herein, generally refer to an increase in Pin1-catalyzed isomerization of one or more Pin1 substrates, for example, relative to a reference level of Pin1 activity. In some embodiments, the reference level of Pin1 activity is the level of Pin1 activity in a wild-type cell (e.g., a wild-type cell of the same cell type as a cell of interest). In some embodiments, the reference level of Pin1 activity is the level of Pin1 activity in a wild-type subject (e.g., a subject lacking a Pin1-associated disorder), such that an increase in Pin1 activity in a subject of interest relative to a wild-type subject indicates that the subject of interest has elevated Pin1 activity. In some embodiments, alteration in Pin1 activity can be assessed by determining the levels of a Pin1 marker in a cell and/or a subject of interest, relative to a reference cell or subject (e.g., a wild-type cell or subject). Elevated levels of Pin1 activity include, for example, Pin1 activity levels at least about 1%, 2%, 3%, 4%, 5%, 6%, 7%, 8%, 9%, 10%, 15%, 20%, 25%, 30%, 40%, 50%, 60%, 70%, 80%, 90%, 100%, 200%, 500%, 1000%, or greater than the activity level measured in a normal (e.g., wild-type and/or disease fee) subject, tissue, or cell.

By a "therapeutically desirable" level of Pin1 activity is meant a level of Pin1 activity present in a healthy, unaffected, and/or wild-type cell, tissue, or subject. In some embodiments, a subject with an elevated level of Pin1 activity (e.g., a subject having a Pin1-associated disorder, as described herein) may be desirably treated with one or more agents of the invention (e.g., arsenic trioxide and/or a retinoic acid compound) to lower Pin1 activity in the subject to levels present in a healthy counterpart, thereby restoring the subject to a therapeutically desirable level of Pin1 activity (e.g., a level of Pin1 activity present in the healthy counterpart).

As used herein, the term "Pin1 marker" refers to a marker which is capable of being indicative of Pin1 activity levels (e.g., in a sample obtained from a cell or subject of interest). Non-limiting examples of Pin1 markers include nucleic acid molecules (e.g., mRNA, DNA) that correspond to some or all of a Pin1 gene, peptide sequences (e.g., amino acid sequences) that correspond to some or all of a Pin1 protein, nucleic acid sequences which are homologous to Pin1 gene sequences, peptide sequences which are homologous to Pin1 peptide sequences, alteration of Pin1 protein, antibodies to Pin1 protein, substrates of Pin1 protein, binding partners of Pin1 protein, alteration of Pin1 binding partners, and activity of Pin1. In some instances, alteration of a Pin1 protein may include a post-translational modification (e.g., phosphorylation, acetylation, methylation, lipidation, or any other post-translational modification known in the art) of Pin1. In some instances, a Pin1 marker is the level of Pin expression (e.g., Pin1 protein expression levels and/or Pin1 mRNA expression levels) in a subject. By "elevated levels of a Pin1 marker" is meant a level of Pin1 marker that is altered, which may, in some instances, indicate the presence of elevated Pin1 activity. Elevated levels of a Pin1 marker include, for example, levels at least about 1%, 2%, 3%, 4%, 5%, 6%, 7%, 8%, 9%, 10%, 15%, 20%, 25%, 30%, 40%, 50%, 60%, 70%, 80%, 90%, 100%, 200%, 500%, 1000%, or greater than, or about 1%, 2%, 3%, 4%, 5%, 6%, 7%, 8%, 9%, 10%, 15%, 20%, 25%, 30%, 40%, 50%, 60%, 70%, 80%, 90%, 100% less than the marker levels measured in a normal (e.g., wild-type and/or disease fee) subject, tissue, or cell.

By the term "arsenic trioxide" is meant a compound having the formula $As_2O_3$ and derivatives thereof. Arsenic trioxide generally has the following structure:

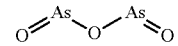

Derivatives of arsenic trioxide may include, for example, arsenic ores, such as, e.g., arsenopyrite (grey arsenic; FeAsS), realgar (also known as sandarach or red arsenic; AsS), orpiment (yellow arsenic; As2S3), and arsenolite, an oxidation product of arsenic sulphides (white arsenic; As2O3). Arsenic trioxide exhibits high toxicity in mammals, such as humans. In some instances, arsenic trioxide ingestion can result in severe side effects, including vomiting, abdominal pain, diarrhea, bleeding, convulsions, cardiovascular disorders, inflammation of the liver and kidneys, abnormal blood coagulation, hair loss, and death. In certain instances, arsenic trioxide poisoning may rapidly lead to death. Chronic exposure to even low levels of arsenic trioxide can result in arsenicosis and skin cancer. Arsenic trioxide is therefore desirably administered to a subject at low enough doses to minimize toxicity. As described herein, arsenic trioxide and derivatives thereof may be effective at inducing Pin1 degradation, thereby reducing Pin1 activity levels. In certain instances, organic arsenic compounds are converted to inorganic compounds when absorbed in a biological system (see, e.g., Frith, *J. Military Vet. Health* 21(4): 11-17, 2013). Arsenic derivatives and uses thereof are described, for example, in Waxman et al. (*Oncologist* 6: 3-10, 2001; incorporated herein by reference).

By the term "retinoic acid compound" is meant a compound that is either (a) the diterpene retinoic acid, or a derivative thereof, or (b) a compound having the structure $R^1$—$Ar^1$-$L^1Ar^2$-$L^2$-C(=O)$R^3$ (Formula (VI)). Generally, the retinoic acid compounds of the invention may reduce Pin1 activity (e.g., as determined by a fluorescence polarization-based displacement assay or PPIase assay, as described, for example, in PCT Publication No. WO2012/125724). This reduction in Pin1 activity can be, for example, a reduction of at least 5%, at least 10%, at least 20%, at least 30%, at least 40%, at least 50%, at least 60%, at least 70%, at least 80%, at least 90%, at least 95%, at least 99%, or greater than 99%. As described herein, arsenic trioxide and derivatives thereof may be effective at inducing Pin1 degradation, thereby reducing Pin1 activity levels. Exemplary retinoic acid compounds described herein (including derivatives thereof) include, without limitation, all-trans retinoic acid (ATRA), 13-cis retinoic acid (13cRA), and retinoic acid compounds, and derivatives thereof, e.g., as described herein. In particular, examples of retinoic acid compounds include those shown in Tables 2 and 3 below.

TABLE 2

Exemplary Retinoic Acid Compounds

| CID | IUPAC | Other names |
|---|---|---|
| 444795 | (2E,4E,6E,8E)-3,7-dimethyl-9-(2,6,6-trimethylcyclohexen-1-yl)nona-2,4,6,8-tetraenoic acid | Retinoic acid; tretinoin; Vitamin A acid |
| 25145416 | (2Z,4E,6Z,8Z)-3,7-dimethyl-9-(2,6,6-trimethylcyclohexen-1-yl)nona-2,4,6,8-tetraenoic acid | |
| 23275881 | (2Z,4Z,6E,8Z)-3,7-dimethyl-9-(2,6,6-trimethylcyclohexen-1-yl)nona-2,4,6,8-tetraenoic acid | |
| 12358678 | (2E,4E,6E,8Z)-3,7-dimethyl-9-(2,6,6-trimethylcyclohexen-1-yl)nona-2,4,6,8-tetraenoic acid | CHEMBL44478; CHEBI: 168407; AC-540 |
| 10881132 | (2Z,4Z,6E,8E)-3,7-dimethyl-9-(2,6,6-trimethylcyclohexen-1-yl)nona-2,4,6,8-tetraenoic acid | |
| 10638113 | (2E,4E,6E,8E)-3,7-dimethyl-9-(2,6,6-trimethylcyclohexen-1-yl)nona-2,4,6,8-tetraenoic acid | |
| 9861147 | (2E,4Z,6Z,8E)-3,7-dimethyl-9-(2,6,6-trimethylcyclohexen-1-yl)nona-2,4,6,8-tetraenoic acid | |
| 9796370 | (2E,4Z,6E,8E)-3,7-dimethyl-9-(2,6,6-trimethylcyclohexen-1-yl)nona-2,4,6,8-tetraenoic acid | 1tyr; (11Z)-retinoic acid; 11-cis-Retinoic acid |
| 6603983 | (2E,4Z,6E,8Z)-3,7-dimethyl-9-(2,6,6-trimethylcyclohexen-1-yl)nona-2,4,6,8-tetraenoic acid | Tocris-0695; Lopac-R-2625; Lopac-R-3255 |
| 6419708 | (2Z,4E,6Z,8E)-3,7-dimethyl-9-(2,6,6-trimethylcyclohexen-1-yl)nona-2,4,6,8-tetraenoic acid | 9,13-di-cis-RA; 9,13-Di-cis-retinoic acid; 9-cis,13-cis-Retinoic acid |
| 5282379 | (2Z,4E,6E,8E)-3,7-dimethyl-9-(2,6,6-trimethylcyclohexen-1-yl)nona-2,4,6,8-tetraenoic acid | Isotretinoin; 13-cis-Retinoic acid; Accutan |
| 449171 | (2E,4E,6Z,8E)-3,7-dimethyl-9-(2,6,6-trimethylcyclohexen-1-yl)nona-2,4,6,8-tetraenoic acid | Alitretinoin; Panretin; 9-CIS-RETINOIC ACID |
| 5538 | 3,7-dimethyl-9-(2,6,6-trimethylcyclohexen-1-yl)nona-2,4,6,8-tetraenoic acid | Spectrum_001676; SpecPlus_000696; AC1L1KKH |
| 54305566 | 2,4-dideuterio-7-methyl-3-(trideuteriomethyl)-9-(2,6,6-trimethylcyclohexen-1-yl)nona-2,4,6,8-tetraenoic acid | |
| 54305565 | 9-[3,3-dideuterio-6,6-dimethyl-2-(trideuteriomethyl)cyclohexen-1-yl]-3,7-dimethylnona-2,4,6,8-tetraenoic acid | |
| 10566385 | (2E,4E,6Z,8E)-7-methyl-3-(trideuteriomethyl)-9-(2,6,6-trimethylcyclohexen-1-yl)nona-2,4,6,8-tetraenoic acid | |
| 10518761 | (2E,4E,6Z,8E)-7-methyl-9-(2,6,6-trimethylcyclohexen-1-yl)-3-(tritritiomethyl)nona-2,4,6,8-tetraenoic acid | |
| 10470200 | (2E,4Z,6Z,8E)-4,5-dideuterio-3,7-dimethyl-9-(2,6,6-trimethylcyclohexen-1-yl)nona-2,4,6,8-tetraenoic acid | |
| 10425032 | (2E,4E,6Z,8E)-4,5-dideuterio-3,7-dimethyl-9-(2,6,6-trimethylcyclohexen-1-yl)nona-2,4,6,8-tetraenoic acid | |
| 10357701 | (2E,4E,6Z,8E)-3,7-dimethyl-9-(2,6,6-trimethyl-4,5-ditritiocyclohexen-1-yl)nona-2,4,6,8-tetraenoic acid | |
| 10267048 | (2E,4E,6Z,8E)-3,7-dimethyl-9-(2,6,6-trimethylcyclohexen-1-yl)-4,5-ditritionona-2,4,6,8-tetraenoic acid | |
| 10086398 | (2Z,4Z,6Z,8E)-3,7-dimethyl-9-(2,6,6-trimethylcyclohexen-1-yl)-4,5-ditritionona-2,4,6,8-tetraenoic acid | |
| 10086397 | (2E,4E,6Z,8E)-3,7-dimethyl-9-(2,6,6-trimethyl-3,4-ditritiocyclohexen-1-yl)nona-2,4,6,8-tetraenoic acid | |
| 10063649 | (2E,4E,6Z,8E)-9-[2,6-dimethyl-6-(trideuteriomethyl)cyclohexen-1-yl]-3,7-dimethylnona-2,4,6,8-tetraenoic acid | |
| 10040620 | (2E,4E,6Z,8E)-9-(4,5-dideuterio-2,6,6-trimethylcyclohexen-1-yl)-3,7-dimethylnona-2,4,6,8-tetraenoic acid | |
| 10017935 | (2Z,4E,6E,8E)-3,7-dimethyl-9-(2,6,6-trimethylcyclohexen-1-yl)-4,5-ditritionona-2,4,6,8-tetraenoic acid | |
| 10017822 | (2E,4E,6Z,8E)-9-(3,4-dideuterio-2,6,6-trimethylcyclohexen-1-yl)-3,7-dimethylnona-2,4,6,8-tetraenoic acid | |
| 9995220 | (2E,4Z,6Z,8E)-3,7-dimethyl-9-(2,6,6-trimethylcyclohexen-1-yl)-4,5-ditritionona-2,4,6,8-tetraenoic acid | |
| 9972327 | (2Z,4Z,6E,8E)-3,7-dimethyl-9-(2,6,6-trimethylcyclohexen-1-yl)-4,5-ditritionona-2,4,6,8-tetraenoic acid | |
| 9972326 | (2E,4Z,6E,8E)-3,7-dimethyl-9-(2,6,6-trimethylcyclohexen-1-yl)-4,5-ditritionona-2,4,6,8-tetraenoic acid | |

TABLE 2-continued

Exemplary Retinoic Acid Compounds

| CID | IUPAC | Other names |
|---|---|---|
| 9839397 | (2E,4E,6Z,8E)-3,7-dimethyl-9-(2,6,6-trimethylcyclohexen-1-yl)-5-tritionona-2,4,6,8-tetraenoic acid | |
| 6913160 | (2Z,4E,6Z,8E)-3,7-dimethyl-9-(2,6,6-trimethylcyclohexen-1-yl)-5-tritionona-2,4,6,8-tetraenoic acid | Retinoic-11-t acid; AC1OC7MJ; all-trans-(11-3H)-Retinoic acid |
| 6913136 | (2Z,4E,6Z,8E)-3,7-dimethyl-9-(2,6,6-trimethylcyclohexen-1-yl)-4,5-ditritionona-2,4,6,8-tetraenoic acid | AC1OC7KP; Retinoic-11,12-t2 acid; 11,12-3H-Retinoic acid |
| 6913131 | (2Z,4E,6Z,8E)-3,7-dimethyl-9-(2,6,6-trimethylcyclohexen-1-yl)-5,6-ditritionona-2,4,6,8-tetraenoic acid | AC1OC7KA; Retinoic-10,11-t2 acid; all-trans-(10,11-3H2)-Retinoic acid |
| 6439661 | (2Z,4E,6Z,8E)-3,7-dimethyl-9-(2,6,6-trimethylcyclohexen-1-yl)nona-2,4,6,8-tetraenoic acid | |
| 134262 | 3,7-dimethyl-9-(2,6,6-trimethylcyclohexen-1-yl)nona-2,4,6,8-tetraenoic acid | SHGAZHPCJJPHSC-SPLUINJESA-N; FDEFF7D13961B766 CC9FE8A740623243 |
| 56684147 | (2E,6Z,8E)-3,7-dimethyl-9-(2,6,6-trimethylcyclohexen-1-yl)nona-2,6,8-trienoic acid | |
| 54219808 | 3,6,7-trimethyl-9-(2,6,6-trimethylcyclohexen-1-yl)nona-2,4,6,8-tetraenoic acid | |
| 53936974 | 3,7-dimethyl-9-(2,6,6-trimethylcyclohexen-1-yl)nona-2,6,8-trienoic acid | |
| 53740187 | 3,7-dimethyl-9-(2,6,6-trimethylcyclohexen-1-yl)nona-2,4,6-trienoic acid | |
| 44725022 | (Z)-3-[(E)-2-(2,6,6-trimethylcyclohexen-1-yl)ethenyl]hept-2-enoic acid | AC1Q2V68; (2Z)-3-[(E)-2-(2,6,6-trimethylcyclohex-1-en-1-yl)ethenyl]hept-2-enoic acid |
| 21590819 | (2Z,4E,8E)-3-methyl-7-methylidene-9-(2,6,6-trimethylcyclohexen-1-yl)nona-2,4,8-trienoic acid | CHEMBL182393 |
| 11738545 | (2E,4E,6E,8E)-3,7-dimethyl-9-(2,6,6-trimethylcyclohexen-1-yl)deca-2,4,6,8-tetraenoic acid | |
| 10518336 | (2E,4E,8E)-3-methyl-7-methylidene-9-(2,6,6-trimethylcyclohexen-1-yl)nona-2,4,8-trienoic acid | CHEMBL426963 |
| 10380944 | (2E,4E,6Z,8E)-3-ethyl-7-methyl-9-(2,6,6-trimethylcyclohexen-1-yl)nona-2,4,6,8-tetraenoic acid | |
| 10335106 | (2E,4E,6E)-3,7-dimethyl-9-(2,6,6-trimethylcyclohexen-1-yl)nona-2,4,6-trienoic acid | CHEMBL487208 |
| 10286439 | (2E,4E,6Z,8E)-7-ethyl-3-methyl-9-(2,6,6-trimethylcyclohexen-1-yl)nona-2,4,6,8-tetraenoic acid | |
| 10149682 | (2E,4E,6Z,8E)-3,6,7-trimethyl-9-(2,6,6-trimethylcyclohexen-1-yl)nona-2,4,6,8-tetraenoic acid | |
| 10041353 | (2E,4E,6E,8E)-3-ethyl-7-methyl-9-(2,6,6-trimethylcyclohexen-1-yl)nona-2,4,6,8-tetraenoic acid | |
| 6439749 | (2E,4E,6E,8E)-9-(2-ethyl-6,6-dimethylcyclohexen-1-yl)-3,7-dimethylnona-2,4,6,8-tetraenoic acid | SRI 2712-24; 2,4,6,8-Nonatetracenoic acid, AC1NUZ8L |
| 5496917 | (2E,4Z,6E)-3,7-dimethyl-9-(2,6,6-trimethylcyclohexen-1-yl)nona-2,4,6-trienoic acid | |
| 5326825 | (2Z,4Z,6E)-3,7-dimethyl-9-(2,6,6-trimethylcyclohexen-1-yl)nona-2,4,6-trienoic acid | AC1NS159 |
| 4136524 | 3-[2-(2,6,6-trimethylcyclohexen-1-yl)ethenyl]hept-2-enoic acid | AC1N4YDA |
| 135317 | 9-(2-ethyl-6,6-dimethylcyclohexen-1-yl)-3,7-dimethylnona-2,4,6,8-tetraenoic acid | |
| 54525370 | 13-(2,6,6-trimethylcyclohexen-1-yl)trideca-2,4,6,8,10,12-hexaenoic acid | |
| 54472611 | 4,7-dimethyl-9-(2,6,6-trimethylcyclohexen-1-yl)nona-2,4,6,8-tetraenoic acid | |
| 54398880 | 3-methyl-5-[2-[2-(2,6,6-trimethylcyclohexen-1-yl)ethenyl]cyclopenten-1-yl]penta-2,4-dienoic acid | |
| 54044750 | 11-(2,6,6-trimethylcyclohexen-1-yl)undeca-2,4,6,8,10-pentaenoic acid | |
| 53876852 | 3,7-dimethyl-9-(2,4,6,6-tetramethylcyclohexen-1-yl)nona-2,4,6,8-tetraenoic acid | |
| 53790569 | 9-(2,6,6-trimethylcyclohexen-1-yl)nona-2,4,6,8-tetraenoic acid | |
| 53743104 | 5,9-dimethyl-11-(2,6,6-trimethylcyclohexen-1-yl)undeca-2,4,6,8,10-pentaenoic acid | |
| 44579060 | (2E,4E,6Z,8E)-9-(2-butyl-6,6-dimethylcyclohexen-1-yl)-3,7-dimethylnona-2,4,6,8-tetraenoic acid | CHEMBL518436 |
| 44393163 | (2Z,4E,8E)-7-methylidene-9-(2,6,6-trimethylcyclohexen-1-yl)nona-2,4,8-trienoic acid | |

TABLE 2-continued

Exemplary Retinoic Acid Compounds

| CID | IUPAC | Other names |
|---|---|---|
| 25141345 | (2E,4E,6E,8E)-9-(2-butyl-6,6-dimethylcyclohexen-1-yl)-3,7-dimethylnona-2,4,6,8-tetraenoic acid | |
| 19609253 | (2E,4E)-3-methyl-5-[2-[(E)-2-(2,6,6-trimethylcyclohexen-1-yl)ethenyl]cyclopenten-1-yl]penta-2,4-dienoic acid | |
| 14731990 | (2E,4E,6E,8E)-7-methyl-9-(2,6,6-trimethylcyclohexen-1-yl)nona-2,4,6,8-tetraenoic acid | |
| 11141121 | (2E,4E,6E,8E)-4,7-dimethyl-9-(2,6,6-trimethylcyclohexen-1-yl)nona-2,4,6,8-tetraenoic acid | |
| 10712359 | (2E,4E,6Z)-3-methyl-7-[(E)-2-(2,6,6-trimethylcyclohexen-1-yl)ethenyl]undeca-2,4,6-trienoic acid | |
| 10474100 | (2E,4E,6E,8E,10E,12E)-3,7,11-trimethyl-13-(2,6,6-trimethylcyclohexen-1-yl)trideca-2,4,6,8,10,12-hexanoic acid | |
| 10426543 | (E,4E)-3-methyl-4-[3-[(E)-2-(2,6,6-trimethylcyclohexen-1-yl)ethenyl]cyclohex-2-en-1-ylidene]but-2-enoic acid | |
| 10358907 | (Z,4E)-3-methyl-4-[(4E)-3-methyl-4-[(2,6,6-trimethylcyclohexen-1-yl)methylidene]cyclohexa-2,5-dien-1-yl)methylidene) | |
| 10314319 | (2E,4E,6E,8E,10E)-5,9-dimethyl-11-(2,6,6-trimethylcyclohexen-1-yl)undeca-2,4,6,8,10-pentaenoic acid | CHEMBL225948 |
| 10286753 | (2E,4E,6Z,8E)-7-tert-butyl-3-methyl-9-(2,6,6-trimethylcyclohexen-1-yl)nona-2,4,6,8-tetraenoic acid | |
| 10266931 | (2E,4E,6Z)-3-methyl-7-[(E)-2-(2,6,6-trimethylcyclohexen-1-yl)ethenyl]deca-2,4,6-trienoic acid | CHEMBL507779 |
| 10125803 | (2E,4E,6Z)-3-methyl-7-[(E)-2-(2,6,6-trimethylcyclohexen-1-yl)ethenyl]deca-2,4,6-trienoic acid | |
| 10087786 | (Z,4E)-3-methyl-4-[3-[(E)-2-(2,6,6-trimethylcyclohexen-1-yl)ethenyl]cyclohex-2-en-1-ylidene]but-2-enoic acid | |
| 10015486 | (2E,4E,6E)-5-methyl-7-(2,6,6-trimethylcyclohexen-1-yl)hepta-2,4,6-trienoic acid | |
| 9929074 | (2E,4E,6E,8E)-3,7-dimethyl-9-(2,6,6-trimethylcyclohexen-1-yl)nona-2,4,6,8-tetraenoic acid | |
| 9860303 | (2E,4E,6E,8E)-9-(2,6,6-trimethylcyclohexen-1-yl)nona-2,4,6,8-tetraenoic acid | |
| 5355027 | (2E,4E)-3-methyl-5-(2,6,6-trimethylcyclohexen-1-yl)penta-2,4-dienoic acid | C15 acid; AC1NS6O9; NSC23978 |
| 167095 | 3-methyl-5-(2,6,6-trimethylcyclohexen-1-yl)penta-2,4-dienoic acid | AC1L4ZB4 |
| 56606832 | 3,7-dimethyl-9-(9,9,11-trimethylspiro[2.5]oct-10-en-10-yl)nona-2,4,6,8-tetraenoic acid | |
| 54548815 | 3,7,11,11-tetramethyldodeca-2,4-dienoic acid | |
| 54515105 | 7-methyl-3-[2-(2,6,6-trimethylcyclohexen-1-yl)ethenyl]nona-2,5-dienoic acid | YLWKTERFWUXEBW-UHFFFAOYSA-N; 005B26AC36D10A0C9DB5EF006864943F |
| 54358950 | 3-methyl-5-[2-[2-(2,6,6-trimethylcyclohexen-1-yl)ethenyl]cyclohepten-1-yl]penta-2,4-dienoic acid | |
| 54353726 | 3,7,11,11-tetramethyltrideca-2,4-dienoic acid | |
| 54193713 | 3-methyl-5-[2-[2-(2,6,6-trimethylcyclohexen-1-yl)ethenyl]cycloocten-1-yl]penta-2,4-dienoic acid | |
| 53946778 | 2,3,7-trimethyl-9-(2,6,6-trimethylcyclohexen-1-yl)nona-2,4,6,8-tetraenoic acid | |
| 53944823 | 9-(6,6-dimethylcyclohexen-1-yl)-3,7-dimethylnona-2,4,6,8-tetraenoic acid | JAIGDKSXLVOFMH-UHFFFAOYSA-N; F42136BEED6C5A3745B9BA23356D7830 |
| 53921377 | 3-methyl-5-[2-[2-(2,6,6-trimethylcyclohexen-1-yl)ethenyl]cyclohexen-1-yl]penta-2,4-dienoic acid | |
| 44579100 | (2E,4E,6Z,8E)-9-[6,6-dimethyl-2-(2-methylpropyl)cyclohexen-1-yl]-3,7-dimethylnona-2,4,6,8-tetraenoic acid | CHEMBL476773 |
| 44579056 | (2E,4E,6E,8E)-9-[6,6-dimethyl-2-(2-methylpropyl)cyclohexen-1-yl]-3,7-dimethylnona-2,4,6,8-tetraenoic acid | CHEMBL476348 |
| 44314230 | (2Z,5E)-7-methyl-3-[(E)-2-(2,6,6-trimethylcyclohexen-1-yl)ethenyl]nona-2,5-dienoic acid | CHEMBL75548; CHEBI: 220121 |
| 25011742 | (2E,8E)-3,7-dimethyl-9-(2,6,6-trimethylcyclohexen-1-yl)nona-2,8-dienoic acid | |
| 22646220 | (2E,4E,6E,8E)-2,3-dimethyl-9-(2,6,6-trimethylcyclohexen-1-yl)nona-2,4,6,8-tetraenoic acid | |
| 20830941 | (2E,4E,6E,8E)-2,3-dimethyl-9-(2,6,6-trimethylcyclohexen-1-yl)nona-2,4,6,8-tetraenoic acid | |
| 19609240 | (2E,4E)-3-methyl-5-[(1Z)-2-[(E)-2-(2,6,6-trimethylcyclohexen-1-yl)ethenyl]cycloocten-1-yl]penta-2,4-dienoic acid | |
| 18977383 | (2E,4E,6E,8E)-3,7-dimethyl-9-(2,5,6,6-tetramethylcyclohexen-1-yl)nona-2,4,6,8-tetraenoic acid | |
| 15125883 | (2Z,4E,6E,8E)-2,3,7-trimethyl-9-(2,6,6-trimethylcyclohexen-1-yl)nona-2,4,6,8-tetraenoic acid | |

TABLE 2-continued

Exemplary Retinoic Acid Compounds

| CID | IUPAC | Other names |
|---|---|---|
| 15125882 | (2E,4E,6E,8E)-2,3,7-trimethyl-9-(2,6,6-trimethylcyclohexen-1-yl)nona-2,4,6,8-tetraenoic acid | CHEMBL153895; 14-methyl-all-trans-retinoic acid; LMPR01090034 |
| 11266097 | (2Z,4E,8E)-3-methyl-9-(2,6,6-trimethylcyclohexen-1-yl)nona-2,4,8-trien-6-ynoic acid | |
| 11000660 | (2E,4E,6Z,8E)-9-(6,6-dimethylcyclohexen-1-yl)-3,7-dimethylnona-2,4,6,8-tetraenoic acid | |
| 10733921 | (2E,4E,6Z)-7-(8,8-dimethyl-4,5,6,7-tetrahydro-3H-naphthalen-2-yl)-3-methylocta-2,4,6-trienoic acid | |
| 10636975 | (2E,4E,6E,8E)-9-(6,6-dimethylcyclohexen-1-yl)-3,7-dimethylnona-2,4,6,8-tetraenoic acid | |
| 10591236 | (2E,4E,6Z)-7-(4a,8-dimethyl-4,5,6,7-tetrahydro-3H-naphthalen-2-yl)-3-methylocta-2,4,6-trienoic acid | |
| 10404132 | (Z,4E)-3-methyl-4-[(4E)-3-methyl-4-[(2,6,6-trimethylcyclohexen-1-yl)methylidene]cyclohex-2-en-1-ylidene]but-2-enoic acid | |
| 10314318 | (E,4E)-3-methyl-4-[(4E)-3-methyl-4-[(2,6,6-trimethylcyclohexen-1-yl)methylidene]cyclohex-2-en-1-ylidene]but-2-enoic acid | |
| 10215224 | (2E,4E,6Z,8E)-3-methyl-7-propan-2-yl-9-(2,6,6-trimethylcyclohexen-1-yl)nona-2,4,6,8-tetraenoic acid | |
| 10193246 | (2E,4E)-3-methyl-6-[1-[(E)-2-(2,6,6-trimethylcyclohexen-1-yl)ethenyl]cyclopropyl]hexa-2,4-dienoic acid | |
| 9841547 | (2E,4E)-3-methyl-5-[2-[(E)-2-(2,6,6-trimethylcyclohexen-1-yl)ethenyl]cyclohepten-1-yl]penta-2,4-dienoic acid | |
| 9830767 | (2Z,4E,6Z,8E)-9-(6,6-dimethylcyclohexen-1-yl)-3,7-dimethylnona-2,4,6,8-tetraenoic acid | |
| 9819335 | (2E,4E)-3-methyl-5-[2-[(E)-2-(2,6,6-trimethylcyclohexen-1-yl)ethenyl]cyclohexen-1-yl]penta-2,4-dienoic acid | Ro 25-6603; 173792-73-9 |
| 56667667 | (2E,4E,6Z,8E)-3,7-dimethyl-9-(6-methyl-3-prop-1-en-2-ylcyclohexen-1-yl)nona-2,4,6,8-tetraenoic acid | CHEMBL455993; CHEMBL455994 |
| 54758572 | (2Z,4E,6Z,8E)-3,7-dimethyl-9-(2,6,6-trimethylcyclohexen-1-yl)nona-2,4,6,8-tetraenoate | 9-cis-Retinoate; CPD-13549 |
| 54426679 | 2,7-dimethyl-9-(2,6,6-trimethylcyclohexen-1-yl)nona-2,4,6,8-tetraenoic acid | |
| 54325149 | 6-chloro-3,7-dimethyl-9-(2,6,6-trimethylcyclohexen-1-yl)nona-2,4,6,8-tetraenoic acid | |
| 53702687 | 6-iodo-3,7-dimethyl-9-(2,6,6-trimethylcyclohexen-1-yl)nona-2,4,6,8-tetraenoic acid | |
| 29986894 | (2E,4Z,6E,8E)-3,7-dimethyl-9-(2,6,6-trimethylcyclohexen-1-yl)nona-2,4,6,8-tetraenoate | ZINC22066351 |
| 29927144 | (2E,4E,6E,8Z)-3,7-dimethyl-9-(2,6,6-trimethylcyclohexen-1-yl)nona-2,4,6,8-tetraenoate | ZINC21992287 |
| 24916820 | (2E,4E,6E)-3,7-dimethyl-9-(2,6,6-trimethylcyclohexen-1-yl)nona-2,4,6-trienoate | 2g78 |
| 24771817 | 3,7-dimethyl-9-(2,6,6-trimethylcyclohexen-1-yl)nona-2,4,6,8-tetraenoate | CHEBI: 15036 |
| 21917290 | (2E,4E,6E,8E)-9-(5-tert-butyl-2,6,6-trimethylcyclohexen-1-yl)-3,7-dimethylnona-2,4,6,8-tetraenoic acid | |
| 19609245 | (2E,4E,6E,8E)-6-chloro-3,7-dimethyl-9-(2,6,6-trimethylcyclohexen-1-yl)nona-2,4,6,8-tetraenoic acid | |
| 19609224 | (2E,4E,6E,8E)-6-iodo-3,7-dimethyl-9-(2,6,6-trimethylcyclohexen-1-yl)nona-2,4,6,8-tetraenoic acid | |
| 10924150 | (2E,4E,6Z,8E)-9-(2,6-dimethylcyclohexen-1-yl)-3,7-dimethylnona-2,4,6,8-tetraenoic acid | |
| 10613228 | (2E,4E,6E,8E)-9-(2,6-dimethylcyclohexen-1-yl)-3,7-dimethylnona-2,4,6,8-tetraenoic acid | |
| 10469989 | (2E,6Z,8E)-3,7-dimethyl-9-(2,6,6-trimethylcyclohexen-1-yl)nona-2,6,8-trien-4-ynoic acid | |
| 10334998 | (2E,4E)-3-methyl-5-[2-[(E)-2-(2,6,6-trimethylcyclohexen-1-yl)ethenyl]cyclopropyl]penta-2,4-dienoic acid | |
| 9904356 | (2Z,4E,6Z)-3,7-dimethyl-9-(2,6,6-trimethylcyclohexen-1-yl)nona-2,4,6-trien-8-ynoic acid | |
| 7364357 | (2E,4E,6Z,8E)-3,7-dimethyl-9-(2,6,6-trimethylcyclohexen-1-yl)nona-2,4,6,8-tetraenoate | AC1OKKW8; ZINC12661824; 13-cis-retinoate; ZINC03792789 |
| 7048538 | (2Z,4E,6E,8E)-3,7-dimethyl-9-(2,6,6-trimethylcyclohexen-1-yl)nona-2,4,6,8-tetraenoate | |
| 6440565 | 2E,4E,6E)-3,7-dimethyl-9-(2,6,6-trimethylcyclohexen-1-yl)nona-2,4,6-trien-8-ynoic acid | 7,8-Dehydroretinoic acid; 7,8-Didehydroretinoic acid |
| 6419707 | (2E,4E,6E,8E)-3,7-dimethyl-9-(2,6,6-trimethylcyclohexen-1-yl)nona-2,4,6,8-tetraenoate | Retinoate; all-trans-Retinoate; Tretinoine |
| 5771658 | (Z)-3-(2,6,6-trimethylcyclohexen-1-yl)prop-2-enoic acid | NSC-202789; AC1NY9IQ; NCGC00014560 |

TABLE 2-continued

Exemplary Retinoic Acid Compounds

| CID | IUPAC | Other names |
|---|---|---|
| 5383969 | (E)-3-(2,6,6-trimethylcyclohexen-1-yl)prop-2-enoic acid | NSC202789; NSC-20278 |
| 5353358 | (2Z,4E)-3-methyl-6-(2,7,7-trimethyl-3-methylidene-1,4,5,6-tetrahydroinden-2-yl)hexa-2,4-dienoic acid | AC1NS43Q |
| 5289278 | (2E,4E)-3-methyl-6-[(2R)-2,7,7-trimethyl-3-methylidene-1,4,5,6-tetrahydroinden-2-yl]hexa-2,4-dienoic acid | NSC202789; 3-(2,6,6-trimethyl-1-cyclohexen-1-yl)acrylic acid; AC1L77HZ |
| 305742 | 3-(2,6,6-trimethylcyclohexen-1-yl)prop-2-enoic acid | NSC202789; 3-(2,6,6-trimethyl-1-cyclohexen-1-yl)acrylic acid; AC1L77HZ |
| 1851 | 3-methyl-6-(2,7,7-trimethyl-3-methylidene-1,4,5,6-tetrahydroinden-2-yl)hexa-2,4-dienoic acid | AC1L1CDO |
| 54399542 | 6-bromo-3,7-dimethyl-9-(2,6,6-trimethylcyclohexen-1-yl)nona-2,4,6,8-tetraenoic acid | |
| 54233476 | 3,7-dimethyl-5-oxo-9-(2,6,6-trimethylcyclohexen-1-yl)nona-2,6,8-trienoic acid | |
| 54033110 | 2,5,9-trimethyl-11-(2,6,6-trimethylcyclohexen-1-yl)undeca-2,4,6,8,10-pentaenoic acid | |
| 53936708 | 3-methyl-5-[2-[2-(2,6,6-trimethylcyclohexen-1-yl)ethynyl]cyclopenten-1-yl]penta-2,4-dienoic acid | |
| 44314320 | (2Z,4E)-3-methyl-5-[2-[(E)-2-(3,3,6,6-tetramethylcyclohexen-1-yl)ethenyl]cyclopropyl]penta-2,4-dienoic acid | CHEMBL73973; CHEBI: 220303 |
| 44314319 | (2E,4E)-3-methyl-5-[2-[(E)-2-(3,3,6,6-tetramethylcyclohexen-1-yl)ethenyl]cyclopropyl]penta-2,4-dienoic acid | CHEMBL74331; CHEBI: 220301 |
| 22373193 | (2E,4E)-3-methyl-5-[2-[2-(2,6,6-trimethylcyclohexen-1-yl)ethynyl]cyclopenten-1-yl]penta-2,4-dienoic acid | |
| 21145248 | (2Z,4E,6E,8E)-3,7-dimethyl-9-(2,6,6-trimethylcyclohexen-1-yl)nona-2,4,6,8-tetraenoic acid | |
| 20151571 | (2E,4E,6E,8E)-3,7-dimethyl-9-(2,6,6-trimethylcyclohexen-1-yl)nona-2,4,6,8-tetraenoic acid | |
| 19609231 | (2E,4E,6E,8E)-6-bromo-3,7-dimethyl-9-(2,6,6-trimethylcyclohexen-1-yl)nona-2,4,6,8-tetraenoic acid | |
| 16727824 | (2E,4E,6Z,8E)-3,7-dimethyl-9-(2,6,6-trimethylcyclohexen-1-yl)nona-2,4,6,8-tetraenoic acid | All-trans-Retinoic acid & 9-cis-Retinoic Acid |
| 11015604 | (2E,4E,6E,8E,10E,12E,14E,16E)-2,6,11,15-tetramethyl-17-(2,6,6-trimethylcyclohexen-1-yl)-3-tritioheptadeca-2,4,6,8-trimethylcyclyhexen-1-yl)-3-tritioheptadeca-2,4,6,8,10,12,14,16-octaenoic acid | |
| 10406618 | (2E,4Z,6E,8E,10E,12E)-2,7,11-trimethyl-13-(2,6,6-trimethylcyclohexen-1-yl)trideca-2,4,6,8,10,12-hexanoic acid | |
| 9976193 | (2E,4E,6E,8E,10E,12E)-2,7,11-trimethyl-13-(2,6,6-trimethylcyclohexen-1-yl)trideca-2,4,6,8,10,12-hexanoic acid | |
| 9843074 | (2E,4E,6E)-3-methyl-7-(4,4,7,7-tetramethyl-2-pentyl-1,3,5,6-tetrahydroinden-2-yl)hepta-2,4,6-trienoic acid | |
| 6439881 | (2Z,4E,6Z,8E)-9-(3,3-difluoro-2,6,6-trimethylcyclohexen-1-yl)-3,7-dimethylnona-2,4,6,8-tetraenoic acid | DFRA; 4,4-Difluororetinoic acid; AC1O5SM |
| 6436320 | (2E,4E,6Z,8E,10E,12E,14E,16E)-2,6,11,15-tetramethyl-17-(2,6,6-trimethylcyclohexen-1-yl)heptadeca-2,4,6,8,10,12,14,16-octaenoic acid | AC1O5LFK; beta-apo-8'-Carotenoic acid; 8'-Apo-beta,psi-carotenoic acid |
| 5387557 | (2Z)-2-[5-(2,6,6-trimethylcyclohexen-1-yl)-3-[(E)-2-(2,6,6-trimethylcyclohexen-1-yl)ethenyl]cyclohexanoic acid | NSC624510; AC1NTSHG; AC1Q5T6Y |
| 5366642 | (2E,4E,6E,8E)-9-(3,3-difluoro-2,6,6-trimethylcyclohexen-1-yl)-3,7-dimethylnona-2,4,6,8-tetraenoic acid | 4,4-Difluororetinoic acid; AC1NSNWF; 4,4-Difluororetinoic acid (all-trans) |
| 361473 | 2-[5-(2,6,6-trimethylcyclohexen-1-yl)-3-[2-(2,6,6-trimethylcyclohexen-1-yl)ethenyl]cyclohex-2-en-1-yl]heptadeca-2,4,6,8,10,12,14,16-octaenoic acid | AC1L7IQC; NCI60_007432; 2-[5-(2,6,6-trimethylcyclohexen-1-yl)-3-[2-(2,6,6-trimethylcyclohexen-1-yl)ethenyl]cyclohex-2-en-1-ylidene]acetic acid |
| 146218 | 9-(3,3-difluoro-2,6,6-trimethylcyclohexen-1-yl)-3,7-dimethylnona-2,4,6,8-tetraenoic acid | |
| 56660872 | (2E,4E,6Z,8E)-3,7-dimethyl-9-(2-methyl-5-prop-1-en-2-ylcyclohexen-1-yl)nona-2,4,6,8-tetraenoic acid | CHEMBL457645; CHEMBL513434 |
| 54587023 | (2E,4E,6Z,8E)-3,7-dimethyl-9-[(3S,6R)-3-methyl-6-prop-1-en-2-ylcyclohexen-1-yl]nona-2,4,6,8-tetraenoic acid | CHEMBL1773351 |

TABLE 2-continued

Exemplary Retinoic Acid Compounds

| CID | IUPAC | Other names |
|---|---|---|
| 54586043 | (2E,4E,6Z)-3-methyl-7-[(3R,6S)-3-methyl-6-propan-2-ylcyclohexen-1-yl]octa-2,4,6-trienoic acid | CHEMBL1773361 |
| 54310202 | 7-ethyl-3,11-dimethyltrideca-2,4-dienoic acid | |
| 54177995 | 8-(3-ethyl-2-propan-2-ylcyclohex-2-en-1-ylidene)-3,7-dimethylocta-2,4,6-trienoic acid | OZUIXDDSOLQKNK-UHFFFAOYSA-N; 982DADEA9DC5579A132BDF2AD7FA647A |
| 54012267 | 3,8,12-trimethyltrideca-2,4-dienoic acid | |
| 53787191 | 3,8,13-trimethyltetradeca-2,4-dienoic acid | |
| 53743194 | 4-methyl-6-(2,6,6-trimethylcyclohexen-1-yl)hex-2-enoic acid | |
| 53710521 | 3,7,13-trimethyltetradeca-2,4-dienoic acid | |
| 53707670 | 3,7-dimethyl-8-(3-methyl-2-propan-2-ylcyclohex-2-en-1-ylidene)octa-2,4,6-trienoic acid | BYHSFJNWVLBCIM-UHFFFAOYSA-N; 14B10A34153F37A66327788679FAC42F |
| 53666154 | 3,7,11-trimethyltrideca-2,4-dienoic acid | |
| 53438161 | 3,7,11-trimethyltetradeca-2,4-dienoic acid | |
| 53427754 | 7,7-dimethylicosa-2,4-dienoic acid | |
| 52952998 | (2E,4E,6Z,8E)-3,7-dimethyl-9-[(3R,6S)-3-methyl-6-prop-1-en-2-ylcyclohexen-1-yl]nona-2,4,6,8-tetraenoic acid | CHEMBL1773352 |
| 44631433 | (2Z,4E)-3-methyl-5-(2,2,4-trimethylcyclohex-3-en-1-yl)penta-2,4-dienoic acid | FZFFLFPGBIXCKI-STRRHFTISA- |
| 44291210 | (2Z,4Z,6Z,8E)-8-(3-ethyl-2-propan-2-ylcyclohex-2-en-1-ylidene)-3,7-dimethylocta-2,4,6-trienoic acid | CHEMBL43954 |
| 44290946 | (2E,4Z,6Z,8E)-8-(3-ethyl-2-propan-2-ylcyclohex-2-en-1-ylidene)-3,7-dimethylocta-2,4,6-trienoic acid | CHEMBL43833; CHEBI: 167938 |
| 24845989 | sodium (2Z,4E,6Z,8E)-3,7-dimethyl-9-(2,6,6-trimethylcyclohexen-1-yl)nona-2,4,6,8-tetraenoate | LS-143475 |
| 23670222 | potassium (2E,4E,6E,8E)-3,7-dimethyl-9-(2,6,6-trimethylcyclohexen-1-yl)nona-2,4,6,8-tetraenoate | |
| 23665641 | sodium (2E,4E,6E,8E)-3,7-dimethyl-9-(2,6,6-trimethylcyclohexen-1-yl)nona-2,4,6,8-tetraenoate | Sodium retinoate; Retinoic acid, sodium salt; Vitamin A acid sodium sal |
| 23265304 | (2E,4E)-3-methyl-5-(2,2,4-trimethylcyclohex-3-en-1-yl)penta-2,4-dienoic acid | |
| 21437585 | (2E,4E)-3,8,12-trimethyltrideca-2,4-dienoic acid | |
| 21437539 | (2E,4E)-3,8,13-trimethyltetradeca-2,4-dienoic acid | |
| 21437504 | (2E,4E)-3,7,13-trimethyltetradeca-2,4-dienoic acid | |
| 21158960 | (2E,4E)-7,7-dimethylicosa-2,4-dienoic acid | |
| 20270951 | (6E,8E)-2,7-dimethyl-9-(2,6,6-trimethylcyclohexen-1-yl)nona-2,3,6,8-tetraenoic acid | |
| 19609232 | (2E,4E)-3-methyl-5-[2-[(E)-2-(2,6,6-trimethylcyclohexen-1-yl)ethenyl]cyclohexen-1-yl]penta-2,4-dienoic acid | |
| 11130378 | (2E,4E,6E,8E)-3,7-dimethyl-9-(2,6,6-trimethylcyclohex-2-en-1-yl)nona-2,4,6,8-tetraenoic acid | |
| 11066537 | (2Z,4E,6E,8E)-3,7-dimethyl-9-(2,6,6-trimethylcyclohex-2-en-1-yl)nona-2,4,6,8-tetraenoic acid | |
| 10470917 | (2Z,4E,6Z,8E)-8-(3-ethyl-2-propan-2-ylcyclohex-2-en-1-ylidene)-3,7-dimethylocta-2,4,6-trienoic acid | |
| 10402558 | (2Z,4E,6E,8E)-3,7-dimethyl-8-(3-methyl-2-propan-2-ylcyclohex-2-en-1-ylidene)octa-2,4,6-trienoic acid | |
| 10357464 | (2E,4E,6Z,8E)-3,7-dimethyl-8-(3-methyl-2-propan-2-ylcyclohex-2-en-1-ylidene)octa-2,4,6-trienoic acid | |
| 10086191 | (2E,4E,6E,8E)-3,7-dimethyl-8-(3-methyl-2-propan-2-ylcyclohex-2-en-1-ylidene)octa-2,4,6-trienoic acid | CHEMBL333032; CHEBI: 299410 |
| 10086189 | (2Z,4E,6Z,8E)-3,7-dimethyl-8-(3-methyl-2-propan-2-ylcyclohex-2-en-1-ylidene)octa-2,4,6-trienoic acid | |
| 9972952 | (2Z,4E,6E,8E)-8-(3-ethyl-2-propan-2-ylcyclohex-2-en-1-ylidene)-3,7-dimethylocta-2,4,6-trienoic acid | CHEMBL44582; CHEBI: 168408 |
| 9972949 | (2E,4E,6Z,8E)-8-(3-ethyl-2-propan-2-ylcyclohex-2-en-1-ylidene)-3,7-dimethylocta-2,4,6-trienoic acid | |
| 9883342 | (2E,4E,6E,8E)-8-(3-ethyl-2-propan-2-ylcyclohex-2-en-1-ylidene)-3,7-dimethylocta-2,4,6-trienoic acid | CHEMBL46398; CHEBI: 168441 |
| 5372326 | (E)-3-methyl-5-(2,6,6-trimethylcyclohexen-1-yl)pent-2-enoic acid | AC1NSY3I; 2-Pentenoic acid, 3-methyl-5-(2,6,6-trimethyl-1-cyclohexenyl); (E)-3-methyl-5-(2,6,6-trimethylcyclohexen-1-yl)pent-2-enoic acid |
| 445560 | (2E,4E,6Z,8E)-3,7-dimethyl-9-(2,6,6-trimethylcyclohex-2-en-1-yl)nona-2,4,6,8-tetraenoic acid | AC1L9I79 |

TABLE 2-continued

Exemplary Retinoic Acid Compounds

| CID | IUPAC | Other names |
|---|---|---|
| 56667221 | (2E,4E,6Z,8E)-3,7-dimethyl-9-(3-methyl-6-propan-2-ylcyclohexen-1-yl)nona-2,4,6,8-tetraenoic acid | CHEMBL508378 |
| 54585066 | (2E,4E,6Z,8E)-3,7-dimethyl-9-[(1S,4R,5R)-4,6,6-trimethyl-3-bicyclo[3.1.1]hept-2-enyl]nona-2,4,6,8-tetraenoic acid | CHEMBL1773358 |
| 54585064 | (2E,4E,6Z,8E)-3,7-dimethyl-9-[(3R)-3-methyl-6-propan-2-ylidenecyclohexen-1-yl]nona-2,4,6,8-tetraenoic acid | CHEMBL1773355 |
| 54582176 | (2E,4E,6Z,8E)-3,7-dimethyl-9-[(3S)-3-methyl-6-propan-2-ylidenecyclohexen-1-yl]nona-2,4,6,8-tetraenoic acid | CHEMBL1773354 |
| 54581148 | (2E,4E,6Z,8E)-3,7-dimethyl-9-[(1R,2R,5S)-2-methyl-5-propan-2-yl-3-bicyclo[3.1.0]hex-3-enyl]nona-2,4,6,8-tetraenoic acid | CHEMBL1773360 |
| 54542310 | 3,4,4-trimethyltetradec-2-enoic acid | |
| 54521054 | 3,4,4-trimethyloctadec-2-enoic acid | |
| 54518673 | 3,7-dimethyl-9-(2,6,6-trimethyl-5-oxocyclohexen-1-yl)nona-2,4,6,8-tetraenoic acid | |
| 54348687 | 3,7,10,11-tetramethyldodeca-2,4-dienoic acid | |
| 54325421 | 3,4,4-trimethylheptadec-2-enoic acid | |
| 54316493 | 3,4,4-trimethylpentadec-2-enoic acid | |
| 54305044 | 2-ethyl-3,7-dimethyl-9-(2,6,6-trimethylcyclohexen-1-yl)nona-2,4,6,8-tetraenoic acid | |
| 54265680 | 3,7,11,15-tetramethylhexadeca-2,4-dienoic acid | |
| 54194359 | 3,7-dimethyl-9-(2,6,6-trimethyl-4-oxocyclohexen-1-yl)nona-2,4,6,8-tetraenoic acid | |
| 54170467 | 3,7,11,15-tetramethylhexadeca-2,4,6,14-tetraenoic acid | |
| 54167172 | 3,4,4-trimethylhexadec-2-enoic acid | |
| 54105865 | 3,7,7,11,11-pentamethyldodec-2-enoic acid | |
| 54064253 | 2-ethyl-5,9-dimethyl-3-(2,6,6-trimethylcyclohexen-1-yl)undeca-2,4,6,8,10-pentaenoic acid | |
| 53961371 | 3,7,11-trimethyldodeca-2,4,11-trienoic acid | |
| 53936602 | 9-[5-(2-cyclohexylethyl)-2,6,6-trimethylcyclohexen-1-yl]-3,7-dimethylnona-2,4,6,8-tetraenoic acid | |
| 53825233 | 3,7,11,15,19-pentamethylicosa-2,4,6,10,18-pentaenoic acid | |
| 53801569 | 3-methyl-5-[2-[2-(2,6,6-trimethylcyclohexen-1-yl)ethynyl]cyclohepten-1-yl]penta-2,4-dienoic acid | |
| 53725805 | 3,7-dimethyldodeca-2,4-dienoic acid | |
| 53700416 | 3,7,11,15-tetramethylhexadeca-2,4,6-trienoic acid | |
| 52953080 | (2E,4E,6Z,8E)-3,7-dimethyl-9-[(3S,6R)-3-methyl-6-propan-2-ylcyclohexen-1-yl]nona-2,4,6,8-tetraenoic acid | CHEMBL1773353 |
| 52952997 | (2E,4E,6Z,8E)-3,7-dimethyl-9-[(1R,4S,5S)-4,6,6-trimethyl-3-bicyclo[3.1.1]hept-2-enyl]nona-2,4,6,8-tetraenoic acid | CHEMBL1773357 |
| 52921782 | (2E,5R,10E,12E)-3,5,15-trimethyl-7-methylidenehexadeca-2,10,12-trienoic acid | LMFA01020367; 16:3(2E,10E,12E)(3Me,5Me[R],7My,15Me) |
| 46178652 | (2E,4E)-5-[(1R)-2,2-dimethyl-6-methylidenecyclohexyl]-3-methylpenta-2,4-dienoic acid | |
| 44579059 | (2E,4E,6Z,8E)-3,7-dimethyl-9-(2,2,6-trimethylcyclohexyl)nona-2,4,6,8-tetraenoic acid | CHEMBL451158 |
| 25147656 | (2E,4E,6Z,8E)-3,7-dimethyl-9-[(3R,6S)-3-methyl-6-propan-2-ylcyclohexen-1-yl]nona-2,4,6,8-tetraenoic acid | CHEMBL508378 |
| 22168242 | (2E,4E,6E,10E)-3,7,11,15,19-pentamethylicosa-2,4,6,10,18-pentaenoic acid | |
| 22168239 | (2E,4E,6E)-3,7,11,15-tetramethylhexadeca-2,4,6-trienoic acid | |
| 22168234 | (2E,4E,6E)-3,7,11,15-tetramethylhexadeca-2,4,6,14-tetraenoic acid | |
| 21764469 | (2E,4E)-3-methyl-5-[(1R)-2,6,6-trimethylcyclohex-2-en-1-yl]penta-2,4-dienoic acid | |
| 21650797 | acetyl (2E,4E,6E,8E)-3,7-dimethyl-9-(2,6,6-trimethylcyclohexen-1-yl)nona-2,4,6,8-tetraeneperoxoate | |
| 21525820 | (2E,4E)-7,11,11-trimethyldodeca-2,4-dienoic acid | |
| 21525806 | (2E,4E)-3,7-dimethyldodeca-2,4-dienoic acid | |
| 21291068 | (E)-3,4,4-trimethylhexadec-2-enoic acid | |
| 21291063 | (E)-3,4,4-trimethyltetradec-2-enoic acid | |
| 21291060 | (E)-3,4,4-trimethylpentadec-2-enoic acid | |
| 21291047 | (E)-3,4,4-trimethylheptadec-2-enoic acid | |
| 21291045 | (E)-3,4,4-trimethyloctadec-2-enoic acid | |
| 20830940 | (2E,4E,6Z,8E)-3,7-dimethyl-9-(2,5,6,6-tetramethylcyclohexen-1-yl)nona-2,4,6,8-tetraenoate | |
| 20306860 | (2E,4E)-3,7,11-trimethyldodeca-2,4,11-trienoic acid | |
| 20027300 | azanium (2E,4E,6E,8E)-3,7-dimethyl-9-(2,6,6-trimethylcyclohexen-1-yl)nona-2,4,6,8-tetraenoate | |
| 19609235 | (2E,4E)-2-iodo-3-methyl-5-(2,6,6-trimethylcyclohexen-1-yl)penta-2,4-dienoic acid | |
| 19606927 | (2E,4E,6E,8E)-3,7-dimethyl-9-(2,6,6-trimethyl-4-oxocyclohexen-1-yl)nona-2,4,6,8-tetraenoic acid | |
| 18977382 | (2E,4E,6E,8E)-3,7-dimethyl-9-(2,5,6,6-tetramethylcyclohexen-1-yl)nona-2,4,6,8-tetraenoate | |

TABLE 2-continued

Exemplary Retinoic Acid Compounds

| CID | IUPAC | Other names |
|---|---|---|
| 16061319 | (2Z,4E,6Z,8E)-7-(hydroxymethyl)-3-methyl-9-(2,6,6-trimethylcyclohexen-1-yl)nona-2,4,6,8-tetraenoic acid | 19-Hydroxy-13-cis-retinoic acid; LMPR01090029 |
| 16061318 | (2E,4E,6Z,8E)-7-(hydroxymethyl)-3-methyl-9-(2,6,6-trimethylcyclohexen-1-yl)nona-2,4,6,8-tetraenoic acid | 19-Hydroxy-all-trans-retinoic acid; LMPR01090028 |
| 15125888 | (2E,4E,6E,8E)-2-ethyl-3,7-dimethyl-9-(2,6,6-trimethylcyclohexen-1-yl)nona-2,4,6,8-tetraenoic acid | CHEMBL154239 |
| 11747707 | (2E,4E,6Z,8E)-3,7-dimethyl-9-(6-methylcyclohexen-1-yl)nona-2,4,6,8-tetraenoic acid | |
| 11602784 | (2E,4E)-3-methyl-5-[2-[2-(2,6,6-trimethylcyclohexen-1-yl)ethynyl]cyclohepten-1-yl]penta-2,4-dienoic acid | |
| 10516342 | (2E,4E,6E,8E)-3,7-dimethyl-9-(6-methylcyclohexen-1-yl)nona-2,4,6,8-tetraenoic acid | |
| 10354668 | (Z,4E)-4-(3-ethyl-2-propan-2-ylcyclohex-2-en-1-ylidene)-3-methylbut-2-enoic acid | |
| 10053647 | (2Z,4Z,6E,8E,10E,12E,14E,16E,18E,20E,22E,24E)-2,6,10,14,19,23-hexamethyl-25-(2,6,6-trimethylcyclohexen-1-yl)pentacosa-2,4,6,8,10,12,14,16,18,20,22,24-dodecaenoic acid | |
| 9995780 | (2Z,4E,6E,8E)-3,7-dimethyl-9-(2,6,6-trimethyl-5-oxocyclohexen-1-yl)nona-2,4,6,8-tetraenoic acid | Oxo-13-cis-retinoate; 4-keto-13-cis-retinoate |
| 9949957 | (2E,4E,6E,8E)-3,7-dimethyl-8-[3-(2-methylpropyl)-2-propan-2-ylcyclohex-2-en-1-ylidene]octa-2,4,6-trienoic acid | |
| 9948768 | (2E,4E,6Z,8E)-3,7-dimethyl-9-(2,6,6-trimethyl-5-oxocyclohexen-1-yl)nona-2,4,6,8-tetraenoic acid | |
| 9829386 | (2E,4Z,6E,8E,10E,12E,14E,16E,18E,20E,22E,24E)-2,6,10,14,19,23-hexamethyl-25-(2,6,6-trimethylcyclohexen-1-yl)pentacosa-2,4,6,8,10,12,14,16,18,20,22,24-dodecaenoic acid | |
| 6477090 | (2Z,4Z,6Z,8E,10Z,12Z,14E,16Z,18Z,20E,22Z,24E)-2,6,10,14,19,23-hexamethyl-25-(2,6,6-trimethylcyclohexen-1-yl)pentacosa-2,4,6,8,10,12,14,16,18,20,22,24-dodecaenoic acid | AC1O53P5; 3',4'-Didehydro-,.psi.-caroten-16'-oic acid |
| 6439734 | (2Z,4E,6Z,8E)-3,7-dimethyl-9-(2,2,6-trimethylcyclohexyl)nona-2,4,6,8-tetraenoic acid | 7,8-Dihydroretinoic acid |
| 6437018 | (2Z,4E)-3,7,11-trimethyldodeca-2,4-dienoic acid | AC1O5MUO; EINECS 258-354-9 |
| 6437016 | (2E,4E)-3,7,11-trimethyldodeca-2,4-dienoic acid | AC1O5MUI; CHEMBL37590 |
| 5476505 | (2E,4E)-3-methyl-5-(2,6,6-trimethylcyclohex-2-en-1-yl)penta-2,4-dienoic acid | AC1O5MUI; CHEMBL37590 |
| 5460164 | (2E,4E,6E,8E)-3,7-dimethyl-9-(2,2,6-trimethylcyclohexyl)nona-2,4,6,8-tetraenoic acid | Retinyl ester; all-trans-Retinyl ester |
| 5281248 | (2E,4E,6E,8E,10E,12E,14E,16E,18E,20E,22E,24E)-2,6,10,14,19,23-hexamethyl-25-(2,6,6-trimethylcyclohexanoic acid | NSC635690; Torularhodin; AC1NQY9 |
| 637039 | 2E,4E,6E,8E,10E,12E,14E,16E,18E,20E)-2,6,10,15,19-pentamethyl-21-(2,6,6-trimethylcyclohexen-1-yl)hexanoic acid | Neurosporaxanthin; all-trans-Neurosporaxanthin |
| 428485 | 3-methyl-5-(2,6,6-trimethylcyclohex-2-en-1-yl)penta-2,4-dienoic acid | AC1L8LML; 3-methyl-5-(2,6,6-trimethylcyclohex-2-en-1-yl)penta-2,4-dienoic acid |
| 103723 | 3,7,11-trimethyldodeca-2,4-dienoic acid | |
| 94165 | 2,6,10,14,19,23-hexamethyl-25-(2,6,6-trimethylcyclohexen-1-yl)pentacosa-2,4,6,8,10,12,14,16,18,20,22,24-dodecanenoic acid | AC1L3RN8; NCI60_011910 |
| 56661049 | (2E,4E,6Z,8E)-3,7-dimethyl-9-(4,4,6,6-tetramethyl-2-bicyclo[3.1.1]hept-2-enyl)nona-2,4,6,8-tetraenoic acid | CHEMBL455992 |
| 54581147 | (2E,4E,6Z,8E)-9-[(1S,5R)-6,6-dimethyl-4-bicyclo[3.1.1]hept-3-enyl]-3,7-dimethylnona-2,4,6,8-tetraenoic acid | CHEMBL1773359 |
| 54478024 | 3,4,4-trimethylnon-2-enoic acid | |
| 54476971 | 3,4,4-trimethylundec-2-enoic acid | |
| 54287870 | 3-formyl-7-methyl-9-(2,6,6-trimethylcyclohexen-1-yl)nona-2,4,6,8-tetraenoic acid | RVKZSGIKOAAYJJ-UHFFFAOYSA-N; 293564D2B64FAC5F 524A1B691CBF7C6B |
| 54116397 | 3,7-dimethyl-2-propan-2-yl-9-(2,6,6-trimethylcyclohexen-1-yl)nona-2,4,6,8-tetraenoic acid | NKQIYDSGIYJXSA-UHFFFAOYSA-N; 5597749F477D668D 55E163C44DA1F3EB |
| 54073647 | 3,4,4-trimethyldec-2-enoic acid | |
| 53995964 | 3-methyl-5-[2-[2-(2,6,6-trimethylcyclohexen-1-yl)ethenyl]cyclohexyl]penta-2,4-dienoic acid | |
| 53919798 | 3,4,4-trimethyldodec-2-enoic acid | |
| 53889922 | 3,7-dimethyl-9-(2,4,4,6,6-pentamethyl-3-oxocyclohexen-1-yl)nona-2,4,6,8-tetraenoic acid | |

TABLE 2-continued

Exemplary Retinoic Acid Compounds

| CID | IUPAC | Other names |
|---|---|---|
| 53887460 | 4-(hydroxymethyl)-3,7-dimethyl-9-(2,6,6-trimethylcyclohexen-1-yl)nona-2,4,6,8-tetraenoic acid | |
| 53854796 | 3-methyl-6-(3,3,7,7-tetramethyl-3a,4,5,6-tetrahydroinden-2-ylidene)hexa-2,4-dienoic acid | |
| 53754609 | 2-ethyl-5,9-dimethyl-11-(2,6,6-trimethylcyclohexen-1-yl)undeca-2,4,6,8,10-pentaenoic acid | |
| 50925583 | (2E,4E,6E,8E)-9-[(1R,2R,4aS,8aR)-1,6-dimethyl-2-propyl-4a,5,8,8a-tetrahydro-2H-naphthalen-1-yl]-8-methylnona-2,4,6,8-tetraenoic acid | |
| 45039634 | (2E,4E,6E,8E)-9-[6,6-dimethyl-3-oxo-2-(trideuteriomethyl)cyclohexen-1-yl]-3,7-dimethylnona-2,4,6,8-tetraenoic acid | |
| 21291081 | (E)-3,4,4-trimethyldec-2-enoic acid | |
| 21291044 | (E)-3,4,4-trimethyldodec-2-enoic acid | |
| 21291042 | (E)-3,4,4-trimethylnon-2-enoic acid | |
| 21291032 | (E)-3,4,4-trimethylundec-2-enoic acid | |
| 19384872 | (E)-4-[(2E,4E,6E,8E)-3,7-dimethyl-9-(2,6,6-trimethylcyclohexen-1-yl)nona-2,4,6,8-tetraenoyl]oxy-4-oxobut-2-enoic acid | |
| 16061321 | (2Z,4E,6Z,8E)-7-formyl-3-methyl-9-(2,6,6-trimethylcyclohexen-1-yl)nona-2,4,6,8-tetraenoic acid | 19-Oxo-9-cis-retinoic acid; LMPR01090031 |
| 16061320 | (2E,4E,6Z,8E)-7-formyl-3-methyl-9-(2,6,6-trimethylcyclohexen-1-yl)nona-2,4,6,8-tetraenoic acid | 19-Oxo-all-trans-retinoic acid; LMPR01090030 |
| 15125894 | (2E,4E,6E,8E)-3,7-dimethyl-2-propan-2-yl-9-(2,6,6-trimethylcyclohexen-1-yl)nona-2,4,6,8-tetraenoic acid | CHEMBL153894 |
| 10043037 | (2E,4E,6E,8E)-3,7-dimethyl-9-(2,4,4,6,6-pentamethyl-3-oxocyclohexen-1-yl)nona-2,4,6,8-tetraenoic acid | CHEMBL103068 |
| 9972939 | (2E,4E,6Z,8E)-3,7-dimethyl-9-(2,6,6-trimethyl-3-oxocyclohexen-1-yl)nona-2,4,6,8-tetraenoic acid | |
| 9906064 | (2E,4E)-3-methyl-5-[(1R)-2-[(E)-2-(2,6,6-trimethylcyclohexen-1-yl)ethenyl]cyclohexyl]penta-2,4-dienoic acid | |
| 9902057 | (2Z,4E,6Z,8E)-4-(hydroxymethyl)-3,7-dimethyl-9-(2,6,6-trimethylcyclohexen-1-yl)nona-2,4,6,8-tetraenoic acid | |
| 6437087 | (2Z,4E,6E,8E)-3,7-dimethyl-9-(2,6,6-trimethyl-3-oxocyclohexen-1-yl)nona-2,4,6,8-tetraenoic acid | Oxoretinoic acid; 4-Oxo-isotretinoin |
| 6437063 | (2E,4E,6E,8E)-3,7-dimethyl-9-(2,6,6-trimethyl-3-oxocyclohexen-1-yl)nona-2,4,6,8-tetraenoic acid | 4-Oxoretinoic acid; 4-Ketoretinoic acid |
| 447276 | (2E,4E,6E,8E)-3,7-dimethyl-9-(2,6,6-trimethylcyclohexa-1,3-dien-1-yl)nona-2,4,6,8-tetraenoic acid | Vitamin A2 acid; 3,4-Didehydroretinoic acid |
| 104857 | 3,7-dimethyl-9-(2,6,6-trimethyl-3-oxocyclohexen-1-yl)nona-2,4,6,8-tetraenoic acid | |

Pubchem Compound Identifiers (CIDs) in Table 2 refer to the compound identification number for pubchem.ncbi.nlm.nih.gov

TABLE 3

Additional retinoic acid compounds

| Compound Number | Compound | MMGBSA dG Bind |
|---|---|---|
| 1 | 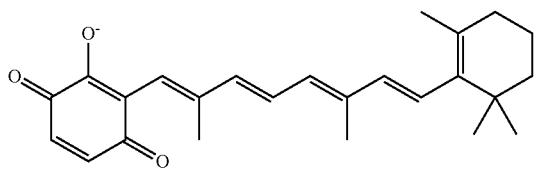 [SMILES: CC1=C(/C=C/C(C)=C/C=C/C(C)=C/C2=C([O-])C(=O)C=CC2=O)C(C)(C)CCC1] | −42.523 |
| 2 | 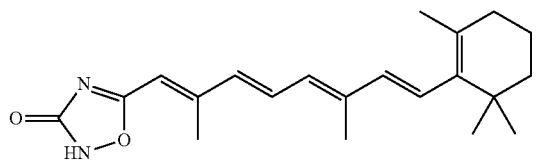 [SMILES: CC1=C(/C=C/C(C)=C/C=C/C(C)=C/c2nc(=O)[nH]o2)C(C)(C)CCC1] | −41.676 |

TABLE 3-continued

Additional retinoic acid compounds

| Compound Number | Compound | MMGBSA dG Bind |
|---|---|---|
| 3 | | −40.719 |
| 4 | | −40.448 |
| 5 | | −40.365 |
| 6 | | −40.345 |
| 7 | | −40.249 |
| 8 | | −39.417 |
| 9 | | −39.232 |
| 10 | | −39.050 |

TABLE 3-continued

Additional retinoic acid compounds

| Compound Number | Compound | MMGBSA dG Bind |
|---|---|---|
| 11 | | −38.984 |
| 12 | | −38.958 |
| 13 | | −38.818 |
| 14 | | −38.817 |
| 15 | | −38.742 |
| 16 | | −38.627 |
| 17 | | −38.309 |
| 18 | | −38.247 |
| 19 | | −38.124 |

TABLE 3-continued

Additional retinoic acid compounds

| Compound Number | Compound | MMGBSA dG Bind |
|---|---|---|
| 20 | | −37.847 |
| 21 | | −37.846 |
| 22 | | −37.804 |
| 23 | | −37.628 |
| 24 | | −37.601 |
| 25 | | −37.585 |
| 26 | | −37.568 |
| 27 | | −37.558 |
| 28 | | −37.542 |

TABLE 3-continued

Additional retinoic acid compounds

| Compound Number | Compound | MMGBSA dG Bind |
|---|---|---|
| 29 | | −37.485 |
| 30 | | −37.460 |
| 31 | | −37.390 |
| 32 | | −37.361 |
| 33 | | −37.135 |
| 34 | | −36.909 |
| 35 | | −36.848 |
| 36 | | −36.903 |
| 37 | | −36.761 |

TABLE 3-continued

Additional retinoic acid compounds

| Compound Number | Compound | MMGBSA dG Bind |
|---|---|---|
| 38 | | −36.718 |
| 39 | | −36.588 |
| 40 | | −36.555 |
| 41 | | −36.527 |
| 42 | | −36.516 |
| 43 | | −36.418 |
| 44 | | −36.392 |
| 45 | | −36.388 |
| 46 | | −36.384 |

TABLE 3-continued

Additional retinoic acid compounds

| Compound Number | Compound | MMGBSA dG Bind |
|---|---|---|
| 47 | | −36.256 |
| 48 | | −36.247 |
| 49 | | −36.061 |
| 50 | | −35.965 |
| 51 | | −35.875 |
| 52 | | −35.849 |
| 53 | | −35.784 |
| 54 | | −35.682 |

TABLE 3-continued

Additional retinoic acid compounds

| Compound Number | Compound | MMGBSA dG Bind |
|---|---|---|
| 55 | | −35.677 |
| 56 | | −35.622 |
| 57 | | −35.513 |
| 58 | | −35.493 |
| 59 | | −35.321 |
| 60 | | −35.277 |
| 61 | | −35.303 |
| 62 | | −35.186 |

TABLE 3-continued
Additional retinoic acid compounds
| Compound Number | Compound | MMGBSA dG Bind |
|---|---|---|
| 63 | 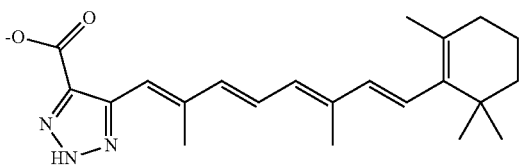 | −35.164 |
| 64 | 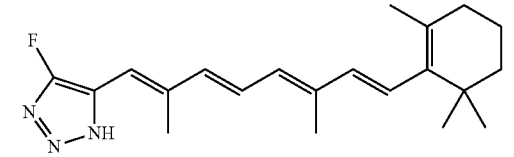 [SMILES: CC1=C(/C=C/C(C)=C/C=C/C(C)=C/c2[nH]nnc2F)C(C)(C)CCC1] | −35.152 |
| 65 | 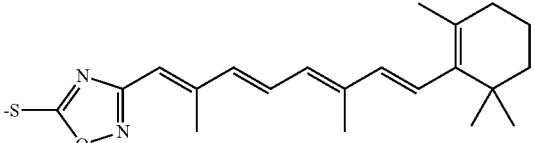 | −35.142 |
| 66 | 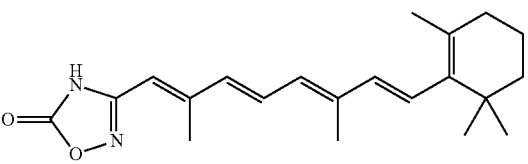 [SMILES: CC1=C(/C=C/C(C)=C/C=C/C(C)=C/c2noc(=O)[nH]2)C(C)(C)CCC1] | −34.986 |
| 67 | 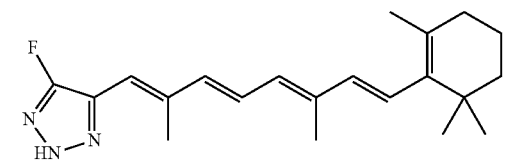 [SMILES: CC1=C(/C=C/C(C)=C/C=C/C(C)=C/c2n[nH]nc2F)C(C)(C)CCC1] | −34.949 |
| 68 | 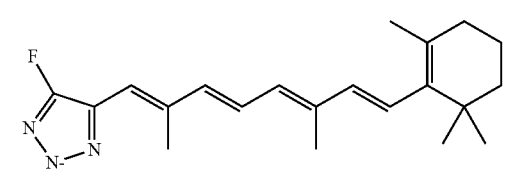 [SMILES: CC1=C(/C=C/C(C)=C/C=C/C(C)=C/c2n[n-]nc2F)C(C)(C)CCC1] | −34.940 |
| 69 | 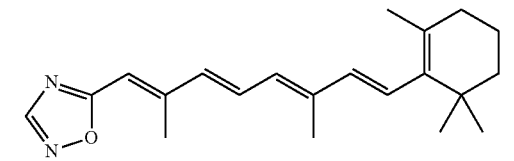 [SMILES: CC1=C(/C=C/C(C)=C/C=C/C(C)=C/c2ncno2)C(C)(C)CCC1] | −34.843 |
| 70 | 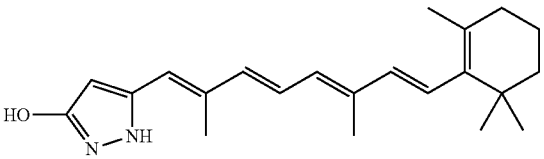 [SMILES: CC1=C(/C=C/C(C)=C/C=C/C(C)=C/c2cc(O)n[nH]2)C(C)(C)CCC1] | −34.823 |
| 71 | 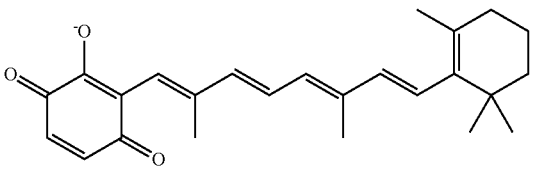 | −34.762 |

TABLE 3-continued
Additional retinoic acid compounds
| Compound Number | Compound | MMGBSA dG Bind |
|---|---|---|
| 72 | 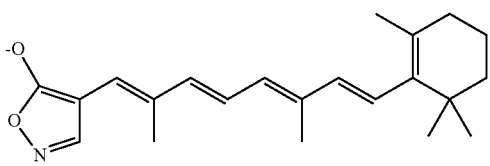 | −34.648 |
| 73 | 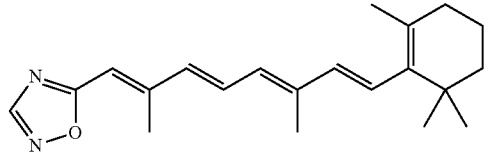 [SMILES: CC1=C(/C=C/C(C)=C/C=C/C(C)=C/c2ncno2)C(C)(C)CCC1] | −34.522 |
| 74 | 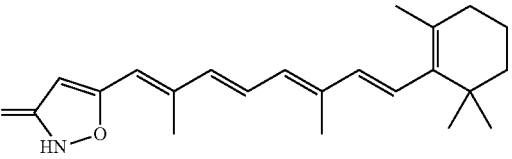 | −34.465 |
| 75 | 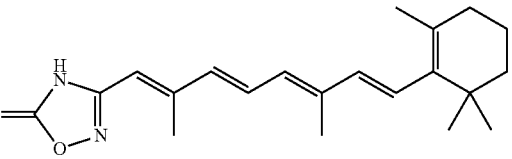 | −34.303 |
| 76 | 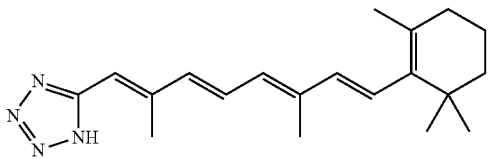 | −34.217 |
| 77 | 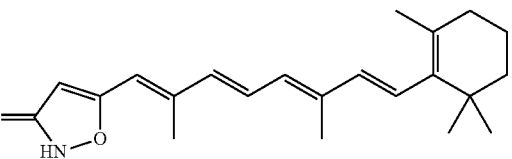 | −34.173 |
| 78 | 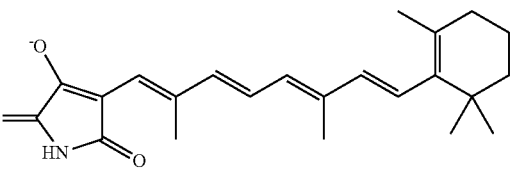 | −34.134 |
| 79 | 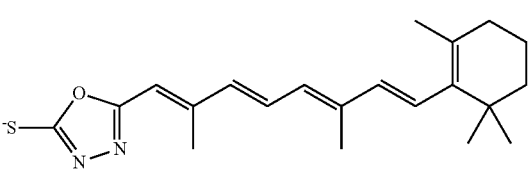 | −34.042 |

TABLE 3-continued

Additional retinoic acid compounds

| Compound Number | Compound | MMGBSA dG Bind |
|---|---|---|
| 80 | | −34.010 |
| 81 | | −33.982 |
| 82 | | −33.971 |
| 83 | | −33.948 |
| 84 | | −33.573 |
| 85 | | −33.498 |
| 86 | | −32.867 |
| 87 | | −32.431 |
| 88 | | −32.106 |

TABLE 3-continued

Additional retinoic acid compounds

| Compound Number | Compound | MMGBSA dG Bind |
|---|---|---|
| 89 | | −32.103 |
| 90 | | −31.917 |
| 91 | | −31.769 |
| 92 | | −31.700 |
| 93 | | −31.628 |
| 94 | | −31.591 |
| 95 | | −31.533 |
| 96 | | −31.228 |

TABLE 3-continued

Additional retinoic acid compounds

| Compound Number | Compound | MMGBSA dG Bind |
|---|---|---|
| 97 | | −30.921 |
| 98 | | −30.851 |
| 99 | | −30.640 |
| 100 | | −30.511 |
| 101 | | −30.252 |
| 102 | | −41.258 |
| 103 | | −40.318 |
| 104 | | −37.914 |

TABLE 3-continued
Additional retinoic acid compounds
| Compound Number | Compound | MMGBSA dG Bind |
|---|---|---|
| 105 | 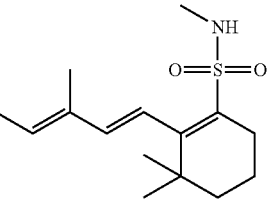 | −37.502 |
| 106 | 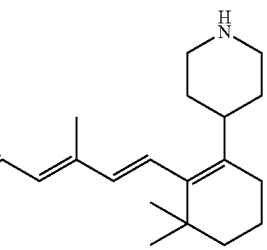 | −37.178 |
| 107 | 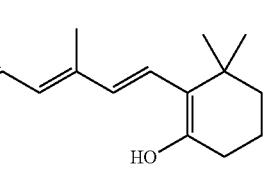 | −37.014 |
| 108 | 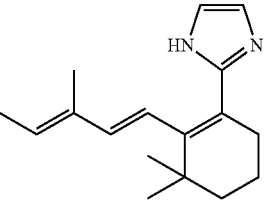 | −36.647 |
| 109 | 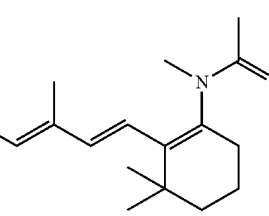 | −36.455 |
| 110 | 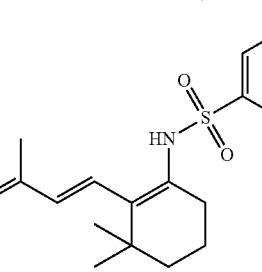 | −36.050 |
| 111 | 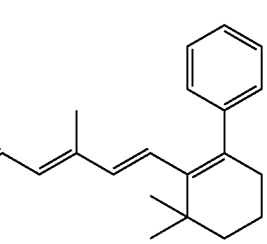 | −35.993 |

TABLE 3-continued
Additional retinoic acid compounds
| Compound Number | Compound | MMGBSA dG Bind |
|---|---|---|
| 112 | 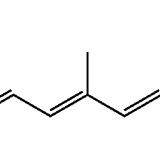 | −35.993 |
| 113 |  | −34.396 |
| 114 | 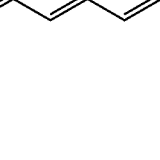 | −33.971 |
| 115 | 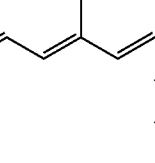 | −33.970 |
| 116 | 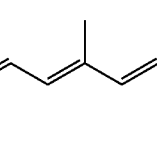 | −33.501 |
| 117 | 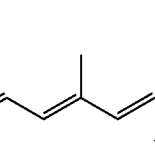 | −33.395 |
| 118 |  | −33.298 |

TABLE 3-continued

Additional retinoic acid compounds

| Compound Number | Compound | MMGBSA dG Bind |
|---|---|---|
| 119 | | −32.812 |
| 120 | | −32.087 |
| 121 | | −30.415 |
| 122 | | −30.226 |
| 123 | | −30.154 |
| 124 | | −30.137 |

TABLE 3-continued

Additional retinoic acid compounds

| Compound Number | Compound | MMGBSA dG Bind |
|---|---|---|
| 125 | | −30.052 |
| 126 | | −38.710 |
| 127 | | −38.225 |
| 128 | | −37.131 |
| 129 | | −36.785 |
| 130 | | −36.314 |

TABLE 3-continued

Additional retinoic acid compounds

| Compound Number | Compound | MMGBSA dG Bind |
|---|---|---|
| 131 | | −35.906 |
| 132 | | −35.695 |
| 133 | | −35.669 |
| 134 | | −35.419 |
| 135 | | −35.284 |
| 136 | | −34.966 |

TABLE 3-continued

Additional retinoic acid compounds

| Compound Number | Compound | MMGBSA dG Bind |
|---|---|---|
| 137 | | −34.466 |
| 138 | | −34.411 |
| 139 | | −34.268 |
| 140 | | −34.256 |
| 141 | | −33.085 |
| 142 | | −32.963 |

TABLE 3-continued

Additional retinoic acid compounds

| Compound Number | Compound | MMGBSA dG Bind |
|---|---|---|
| 143 | | −32.080 |
| 144 | | −31.664 |
| 145 | | −30.991 |
| 146 | | −30.819 |
| 147 | | −30.766 |
| 148 | | −30.370 |
| 149 | | −30.318 |

TABLE 3-continued

Additional retinoic acid compounds

| Compound Number | Compound | MMGBSA dG Bind |
|---|---|---|
| 150 | | −30.111 |
| 151 | | −43.497 |
| 152 | | −41.832 |
| 153 | | −40.871 |
| 154 | | −39.638 |
| 155 | | −38.360 |
| 156 | | −38.167 |

TABLE 3-continued

Additional retinoic acid compounds

| Compound Number | Compound | MMGBSA dG Bind |
|---|---|---|
| 157 | | −37.593 |
| 158 | | −37.523 |
| 159 | | −37.214 |
| 160 | | −36.927 |
| 161 | | −36.711 |
| 162 | | −36.274 |

TABLE 3-continued

Additional retinoic acid compounds

| Compound Number | Compound | MMGBSA dG Bind |
|---|---|---|
| 163 | | −35.940 |
| 164 | | −35.824 |
| 165 | | −35.720 |
| 166 | | −35.322 |
| 167 | | −34.656 |
| 168 | | −34.565 |

TABLE 3-continued

Additional retinoic acid compounds

| Compound Number | Compound | MMGBSA dG Bind |
|---|---|---|
| 169 | | −33.968 |
| 170 | | −32.483 |
| 171 | | −31.386 |
| 172 | | −31.339 |
| 173 | | −31.060 |
| 174 | | −30.951 |
| 175 | | −30.670 |

TABLE 3-continued

Additional retinoic acid compounds

| Compound Number | Compound | MMGBSA dG Bind |
|---|---|---|
| 176 | | −30.553 |
| 177 | | −48.677 |
| 178 | | −48.019 |
| 179 | | −47.880 |
| 180 | | −47.752 |
| 181 | | −47.697 |
| 182 | | −47.360 |

TABLE 3-continued

Additional retinoic acid compounds

| Compound Number | Compound | MMGBSA dG Bind |
|---|---|---|
| 183 | | −47.269 |
| 184 | | −46.786 |
| 185 | | −46.761 |
| 186 | | −46.392 |
| 187 | | −45.617 |
| 188 | | −45.455 |
| 189 | | −45.187 |
| 190 | | −44.921 |

TABLE 3-continued

Additional retinoic acid compounds

| Compound Number | Compound | MMGBSA dG Bind |
|---|---|---|
| 191 | | −44.915 |
| 192 | | −44.866 |
| 193 | | −44.729 |
| 194 | | −44.709 |
| 195 | | −44.707 |
| 196 | | −44.652 |
| 197 | | −44.554 |

TABLE 3-continued

Additional retinoic acid compounds

| Compound Number | Compound | MMGBSA dG Bind |
|---|---|---|
| 198 | | −44.505 |
| 199 | | −44.358 |
| 200 | | −44.353 |
| 201 | | −44.219 |
| 202 | | −44.152 |
| 203 | | −44.021 |
| 204 | | −43.946 |

TABLE 3-continued

Additional retinoic acid compounds

| Compound Number | Compound | MMGBSA dG Bind |
|---|---|---|
| 205 | | −43.886 |
| 206 | | −43.798 |
| 207 | | −43.743 |
| 208 | | −43.716 |
| 209 | | −43.575 |
| 210 | | −43.424 |
| 211 | | −43.403 |

TABLE 3-continued
Additional retinoic acid compounds
| Compound Number | Compound | MMGBSA dG Bind |
|---|---|---|
| 212 | 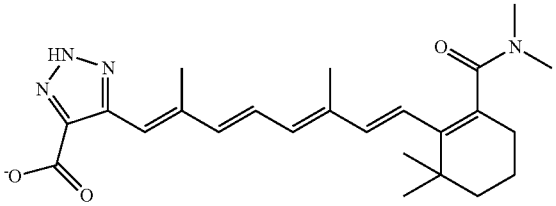 | −43.270 |
| 213 | 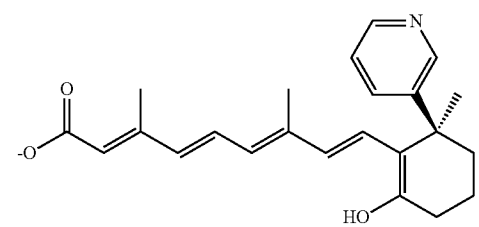 | −42.985 |
| 214 | 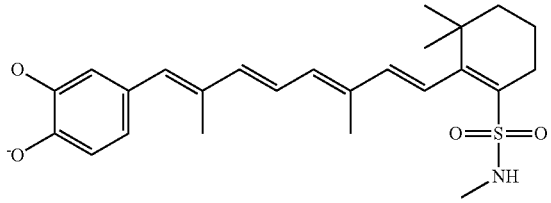 | −42.595 |
| 215 | 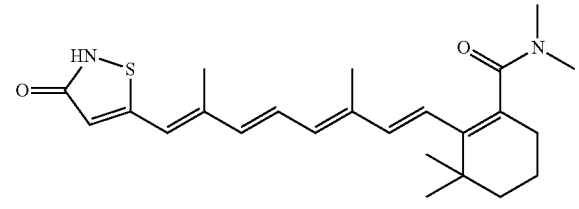 [SMILES: CC(/C=C/C1=C(C(=O)N(C)C)CCCC1(C)C)=C\C=C\C(C)=C\c1cc(=O)[nH]s1] | −42.420 |
| 216 | 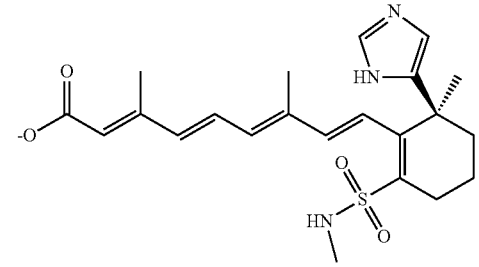 | −42.360 |
| 217 | 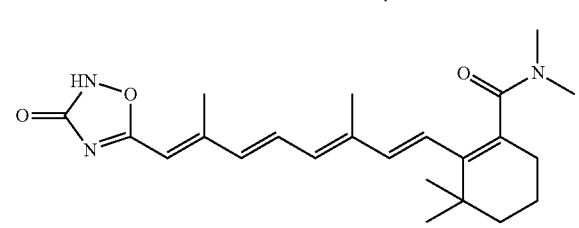 | −42.289 |
| 218 | 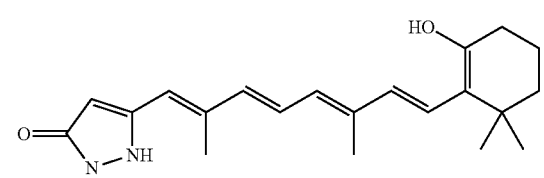 [SMILES: CC(/C=C/C1=C(O)CCCC1(C)C)=C\C=C\C(C)=C\c1cc(=O)[nH][nH]1] | −42.244 |

TABLE 3-continued
Additional retinoic acid compounds
| Compound Number | Compound | MMGBSA dG Bind |
|---|---|---|
| 219 | 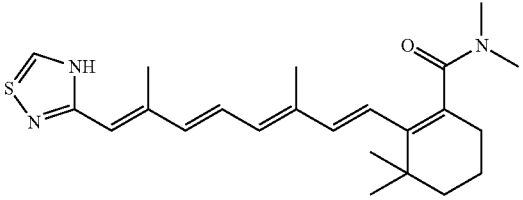 | −41.962 |
| 220 | 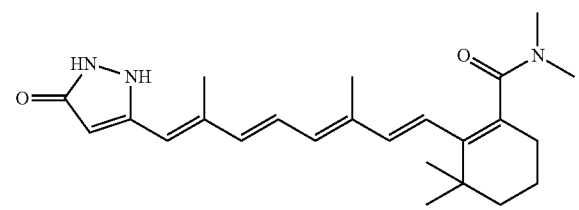 [SMILES: CC(/C=C/C1=C(C(=O)N(C)C)CCCC1(C)C)=C\C=C\C(C)=C\c1cc(=O)[nH][nH]1] | −41.884 |
| 221 | 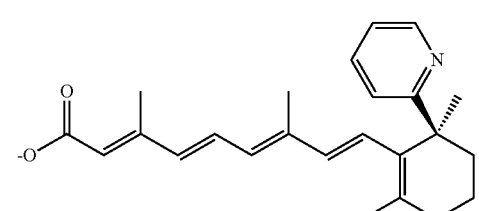 | −41.661 |
| 222 | 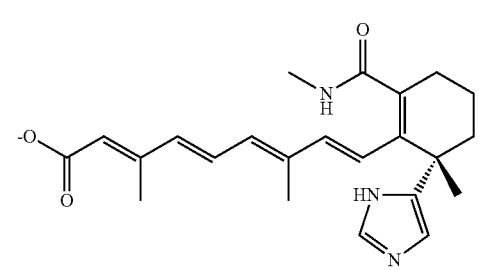 | −41.517 |
| 223 | 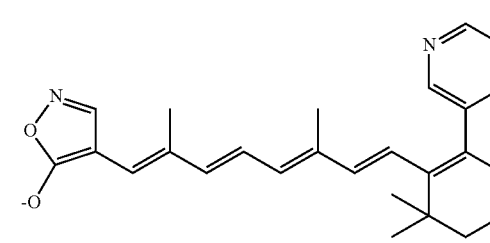 | −41.502 |
| 224 | 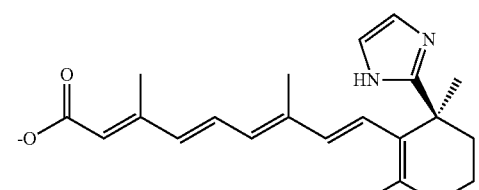 | −40.866 |

TABLE 3-continued

Additional retinoic acid compounds

| Compound Number | Compound | MMGBSA dG Bind |
|---|---|---|
| 225 | | −40.861 |
| 226 | | −40.804 |
| 227 | | −40.611 |
| 228 | | −40.470 |
| 229 | | −39.952 |
| 230 | | −39.895 |
| 231 | | −39.785 |

TABLE 3-continued

Additional retinoic acid compounds

| Compound Number | Compound | MMGBSA dG Bind |
|---|---|---|
| 232 | | −39.704 |
| 233 | | −39.520 |
| 234 | | −39.409 |
| 235 | | −39.169 |
| 236 | | −39.122 |
| 237 | | −38.985 |
| 238 | | −38.949 |

TABLE 3-continued

Additional retinoic acid compounds

| Compound Number | Compound | MMGBSA dG Bind |
|---|---|---|
| 239 | | −38.918 |
| 240 | | −38.495 |
| 241 | | −38.478 |
| 242 | | −38.423 |
| 243 | | −38.203 |
| 244 | | −38.198 |
| 245 | | −37.907 |

TABLE 3-continued

Additional retinoic acid compounds

| Compound Number | Compound | MMGBSA dG Bind |
|---|---|---|
| 246 | | −37.747 |
| 247 | | −37.674 |
| 248 | | −37.617 |
| 249 | | −37.559 |
| 250 | | −37.499 |
| 251 | | −37.379 |
| 252 | | −37.159 |

TABLE 3-continued

Additional retinoic acid compounds

| Compound Number | Compound | MMGBSA dG Bind |
|---|---|---|
| 253 | | −36.667 |
| 254 | | −36.467 |
| 255 | | −35.928 |
| 256 | | −35.741 |
| 257 | | −35.403 |
| 258 | | −35.039 |
| 259 | | −34.906 |

TABLE 3-continued

Additional retinoic acid compounds

| Compound Number | Compound | MMGBSA dG Bind |
|---|---|---|
| 260 | | −34.492 |
| 261 | | −32.922 |
| 262 | | −32.805 |
| 263 | | −32.786 |
| 264 | | −32.382 |
| 265 | | −31.879 |

TABLE 3-continued

Additional retinoic acid compounds

| Compound Number | Compound | MMGBSA dG Bind |
|---|---|---|
| 266 | | −31.566 |
| 267 | | −31.378 |
| 268 | | −31.366 |
| 269 | | −31.288 |
| 270 | | −30.991 |
| 271 | | −30.938 |

TABLE 3-continued

Additional retinoic acid compounds

| Compound Number | Compound | MMGBSA dG Bind |
|---|---|---|
| 272 | | −30.652 |

Further examples of retinoic acid compounds include any retinoic acid compounds, or derivatives thereof, known in the art, including those described in PCT Publication Nos. WO 2013/185055, WO 2015/143190, and WO 2016/145186, each of which is incorporated herein with respect to the compounds described therein.

The term "diterpene retinoic acid" encompasses any stereoisomer of retinoic acid (e.g., the retinoic acid may be in the all-trans configuration (ATRA) or one or more of the double bonds may be in the cis configuration, for example, 13cRA. Derivatives of the diterpene retinoic acid include reduced forms such as retinal, retinol, and retinyl acetate. In Formula (VI), each of $Ar^1$ and $Ar^2$ is, independently, optionally substituted aryl or an optionally substituted heteroaryl; $R^1$ is H, an optionally substituted alkyl group, an optionally substituted alkenyl group, or an optionally substituted alkynyl group; each of $L^1$ and $L^2$ is selected, independently from a covalent bond, an optionally substituted $C_{1-10}$ alkylene, an optionally substituted $C_{2-10}$ alkenylene (e.g., —CH=CH—, —COCH=CH—, —CH=CHCO—, a dienyl group, or a trienyl group), optionally substituted $C_{2-10}$ alkynylene (e.g., —C≡C—),or —(CHR$^4$)$_n$CONR$^5$—, —NR$^5$CO—, where n is 0 or 1, $R^4$ is H or OH, and $R^5$ is H or optionally substituted alkyl; and $R^3$ is H, OR$^4$ or N(R$^4$)$^2$, where each $R^4$ is selected, independently, from H, optionally substituted alkyl, or optionally substituted heteroalkyl.

As used herein, the term "C1-C6 alkoxy" represents a chemical substituent of formula —OR, where R is an optionally substituted C1-C6 alkyl group, unless otherwise specified. In some embodiments, the alkyl group can be substituted, e.g., the alkoxy group can have 1, 2, 3, 4, 5 or 6 substituent groups as defined herein.

As used herein, the term "C1-C6 acyl" refers to a C1-C6 alkyl group that includes a C(=O) moiety and which may be further substituted as described herein.

As used herein, the term "alkyl," "alkenyl" and "alkynyl" include straight-chain, branched-chain and cyclic monovalent substituents, as well as combinations of these, containing only C and H when unsubstituted. Examples include methyl, ethyl, isobutyl, cyclohexyl, cyclopentylethyl, 2 propenyl, 3 butynyl, and the like. The term "cycloalkyl," as used herein, represents a monovalent saturated or unsaturated non-aromatic cyclic alkyl group having between three to nine carbons (e.g., a C3-C9 cycloalkyl), unless otherwise specified, and is exemplified by cyclopropyl, cyclobutyl, cyclopentyl, cyclohexyl, cycloheptyl, bicyclo[2.2.1.]heptyl, and the like. In some embodiments, the cycloalkyl is a polycyclic (e.g., adamantyl). Cycloalkyl groups may be unsubstituted or substituted with, e.g., 1, 2, 3, or 4 substituent groups as defined herein. When the cycloalkyl group includes one carbon-carbon double bond, the cycloalkyl group can be referred to as a "cycloalkenyl" group. Exemplary cycloalkenyl groups include cyclopentenyl, cyclohexenyl, and the like.

Typically, the alkyl, alkenyl and alkynyl groups contain 1-12 carbons (e.g., C1-C12 alkyl) or 2-12 carbons (e.g., C2-C12 alkenyl or C2-C12 alkynyl). In some embodiments, the alkyl groups are C1-C8, C1-C6, C1-C4, C1-C3, or C1-C2 alkyl groups; or C2-C8, C2-C6, C2-C4, or C2-C3 alkenyl or alkynyl groups. Further, any hydrogen atom on one of these groups can be replaced with a substituent as described herein.

The term "aryl," as used herein, represents a mono- or bicyclic $C_6$-$C_{14}$ group with [4n+2] π electrons in conjugation and where n is 1, 2, or 3. Aryl groups also include ring systems where the ring system having [4n+2] π electrons is fused to a non-aromatic cycloalkyl or a non-aromatic heterocyclyl. Phenyl is an aryl group where n is 1. Aryl groups may be unsubstituted or substituted with, e.g., 1, 2, 3, or 4 substituent groups as defined herein. Still other exemplary aryl groups include, but are not limited to, naphthyl, 1,2-dihydronaphthyl, 1,2,3,4-tetrahydronaphthyl, fluorenyl, indanyl, and indenyl.

The term "heteroaryl," as used herein, represents an aromatic (i.e., containing 4n+2 pi electrons within the ring system) 5- or 6-membered ring containing one, two, three, or four heteroatoms independently selected from the group consisting of nitrogen, oxygen, and sulfur, as well as bicyclic, tricyclic, and tetracyclic groups in which any of the aromatic ring is fused to one, two, or three heterocyclic or carbocyclic rings (e.g., an aryl ring). Exemplary heteroaryls include, but are not limited to, furan, thiophene, pyrrole, thiadiazole (e.g., 1,2,3-thiadiazole or 1,2,4-thiadiazole), oxadiazole (e.g., 1,2,3-oxadiazole or 1,2,5-oxadiazole), oxazole, isoxazole, isothiazole, pyrazole, thiazole, triazole (e.g., 1,2,4-triazole or 1,2,3-triazole), pyridine, pyrimidine, pyrazine, pyrazine, triazine (e.g, 1,2,3-triazine 1,2,4-triazine, or 1,3,5-triazine), 1,2,4,5-tetrazine, indolyl, quinolinyl, isoquinolinyl, benzimidazolyl, benzothiazolyl, and benzoxazolyl. Heteroaryls may be unsubstituted or substituted with, e.g., 1, 2, 3, or 4 substituents groups as defined herein.

The term "heterocyclyl," as used herein represents a non-aromatic 5-, 6- or 7-membered ring, unless otherwise specified, containing one, two, three, or four heteroatoms independently selected from the group consisting of nitrogen, oxygen, and sulfur. Heterocyclyl groups may be unsubstituted or substituted with, e.g., 1, 2, 3, or 4 substituent groups as defined herein.

As used herein, the term "aryloxy" refers to aromatic or heteroaromatic systems which are coupled to another residue through an oxygen atom. A typical example of an O-aryl is phenoxy. Similarly, "thioaryloxy" refers to aromatic or heteroaromatic systems which are coupled to another residue through a sulfur atom.

As used herein, a halogen is selected from F, Cl, Br, and I, and more particularly it is fluoro or chloro.

Where a group is substituted, the group may be substituted with 1, 2, 3, 4, 5, or 6 substituent groups. Optional substituent groups include, but are not limited to: $C_{1-6}$ alkyl, $C_{2-6}$ alkenyl, $C_{2-6}$ alkynyl, aryl, heteroaryl, cycloalkyl, heterocyclyl, halogen (—F, —Cl, —Br, or —I), azido(—$N_3$), nitro (—$NO_2$), cyano (—CN), acyloxy (—OC(=O)R'), acyl (—C(=O)R'), alkoxy (—OR'), amido (—NR'C(=O)R" or —C(=O)NRR'), amino (—NRR'), carboxylic acid (—$CO_2$H), carboxylic ester (—$CO_2$R'), carbamoyl (—OC(=O)NR'R" or —NRC(=O)OR'), hydroxy (—OH), oxo (=O), isocyano (—NC), sulfonate (—S(=O)$_2$OR), sulfonamide (—S(=O)$_2$NRR' or —NRS(=O)$_2$R'), or sulfonyl (—S(=O)$_2$R), where each R or R' is selected, independently, from H, $C_{1-6}$ alkyl, $C_{2-6}$ alkenyl, $C_{2-6}$ alkynyl, aryl, or heteroaryl.

In general, a substituent group (e.g., alkyl, alkenyl, alkynyl, or aryl (including all heteroforms defined above) may itself optionally be substituted by additional substituents. The nature of these substituents is similar to those recited with regard to the substituents on the basic structures above. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments, and is not included. For example, where a group is substituted, the group may be substituted with 1, 2, 3, 4, 5, or 6 substituents. Optional substituents include, but are not limited to: C1-C6 alkyl or heteroaryl, C2-C6 alkenyl or heteroalkenyl, C2-C6 alkynyl or heteroalkynyl, halogen; aryl, heteroaryl, azido (—N3), nitro (—NO2), cyano (—CN), acyloxy (OC(=O)R'), acyl (—C(=O)R'), alkoxy (—OR'), amido (—NR'C(=O)R" or —C(=O)NRR'), amino (NRR'), carboxylic acid (—CO2H), carboxylic ester (—CO2R'), carbamoyl (OC(=O)NR'R" or —NRC(=O)OR'), hydroxy (OH), isocyano (—NC), sulfonate (S(=O)2OR), sulfonamide (S(=O)2NRR' or —NRS(=O)2R'), or sulfonyl (S(=O)2R), where each R or R' is selected, independently, from H, C1-C6 alkyl or heteroaryl, C2-C6 alkenyl or heteroalkenyl, 2C-6C alkynyl or heteroalkynyl, aryl, or heteroaryl. A substituted group may have, for example, 1, 2, 3, 4, 5, 6, 7, 8, or 9 substituents.

Typical optional substituents on aromatic or heteroaromatic groups include independently halo, CN, NO2, CF3, OCF3, COOR', CONR'2, OR', SR', SOR', SO2R', NR'2, NR'(CO)R', NR'C(O)OR', NR'C(O)NR'2, NR'SO2NR'2, or NR'SO2R', wherein each R' is independently H or an optionally substituted group selected from alkyl, alkenyl, alkynyl, heteroalkyl, heteroalkenyl, heteroalkynyl, heteroaryl, and aryl (all as defined above); or the substituent may be an optionally substituted group selected from alkyl, alkenyl, alkynyl, heteroalkyl, heteroalkenyl, heteroalkynyl, aryl, heteroaryl, O-aryl, O-heteroaryl and arylalkyl.

Optional substituents on a non-aromatic group (e.g., alkyl, alkenyl, and alkynyl groups), are typically selected from the same list of substituents suitable for aromatic or heteroaromatic groups, except as noted otherwise herein. A non-aromatic group may also include a substituent selected from =O and =NOR' where R' is H or an optionally substituted group selected from alkyl, alkenyl, alkynyl, heteroalkyl, heteroalkenyl, heteralkynyl, heteroaryl, and aryl (all as defined above).

As used herein, the terms "sample" and "biological sample" include samples obtained from a cell or a subject (e.g., a mammal, such as a human) containing Pin1 which can be used within the methods described herein. Exemplary types of samples include tissues, cells, biopsies, and biological fluids isolated from a subject, as well as tissues, cells, and fluids present within a subject. Samples from a subject include, for example, tissue samples, tumor samples, blood, urine, cerebrospinal fluid, biopsies, lymph, saliva, phlegm, pus, and combinations or constituents thereof.

The term "synergy" or "synergistic," as used herein, refers to an improved effect when two agents are administered that is greater than the additive effects of each of the two agents when administered alone. In one example, administration of an arsenic trioxide and a retinoic acid compound (e.g., ATRA) to a subject (e.g., a subject having a Pin1-associated disorder) may result in a greater than additive effect on the subject than administration of either arsenic trioxide or the retinoic acid compound alone.

By a "low dose" or "low dosage" is meant a dosage of at least 5% less (e.g., at least 5%, 10%, 20%, 25%, 30%, 40%, 50%, 60%, 70%, 80%, 90%, 91%, 92%, 93%, 94%, 95%, 96%, 97%, 98%, or 99% less) than the standard recommended dosage or lowest standard recommended dosage of a particular agent, e.g., a therapeutic agent formulated for a given route of administration for treatment of any human disease or condition. For example, a low dosage of an agent formulated for oral administration may differ from a low dosage of the agent formulated for intravenous administration. In some instances, a low dosage of an agent may be selected to be a nontoxic dosage of the agent. In some instances, a low dosage may be selected as a dosage that minimizes particular side effects of an agent, but which may still retain some side effects. For example, a dosage may be selected that minimizes or eliminates side effects that can lead to significant mortality or severe illness among subjects while still permitting more tolerable side effects, such as headache. In some instances, a low dose of arsenic trioxide is a dose of about 2 mg/kg body weight or less (e.g., about 0.01, 0.02, 0.03, 0.032, 0.04, 0.05, 0.06, 0.07, 0.08, 0.09, 0.1, 0.15, 0.16, 0.2, 0.3, 0.4, 0.5, 0.6, 0.7, 0.8, 0.9, 1.0, 1.25, 1.5, 1.75, or 2 mg/kg). In certain instances, a low dose of arsenic trioxide is about 0.15, about 0.16, or about 0.032 mg/kg body weight. In other instances, a low dose of arsenic trioxide is a dose between about 0.5 mg/kg and about 12 mg/kg body weight (e.g., about 0.5, 0.6, 0.7, 0.8, 0.9, 1, 2, 3, 4, 5, 6, 7, 8, 9, 10, 11, or 12 mg/kg). In some instances, a low dose of a retinoic acid compound is a dose of about 5 mg/kg body weight or less (e.g., about 0.1, 0.2, 0.5, 0.75, 1, 2, 3, 4, or 5 mg/kg). In some instances, a low dose of a retinoic acid compound is a dose of about 25 mg/m$^2$ or less (e.g., about 1, 2, 3, 4, 5, 6, 7, 8, 9, 10, 11, 12, 13, 14, 15, 16, 17, 18, 19, 20, 21, 22, 23, 24, or 25 mg/m$^2$). In other instances, the low dose of the retinoic acid compound is a dose of between 25 mg/m$^2$ and 45 mg/m$^2$ (e.g., 25, 26, 27, 28, 29, 30, 31, 32, 33, 34, 35, 36, 37, 38, 39, 40, 41, 42, 43, 44, or 45 mg/m$^2$).

A "nontoxic" dose of an agent (e.g., arsenic trioxide and/or a retinoic acid compound) is a dosage low enough to minimize or eliminate toxic side effects of the agent on the subject to which the agent is administered. A nontoxic dosage may be achieved by reducing the quantity of the agent administered per dose and/or increasing the length of time between deliveries of individual doses.

The term "effective amount" or an amount "sufficient to" as used interchangeably herein, refers to a quantity of an agent that, when administered alone or with one or more additional therapeutic agents, induces a desired response. The desired response may be a therapeutic response. In one example, the desired response is decreasing the signs or symptoms of a proliferative disorder (e.g., a cancer as described herein). In another example, the desired response is decreasing the risk of developing or decreasing the risk of recurrence of a proliferative disorder (e.g., a cancer as described herein). An effective amount of an agent may desirably provide a therapeutic effect without causing substantial toxicity in the subject. In some instances, an effective amount of an agent may alter the level of Pin1 activity and/or the level of a Pin1 marker in a cell or subject. For example, an effective amount of an agent may reduce the level of Pin1 activity and/or the level of a Pin1 marker to, e.g., levels present in a wild-type cell or subject. In general, an effective amount of a composition administered to a human subject will vary depending upon a number of factors associated with that subject, for example, the overall health of the subject, the condition to be treated, and/or the severity of the condition. An effective amount of a composition can be determined by varying the dosage of the product and measuring the resulting therapeutic response. The effective amount can be dependent, for example, on the source applied, the subject being treated, the severity and type of the condition being treated, and the manner of administration.

"Subject," as used herein, refers to any organism or portion thereof to be administered a composition as described herein (e.g., arsenic trioxide, a retinoic acid compound, and combinations or derivatives thereof). A subject may be an animal, such as a mammal (e.g., a human, mouse, rat, rabbit, dog, cat, goat, pig, and horse). Preferably, the subject is human. A "wild-type" subject is a subject having normal levels of Pin1 activity for its species and developmental stage. Different parts of a wild-type subject may exhibit different levels of normal Pin1 activity. Comparison of a wild-type subject to another subject (e.g., a subject that may have elevated levels of Pin1 activity) is generally done by comparing Pin1 activity levels in the same portion (e.g., tissue, cell type, cell, and/or biological sample, for example, as described herein) from both subjects.

As used herein, the term "Pin1-associated disorder" refers to any disease, disorder, or condition associated with aberrant Pin1 activity (e.g., elevated or decreased Pin1 activity relative to a healthy and/or wild-type subject). In some instances, the aberrant Pin1 activity is related to an alteration in Pin1 expression. Aberrant Pin1 activity may, in some instances, be assessed by the presence of elevated Pin1 markers, e.g., as described herein. Preferably, a Pin1-associated disorder is a disease, disorder, or condition associated with elevated Pin1 activity relative to a healthy and/or wild-type subject. A Pin1-associated disorder may be treated using an agent that reduces Pin1 activity in the subject (e.g., arsenic trioxide, a retinoic acid compound, or a combination thereof, for example, as described herein). Pin1-associated disorders may include, for example, proliferative disorders (e.g., cancers), inflammatory conditions, and autoimmune disorders associated with aberrant levels of Pin1 activity. In certain instances, a Pin1-associated disorder may be associated with an infection.

By "inhibiting, reducing, or reversing a phenotype" is meant, respectively, preventing the occurrence of a phenotype, decreasing the severity of a phenotype, or returning to a reference state wherein the phenotype is not present. For example, wherein the phenotype is elevated Pin 1 activity, for example in a subject or a cell, inhibiting, reducing, or reversing the phenotype would include any of the following: preventing elevation of a Pin1 activity in a cell, decreasing elevated levels Pin1 activity in a cell, or returning Pin1 activity in a cell to a level that is comparable to wild-type levels (e.g., a wild-type cell of the same cell type). The term "inhibiting, reducing, or reversing a phenotype associated with elevated Pin1 activity in a cell" may be considered to include any of the following: preventing the occurrence of a phenotype associated with elevated levels of Pin1 in a cell, decreasing the severity of a phenotype associated with elevated levels of Pin1 in a cell, or returning to a reference state wherein the phenotype associated with increased levels of Pin1 activity in a cell is absent. Exemplary phenotypes associated with a Pin1 associated disorder include increased cell death, oncogenic transformation, and/or an autoimmune phenotype, such as, overproduction of cytokines and/or the overproduction of autoantibodies.

In some embodiments the cell is an oncogenic transformed cell or an autoimmune cell. In some embodiments, the cell is an oncogenic transformed cell and the cell becomes a non-transformed (e.g., not oncogenic) cell upon administration of the arsenic trioxide.

By the term "proliferative disorder" is meant a disease, disorder, or pathological condition characterized by inappropriate accumulation of a cell population in a tissue (e.g., by abnormal cell growth). This inappropriate accumulation may be the result of a genetic or epigenetic variation that occurs in one or more cells of the cell population. This genetic or epigenetic variation causes the cells of the cell population to grow faster, die slower, or differentiate slower than the surrounding, normal tissue. The cell population includes cells of hematopoietic, epithelial, endothelial, or solid tissue origin. Such proliferative disorders (e.g., cancers) may be effectively treated using an agent (e.g., arsenic trioxide, a retinoic acid compound, or combinations thereof) capable of reducing Pin1 activity in a subject having the proliferative disorders. Examples of proliferative disorders that may be associated with elevated Pin1 activity include, without limitation, breast cancer, liver cancer, colon cancer, pancreatic cancer, ovarian cancer, prostate cancer, cervical cancer, uterine cancer, testicular cancer, lung cancer, brain cancer, throat cancer, leukemia, Hodgkin's disease, non-Hodgkin's disease, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma. In certain instances, the cancer is breast cancer (e.g., triple-negative breast cancer). In other instances, the caner is liver cancer (e.g., HBV-related liver cancer).

"Abnormal cell growth" refers to cell growth that is undesirable or inappropriate. Abnormal cell growth also includes proliferation which is undesirable or inappropriate (e.g., unregulated cell proliferation or undesirably rapid cell proliferation). Abnormal cell growth can be benign and result in benign masses of tissue or cells, or benign tumors. Many art-recognized conditions are associated with such benign masses or benign tumors including diabetic retinopathy, retrolental fibrioplasia, neovascular glaucoma, psoriasis, angiofibromas, rheumatoid arthrtis, hemangiomas, and Karposi's sarcoma. Abnormal cell growth can also be malignant and result in malignancies, malignant masses of tissue or cells, or malignant tumors. Many art-recognized conditions and disorders are associated with malignancies, malignant masses, and malignant tumors, including cancers.

As used herein, the term "tumor" is intended to encompass both in vitro and in vivo tumors that form in any organ of the body. Tumors may be associated with benign abnormal cell growth (e.g., benign tumors) or malignant cell growth (e.g., malignant tumors). The tumors which are described herein are preferably sensitive to reduction of Pin1 activity, e.g., according to the methods described herein. Non-limiting examples of the types of tumors intended to be encompassed by the present invention include those tumors associated with breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys.

The term "inflammatory condition," as used herein, refers to any disease, disorder, or pathological condition associated with excessive inflammation. An inflammatory condition may be associated with elevated levels of Pin1 activity. Such inflammatory conditions may be effectively treated using an agent (e.g., arsenic trioxide, a retinoic acid compound, or combinations thereof) capable of reducing Pin1 activity in a subject having the inflammatory condition. Non-limiting examples of inflammatory conditions include arthritis, asthma, osteoarthritis, joint inflammation, inflammatory joint pain, inflammatory pain relayed via dorsal root ganglia (DRG), an infectious disease, an autoimmune disease, peripheral nerve injury, neuropathic pain, temporomandibular joint (TMJ) disorder, fibromyalgia, hyperalgesia, mechanical allodynia, chronic/persistent pain, acute pain, postoperative pain, acute lung injury (ALI), acute respiratory distress syndrome (ARDS), cystic fibrosis, chronic obstructive pulmonary disease (COPD), allergic asthma, severe asthma, bronchial mucosal inflammation, acute inflammatory response, chronic inflammation, abscess, thrombosis, allergic inflammation, sepsis, septic shock, ischemia-reperfusion injury, inflammatory bowel disease, colitis, intestinal inflammation, gastroesophageal reflux disease, ocular neovascularisation, posterior ocular inflammation, retinopathy, psoriasis, eczema, periodontitis, peritonitis, celiac disease, chronic prostatitis, benign prostatichypertrophy, glomerulonephritis, hypersensitivities, inflammatory bowel diseases, pelvic inflammatory disease, sarcoidosis, transplant rejection, vasculitis, interstitial cystitis, sterile inflammation, gout, silicosis, siderosis, joint loosening, and asbestosis. In some instances, the inflammatory condition is arthritis or asthma.

By "autoimmune disorder" is meant a disease, disorder, or pathological condition relating to an abnormal immune response to substances, cells, and/or tissues that are normally present in the body. An autoimmune disorder may be associated with elevated levels of Pin1 activity. Such autoimmune disorders may be effectively treated using an agent (e.g., arsenic trioxide, a retinoic acid compound, or combinations thereof) capable of reducing Pin1 activity in a subject having the autoimmune disorder. Examples of autoimmune disorders include, without limitation, lupus erythematosus, rheumatoid arthritis, multiple sclerosis (MS), encephalomyelitis, Addison's disease, agammaglbulinemia, alopecia areata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmunehemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo concentric sclerosis, Behcet's disease, Berger's disease, Bickerstaff's encephalitis, Blau syndrome, bullous pemphigoid, chronic bronchitis, Castleman's disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's syndrome, cutaneous leukocytoclastic vasculitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressive, fibrosing alveolitis, gastritis, gastrointestinal pemphigoid, giant cell arteritis, glomerulonephritis, Goodpasture's syndrome, Grave's disease, Guillain-Barre syndrome, Hashimoto's encephalopathy, Hashimoto's thyroiditis, Henoch-Schonlein purpura, herpes gestationis, hidradenitis suppurativa, Hughes-Stovin syndrome, hypertension, hypogammaglobulinemia, idiopathic inflammatory demyelinating diseases, idiopathic pulmonary fibrosis, idiopathic thrombocytopenic purpura, IgA nephropathy, inclusion body myositis, chronic inflammatory demyelinating polyneuropathy, interstitial cystitis, juvenile idiopathic arthritis, Kawasaki's disease, Lambert-Eaton myasthenic syndrome, leukocytoclastic vasculitis, lichen planus, lichen sclerosus, linear IgA disease, Majeed syndrome, Meniere's disease, microscopic polyangiitis, mixed connective tissue disease, morphea, Mucha-Habermann disease, myasthenia gravis, myositis, narcolepsy, neuromyelitis optica, neuromyotonia, ocular cicatricial pemphigoid, opsoclonus myoclonus syndrome, Ord's thyroiditis, palindromic rheumatism, PANDAS, paraneoplastic cerebellar degeneration, paroxysmal nocturnal hemoglobinuria, Parry Romberg syndrome, Parsonage-Turner syndrome, pars planitis, pemphigus vulgaris, pernicious anaemia, perivenous encephalomyelitis, peripheral vascular disease, POEMS syndrome, polyarteritis nodosa, polymyalgia rheumatic, polymyositis, primary biliary cirrhosis, primary sclerosing cholangitis, progressive inflammatory neuropathy, psoriatic arthritis, psoriasis, pyoderma gangrenosum, pure red cell aplasia, Rasmussen's encephalitis, raynaud phenomenon, relapsing polychondritis, Reiter's syndrome, restless leg syndrome, retroperitoneal fibrosis, rheumatic fever, rheumatoid arthritis, Schnitzler syndrome, scleritis, scleroderma, serum sickness, chronic sinusitis, Sjogren's syndrome, spondyloarthropathy, stiff person syndrome, subacute bacterial endocarditis, Susac's syndrome, Sweet's syndrome, sympathetic ophthalmia, Takayasu's arteritis, temporal arteritis, thrombocytopenia, Tolosa-Hunt syndrome, transverse myelitis, ulcerative colitis, undifferentiated connective tissue disease, undifferentiated spondyloarthropathy, vitiligo, and Wegener's granulomatosis. In certain instances, the autoimmune disorder is lupus erythematosus.

As used herein, the term "administering" may also be considered to include contacting. For example, wherein a compound is administered to a cell, it may be considered to be equivalent to contacting the cell with the compound.

By "about" is meant any value within 10% above or below the indicated value.

Wherein a range of values is provided, the range is considered to include the upper and lower bounds of the range and any values within the range.

BRIEF DESCRIPTION OF THE DRAWINGS

The application file contains at least one drawing executed in color. Copies of this patent or patent application with color drawings will be provided by the Office upon request and payment of the necessary fee.

FIG. 2A is a graph depicting the effect of arsenic trioxide treatment on three populations of mouse embryonic fibroblast cells: wild-type (WT), Pin1 knockout (Pin1-KO) and, Pin1 KO reconstituted with WT Pin1 (WT Pin1 in Pin1-KO). The Pin1-KO population is more resistant to inhibition of cellular proliferation as compared to WT cells. Reintroduction of WT Pin1 (WT Pin1 in Pin1-KO) rescues sensitivity to treatment with ATO. FIG. 2B is a western blot showing the reduction of Pin1 expression in the WT and WT Pin1 in Pin1-KO population upon treatment with arsenic trioxide. FIG. 2C is a graph depicting the quantification of protein expression levels of FIG. 2B.

FIGS. 13A-C depicts inhibition of tumor growth in an MDA-MB 231 triple-negative breast cancer cell mouse tumor xenograft model. FIG. 13A is a graph that depicts that combination treatment with ATRA and ATO results in greater tumor growth inhibition than treatment with either ATRA or ATO, alone. FIG. 13B is an image of the excised tumors corresponding to FIG. 13A. FIG. 13C is a western blot depicting a greater decrease in Pin1 expression following combination treatment with ATRA and ATO, as compared to treatment with either ATRA or ATO, alone.

FIGS. 14A-C show that AQP9 overexpression converts ATO resistant breast cancer cells to become ATO-sensitive. FIG. 14A is a graph depicting the effect of ATO treatment on the cell viability of human breast cancer cell lines. FIG. 14B is a western blot depicting AQP9 overexpression in three ATO-resistant human breast cancer cell lines: MCF-7, BT549, and T47D. FIG. 14C is a series of graphs showing that overexpression of AQP9 potentiates the ability of ATO to inhibit cell growth in all three cell lines.

FIGS. 15A-B show that AQP9 overexpression induces Pin1 degradation in ATO-resistant cells. FIG. 15A is a series of western blots showing that AQP9 overexpression induces Pin1 degradation in ATO-resistant breast cancer cell lines (MCF7, BT549, and T47D). FIG. 15B is series of graphs showing the quantification of Pin1 protein levels as determined in the western blots of FIG. 15A.

FIGS. 16A-C are a series of graphs showing that ATRA increases intracellular arsenic concentration measured by ICP-Masspec. FIG. 16A is a graph showing that treatment of an MDA-MB-231 breast cancer cell line with ATRA was found to increase intracellular arsenic concentrations relative to control. FIG. 16B is a graph showing that knockdown of AQP9 expression with an AQP9 shRNA was found to decrease intracellular arsenic concentrations relative to control. FIG. 16C is a graph showing that overexpression of AQP9 in an MCF-7 breast cancer cell line was found to increase intracellular arsenic concentrations relative to control.

FIGS. 17A-C show that ATO and ATRA effect for mouse orthotopic implantation model using triple negative breast cancer cell, MDA-MB-231. FIG. 17A is a graph showing that combination treatment with ATRA and ATO results in greater tumor growth inhibition than treatment with either ATRA or ATO, alone. FIG. 17B is image of the excised tumors corresponding to FIG. 17A. FIG. 17C is a graph depicting tumor volume corresponding to the tumors pictured in FIG. 17B.

FIGS. 18A-D show the effect of ATO and ATRA on a triple negative breast cancer patient-derived xenograft (PDX) mouse model, where treatment was initiated two weeks after implantation. FIG. 18A is a graph showing that combination treatment with ATRA and ATO results in greater tumor growth inhibition than treatment with either ATRA or ATO, alone. FIG. 18B is image of the excised tumors corresponding to FIG. 18A. FIG. 18C is a graph depicting tumor volume corresponding to the tumors picture in FIG. 18B. FIG. 18D is a western blot depicting a greater decrease in Pin1 expression following combination treatment with ATRA and ATO, as compared to treatment with either ATRA or ATO, alone.

FIGS. 19A-C show the effect of ATO and ATRA on a triple negative breast cancer PDX mouse model, where treatment was initiated when the tumor volume reached to 250 mm$^3$. FIG. 19A is a graph showing that combination treatment with ATRA and ATO results in greater tumor growth inhibition than treatment with either ATRA or ATO, alone. FIG. 19B is image of the excised tumors corresponding to FIG. 19A. FIG. 19C is a graph depicting tumor volume corresponding to the tumors picture in FIG. 19B.

FIGS. 20A-D show the effect of ATO and ATRA on a triple negative breast cancer PDX mouse model, where treatment was initiated when the tumor volume reached to 300 mm$^3$. FIG. 20A is a graph showing that combination treatment with ATRA and ATO results in greater tumor growth inhibition than treatment with either ATRA or ATO, alone. FIG. 20B is image of the excised tumors corresponding to FIG. 20A. FIG. 20C is a graph depicting tumor volume corresponding to the tumors picture in FIG. 20B. FIG. 20D is a western blot depicting a decrease in Pin1 expression following treatment with either ATO, ATRA, or a combination of ATO and ATRA.

FIGS. 21A-C show that ATO and ATRA synergistically inhibit the population and self-renewal of tumor-initiating cells (TICs) in triple-negative breast cancer cells (TNBCs). FIGS. 21A and 21B are graphs showing that, while ATO and ATRA individually significantly reduced breast TIC-enriched population, their combination synergistically reduced the CD24-CD44$_+$ (FIG. 21A) or ALDH$_+$ (FIG. 21B) populations. FIG. 21C is a graphs showing that co-treatment of ATO and ATRA displayed synergistic effects, almost completely inhibiting mammosphere formation efficiency at M1 (FIG. 21C).

FIGS. 22A-C show that ATO and ATRA synergistically inhibit taxol resistance, tumor initiation and tumor growth of tumor-initiating cells (TICs) in triple-negative breast cancer cells (TNBCs). FIG. 22A is a set of graphs showing that treatment with ATO and ATRA, especially in combination, potently inhibited the growth of taxol-resistant cells. FIG. 22B is a set of graphs showing that treatment with ATO and ATRA, especially in combination, also effectively inhibits self-renewal of taxol-resistant breast TICs, as assayed by the serial mammosphere formation assay. FIG. 22C is a graph showing that ATO and ATRA co-treatment dramatically reduces tumor growth.

DETAILED DESCRIPTION OF THE INVENTION

Figure 1:
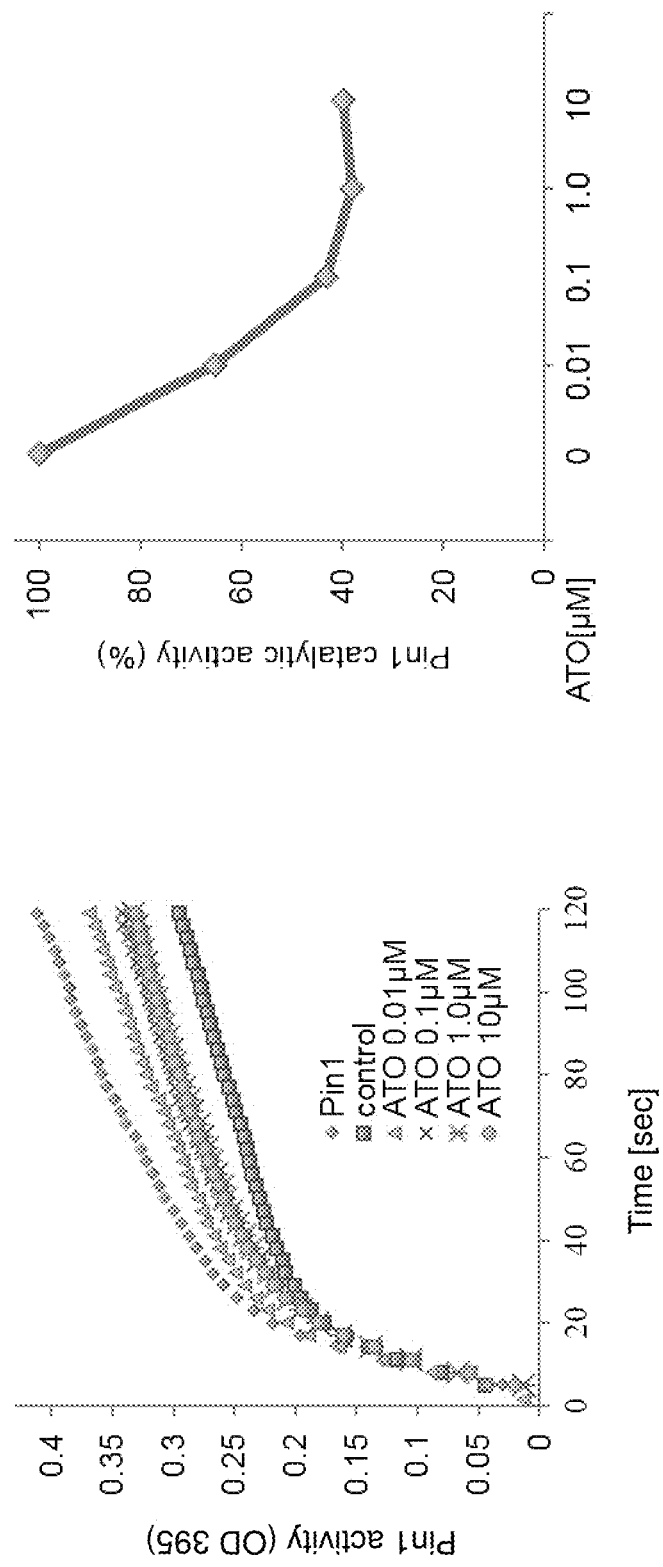
FIG. 1 is set of graphs depicting the dose-responsive inhibition of Pin1 catalytic activity following treatment with arsenic trioxide (ATO). Recombinant Pin1 was incubated in vitro with either 0 µM (Pin1), 0.01 µM, 0.1 µM, 1.0 µM, or 10 µM arsenic trioxide, and Pin1 activity was measured as described in Example 1. A dose-responsive inhibition of Pin1 activity is observed with increasing concentrations of arsenic trioxide.

The invention features methods of treating cellular phenotypes associated with elevated Pin1 activity by administering an arsenic trioxide compound. Contacting a cell exhibiting elevated Pin1 activity with arsenic trioxide may result in a decrease in Pin1 activity in the cell (e.g., by inducing degradation of Pin1). The cell may be present within a subject (e.g., a human subject). In some instances, the subject is administered arsenic trioxide to reduce Pin1 activity in the subject. Such reduction of Pin1 activity may result in treatment of a Pin1-associated disorder in the subject (e.g., a disorder related to elevated Pin1 activity). In addition, the invention features administration of arsenic trioxide in combination with a retinoic acid compound. Such a combination of arsenic trioxide and a retinoic acid compound may synergistically reduce Pin1 activity. Also provided are in vitro methods for reducing Pin1 activity in one or more cells by contacting the cells with arsenic trioxide and/or a retinoic acid compound.

Pin1-Associated Disorders

Pin1-catalyzed cis-trans isomerization of phosphorylated Ser/Thr-Pro motifs has been shown to be involved in an increasing number of diseases. Elevated levels of Pin1 activity have been associated with, for example, numerous cancers and autoimmune disorders. In some embodiments arsenic trioxide and/or a retinoic acid compound is administered to a subject having a Pin1-associated disorder.

Pin1 in Cancer

Elevated Pin1 activity has been associated with the development and progression of cancer. For example, Pin1 is overexpressed in some human cancer samples and the levels of Pin1 are correlated with the aggressiveness of tumors. Moreover, inhibition of Pin1 by various approaches, including the Pin1 inhibitor, Pin1 antisense polynucleotides, or genetic depletion, kills human and yeast dividing cells by inducing premature mitotic entry and apoptosis. Thus, upon phosphorylation, Pin1 latches onto phosphoproteins and twists the peptide bond next to the proline, which regulates the function of phosphoproteins and participates in controlling the timing of mitotic progression. In addition, Pin1 has been shown to regulate the expression and/or activity of a diverse array of proteins associated with cancer progression. For example, known Pin1 substrates include, without limitation, Her2, PKM2, FAK, Raf-1, AKT, β-catenin, c-Myc, p53, and numerous other proteins known to play roles in cancer progression.

Pin1 in Autoimmune Disease

Elevated Pin1 activity has been associated with the development and progression of autoimmune disorders. For example, Pin1 has previously been shown to act on IRF3 to affect IFN-β production upon TLR3 or RIG-I activation. Recent results have shown that unlike IRF3- or TLR3-deficient mice, IRF7 or IRAK1-deficient mice completely fail to mount a type I IFN antiviral responses due to loss of type I IFN secretion from pDCs. We have determined an essential role for Pin1 as a novel regulator of IRAK1 activation in TLR signaling and type I IFN-mediated innate and adaptive immunity and revealed that Pin1 inhibitors, which are under active development, may represent a novel therapeutic approach that would allow selective inhibition of the type I IFN response while leaving proinflammatory cytokine production unaffected (see, e.g., PCT Publication No. WO 2012/162698).

Inhibitors of Pin1 Activity

The present invention features methods of reducing Pin1 activity in a cell (e.g., a cell present in a subject) using arsenic trioxide and derivatives thereof. In some instances, the cell is contacted to arsenic trioxide in combination with a retinoic acid compound (e.g., as described herein).

Arsenic Trioxide

Arsenic trioxide generally has the following structure:

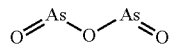

Arsenic trioxide exhibits high toxicity in subjects of the invention, including mammals (e.g., humans). For example, arsenic trioxide ingestion can result in severe side effects, including vomiting, abdominal pain, diarrhea, bleeding, convulsions, cardiovascular disorders, inflammation of the liver and kidneys, abnormal blood coagulation, hair loss, and death. Chronic exposure to even low levels of arsenic trioxide can result in arsenicosis and skin cancer. Arsenic trioxide is therefore desirably administered to a subject at low enough doses to minimize toxicity. Arsenic trioxide and derivatives thereof (e.g., as described herein) may be effective at inducing Pin1 degradation, thereby reducing Pin1 activity levels. Such a reduction in Pin1 activity levels may effectively treat a Pin1-associated disorder (e.g., as described herein) in a subject, for example, according to the methods of the invention. In some instances, arsenic trioxide may operate synergistically with a retinoic acid compound to reduce Pin1 activity levels. In certain instances, the combination of arsenic trioxide and the retinoic acid compound are administered in amounts that result in minimal toxicity.

Retinoic Acid Compounds

Retinoic acid compounds are generally derivatives of the diterpene retinoic acid (e.g., as described herein). The methods described herein utilize retinoic acid compounds to reduce Pin1 activity levels in a cell (e.g., a cell in a subject, such as a human subject). Exemplary retinoic acid compounds that may be effective for reducing Pin1 activity include all-trans retinoic acid (ATRA), 13-cis retinoic acid (13cRA), and retinoic acid compounds, and derivatives thereof, e.g., as described herein. In some instances, a retinoic acid compound is administered in combination with arsenic trioxide. In certain instances, the combination of arsenic trioxide and the retinoic acid compound are administered in amounts that result in minimal toxicity.

Certain embodiments of the invention feature a deuterated retinoic acid compound that is made by replacing some or all hydrogen with deuterium using state of the art techniques (e.g., as described herein and at www.concertpharma.com).

Methods of Treatment

The present invention provides for both prophylactic and therapeutic methods of treating a subject at risk of (or susceptible to) a Pin1-associated disorder (e.g., a disorder associated with elevated Pin1 activity) with arsenic trioxide and/or a retinoic compound.

Certain embodiments of the invention feature formulation of arsenic trioxide for, e.g., controlled or extended release. Many strategies can be pursued to obtain controlled and/or extended release in which the rate of release outweighs the rate of metabolism of the therapeutic compound. For example, controlled release can be obtained by the appropriate selection of formulation parameters and ingredients (e.g., appropriate controlled release compositions and coatings). Examples include single or multiple unit tablet or capsule compositions, oil solutions, suspensions, emulsions, microcapsules, microspheres, nanoparticles, patches, and liposomes. The release mechanism can be controlled such that the arsenic trioxide and/or retinoic acid compound is released at period intervals, the release could be simultaneous, or a delayed release of one of the agents of the combination can be affected, when the early release of one particular agent is preferred over the other.

Prophylactic Methods

In one aspect, the invention provides a method for preventing a Pin1-associated disorder in a subject by administering to the subject arsenic trioxide, optionally in combination with a retinoic acid compound (e.g., as described herein). Subjects at risk for a disease which is caused or contributed to by aberrant Pin1 expression or activity can be identified by, for example, any or a combination of diagnostic or prognostic assays as described herein. Administration of arsenic trioxide and/or a retinoic acid compound can occur prior to the manifestation of symptoms characteristic of the Pin1 aberrancy, such that a Pin1-associated disorder is prevented or, alternatively, delayed in its progression. In some instances, the subject may be monitored after such administration for the appearance or progression of such a disorder.

Combination Therapies

The arsenic trioxide and/or retinoic acid compound(s) of the invention may be further combined with additional therapeutic agents for treatment of a Pin1-associated disorder. The additional therapeutic agents may, in some instances, synergize with the arsenic trioxide and/or retinoic acid compounds to effectively treat the Pin1-associated disorder.

Compounds which are known to interact with other proteins implicated in Pin1 signaling pathways may be useful in combination with arsenic trioxide and/or a retinoic acid compound according to the methods of the invention (see, e.g., the targets and compounds in Table 3).

TABLE 3

Exemplary Additional Therapeutic Agents

| Target | Target Class | Representative Antagonist |
|---|---|---|
| AKT | Kinase | MK-2206 |
| Cyclin D1 | Cyclin | ON 013105 |
| HER2/Neu (ErbB-2) | Kinase | Herceptin |
| NF-κF | Transcription Factor | RTA 402 |
| Plk | Kinase | BI 2536 |
| Raf-1 | Kinase | Sorafenib |
| Stat3 | Transcription Factor | ISIS-STAT3Rx |
| ISIS-STAT | Adhesion | Nucleic Acid-Based Rx in Enzon Program at Santaris |

Such compounds can act synergistically with arsenic trioxide and/or a retinoic acid compound. Additionally, co-administration with arsenic trioxide and/or a retinoic acid compound may result in the efficacy of the additional therapeutic agent at lower and safer doses (e.g., at least 5% less, for example, at least 10%, 20%, 50%, 80%, 90%, or even 95% less) than when the additional therapeutic agent is administered alone.

Proliferative Disorders

In some instances, the arsenic trioxide and/or retinoic acid compounds may be combined with anti-proliferative and other anti-cancer compounds (e.g., anti-angiogenic compounds) for treating proliferative disorders. Anti-proliferative agents that can be used in combination with a retinoic acid compound include, without limitation, microtubule inhibitors, topoisomerase inhibitors, platins, alkylating agents, and anti-metabolites. Exemplary anti-proliferative agents that are useful in the methods and compositions of the invention include, without limitation, paclitaxel, gemcitabine, doxorubicin, vinblastine, etoposide, 5-fluorouracil, carboplatin, altretamine, aminoglutethimide, amsacrine, anastrozole, azacitidine, bleomycin, busulfan, carmustine, chlorambucil, 2-chlorodeoxyadenosine, cisplatin, colchicine, cyclophosphamide, cytarabine, cytoxan, dacarbazine, dactinomycin, daunorubicin, docetaxel, estramustine phosphate, floxuridine, fludarabine, gentuzumab, hexamethylmelamine, hydroxyurea, ifosfamide, imatinib, interferon, irinotecan, lomustine, mechlorethamine, melphalen, 6-mercaptopurine, methotrexate, mitomycin, mitotane, mitoxantrone, pentostatin, procarbazine, rituximab, streptozocin, tamoxifen, temozolomide, teniposide, 6-thioguanine, topotecan, trastuzumab, vincristine, vindesine, and vinorelbine. The ability of a compound to inhibit the growth of a neoplasm can be assessed using known animal models.

Autoimmune Disorders

Anti-inflammatory agents are useful for treating immune disorders in combination with the retinoic acid compounds of the invention. Anti-inflammatory agents that can be used in combination with arsenic trioxide and/or a retinoic acid compound include, without limitation, corticosteroids, NSAIDs (e.g., naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid (salsalate), fenoprofen, flurbiprofen, ketoprofen, meclofenamate sodium, meloxicam, oxaprozin, sulindac, and tolmetin), COX-2 inhibitors (e.g., rofecoxib, celecoxib, valdecoxib, and lumiracoxib), biologics (e.g., inflixamab, adelimumab, etanercept, CDP-870, rituximab, and atlizumab), small molecule immunomodulators (e.g., VX 702, SCIO 469, doramapimod, RO 30201195, SCIO 323, DPC 333, pranalcasan, mycophenolate, and merimepodib), nonsteroidal immunophilin-dependent immunosuppressants (e.g., cyclosporine, tacrolimus, pimecrolimus, and ISAtx247), 5-amino salicylic acid (e.g., mesalamine, sulfasalazine, balsalazide disodium, and olsalazine sodium), DMARDs (e.g., methotrexate, leflunomide, minocycline, auranofin, gold sodium thiomalate, aurothioglucose, and azathioprine), hydroxychloroquine sulfate, and penicillamine.

Infectious Disease

In cases where there is a viral or microbial infection, the compounds of the invention can be administered with an antimicrobial agent, e.g., the penicillins (e.g., penicillin G, ampicillin, methicillin, oxacillin, and amoxicillin), the cephalosporins (e.g., cefadroxil, ceforanid, cefotaxime, and ceftriaxone), the tetracyclines (e.g., doxycycline, minocycline, and tetracycline), the aminoglycosides (e.g., amikacin, gentamycin, kanamycin, neomycin, streptomycin, and tobramycin), the macrolides (e.g., azithromycin, clarithromycin, and erythromycin), the fluoroquinolones (e.g., ciprofloxacin, lomefloxacin, and norfloxacin), and other antibiotics including chloramphenicol, clindamycin, cycloserine, isoniazid, rifampin, and vancomycin. Particularly useful formulations contain aminoglycosides, including for example amikacin, gentamicin, kanamycin, neomycin, netilmicin, paromomycin, streptomycin, and tobramycin, or an antiviral agent, e.g., 1-D-ribofuranosyl-1,2,4-triazole-3 carboxamide, 9→2-hydroxy-ethoxy methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir.

Treatment Regimens

Therapy according to the invention may be performed alone or in conjunction with another therapy and may be provided at home, the doctor's office, a clinic, a hospital's outpatient department, or a hospital. Treatment optionally begins at a hospital so that the doctor can observe the therapy's effects closely and make any adjustments that are needed, or it may begin on an outpatient basis. The duration of the therapy depends on the type of disease or disorder being treated, the age and condition of the patient, the stage and type of the patient's disease, and how the patient responds to the treatment. Additionally, a person having a greater risk of developing a Pin1-associated disorder may receive treatment to inhibit or delay the onset of symptoms.

Routes of administration for the various embodiments include, but are not limited to, topical, transdermal, nasal, and systemic administration (such as, intravenous, intramuscular, subcutaneous, inhalation, rectal, buccal, vaginal, intraperitoneal, intraarticular, ophthalmic, otic, or oral administration). As used herein, "systemic administration" refers to all nondermal routes of administration, and specifically excludes topical and transdermal routes of administration.

In combination therapy (e.g., arsenic trioxide and/or a retinoic acid compound in combination with an additional therapeutic agent), the dosage and frequency of administration of each component of the combination can be controlled independently. For example, one or more of the compounds may be administered three times per day, while another compound or compounds may be administered once per day. Alternatively, one compound may be administered earlier and another compound may be administered later. Combination therapy may be given in on-and-off cycles that include rest periods so that the patient's body has a chance to recover from any as yet unforeseen side effects. The compounds may also be formulated together such that one administration delivers both compounds.

Each compound of the combination may be formulated in a variety of ways that are known in the art. For example, a plurality of therapeutic agents (e.g., arsenic trioxide, a retinoic acid compound, and/or an additional therapeutic agent, as described herein) may be formulated together or separately. In some instances, multiple agents are formulated together for the simultaneous or near simultaneous administration of the agents. Such co-formulated compositions can include the drugs together in the same pill, ointment, cream, foam, capsule, liquid, etc. It is to be understood that, when referring to the formulation of combinations of the invention, the formulation technology employed is also useful for the formulation of the individual agents of the combination, as well as other combinations of the invention. By using different formulation strategies for different agents, the pharmacokinetic profiles for each agent can be suitably matched.

The individually or separately formulated agents can be packaged together as a kit. Non-limiting examples include kits that contain, e.g., a plurality of pills (e.g., two pills or three pills), a pill and a powder, a suppository and a liquid in a vial, two topical creams, ointments, foams etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses), or the kit may contain multiple doses suitable for administration to multiple patients ("bulk packaging"). The kit components may be assembled in cartons, blister packs, bottles, tubes, and the like.

Diagnostics and Prognostics

The present invention pertains to the treatment and prevention of Pin1-associated disorders with arsenic trioxide and/or retinoic acid compounds. In some aspects, the invention features the determination of Pin1 activity and/or marker levels in a subject prior to treatment, for example, in which arsenic trioxide and/or a retinoic acid compound are to be administered in the subpopulation of subjects exhibiting elevated Pin1 activity and/or marker levels. In other aspects, the invention can also feature the measurement of Pin1 activity and/or marker levels subsequent to the administration of retinoic acid compounds in order to evaluate the progress of therapy in treating the Pin1-associated disorder. One aspect of the present invention relates to diagnostic assays for measuring levels of Pin1 marker and/or Pin1 activity in the context of a biological sample (e.g., tumor samples, blood, urine, biopsies, lymph, saliva, phlegm, and pus) to thereby determine whether an individual is a candidate for treatment with a retinoic acid compound. The invention features both treatment of subjects exhibiting symptoms of a Pin1-associated disorder and individuals at risk for developing a Pin1-associated disorder.

In one embodiment, the present invention provides methods for determining Pin1 post-translational modifications. For example, phosphorylation of Pin1 on Ser71 in the catalytic active site by the tumor suppressor DAPK1 completely inhibits Pin1 catalytic activity and cell function to promote oncogenesis. Importantly, phosphorylation of Pin1 on Ser71 in the catalytic active site also prevents retinoic acid compounds from binding to Pin1 active site and induce Pin1 degradation and to inhibit Pin1 function. Therefore, by detecting reduced Ser71 phosphorylation using phosphospecific Pin1 antibodies that we have generated can be a method to select patients for RA treatments and to explain some patients may not respond to RA. Because aberrantly proliferating cells exhibit reduced Ser71 phosphorylation, these cells are more sensitive to RA treatments compared to normal cells.

The methods of the invention can also be used to detect genetic alterations in a Pin1 gene, thereby determining if a subject with the altered gene is at risk for a disorder associated with the Pin1 gene and, consequently, a candidate for treatment with arsenic trioxide and/or a retinoic acid compound. In preferred embodiments, the methods include detecting, in a sample of cells from the subject, the presence or absence of a genetic alteration characterized by at least one of an alteration affecting the integrity of a gene encoding a Pin1-protein, or the mis-expression of the Pin1 gene. For example, such genetic alterations can be detected by ascertaining the existence of at least one of 1) a deletion of one or more nucleotides from a Pin1 gene; 2) an addition of one or more nucleotides to a Pin1 gene; 3) a substitution of one or more nucleotides of a Pin1 gene, 4) a chromosomal rearrangement of a Pin1 gene; 5) an alteration in the level of a messenger RNA transcript of a Pin1 gene, 6) aberrant modification of a Pin1 gene, such as of the methylation pattern of the genomic DNA, 7) the presence of a non-wild type splicing pattern of a messenger RNA transcript of a Pin1 gene, 8) a non-wild type level of a Pin1-protein, 9) allelic loss of a Pin1 gene, and 10) inappropriate post-translational modification of a Pin1-protein. As described herein, there are a large number of assay techniques known in the art which can be used for detecting alterations in a Pin1 gene. A preferred biological sample is a tissue or serum sample isolated by conventional means from a subject, e.g., a cardiac tissue sample.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in the Pin1-gene (see Abravaya et al. (1995) Nucleic Acids Res 0.23:675-682). This method can include the steps of collecting a sample from a patient, isolating nucleic acid (e.g., genomic, mRNA or both) from the sample, contacting the nucleic acid sample with one or more primers which specifically hybridize to a Pin1 gene under conditions such that hybridization and amplification of the Pin1-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli, J. C. et al., (1990) Proc. Natl. Acad. Sci. USA 87:1874-1878), transcriptional amplification system (Kwoh, D. Y. et al, (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a Pin1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in Pin1 can be identified by hybridizing a sample and control nucleic acids, e.g., DNA or RNA, to high density arrays containing hundreds or thousands of oligonucleotides probes (Cronin, M. T. et al. (1996) Human Mutation 7: 244-255; Kozal, M. J. et al. (1996) Nature Medicine 2: 753-759). For example, genetic mutations in Pin1 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the Pin1 gene and detect mutations by comparing the sequence of the sample Pin1 with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Biotechniques 19:448), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the Pin1 gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type Pin1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with 51 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Nat Acad Sci USA 85:4397; Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in Pin1 cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on a Pin1 sequence, e.g., a wild-type Pin1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in Pin1 genes. For example, single strand conformation polymorphism (SSCP) may be used to detect differences in electrophoretic mobility between mutant and wild type nucleic acids (Orita et al. (1989) Proc Natl. Acad. Sci. USA: 86:2766, see also Cotton (1993) Mutat Res 285:125-144; and Hayashi (1992) Genet Anal Tech Appl 9:73-79). Single-stranded DNA fragments of sample and control Pin1 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl Acad. Sci USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner et al. (1993) Tibtech 11:238). In addition it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits including at least one probe nucleic acid or antibody reagent described herein, which may be conveniently used, e.g., in clinical settings to diagnose patients exhibiting symptoms or family history of a disease or illness involving a Pin1 gene. Additional methods of detecting Pin1 activity and diagnosing Pin1-associated disorders are disclosed in U.S. Patent Application Publication Nos.: 2009/0258352, 2008/0214470, 2006/0074222, 2005/0239095, US2002/0025521, U.S. Pat. No. 6,495,376, and PCT Application Publication No. WO02/065091.

The present invention also features methods and compositions to diagnose, treat and monitor the progression of a disorder described herein (e.g., a Pin-1 associated disorder) by detection and measurement of, for example, Pin1 substrates (or any fragments or derivatives thereof) containing a phosphorylated Ser/Thr-Pro motif in a cis or trans conformation, e.g., as described in PCT Publication No. WO2012/125724. The methods can include measurement of absolute levels of the Pin1 substrate (examples of which are listed in Table 4) in a cis or trans conformation as compared to a normal reference, using conformation specific antibodies. For example, a serum level or level in a biopsy of a Pin1 substrate in the cis or trans conformation that is less than 5 ng/ml, 4 ng/ml, 3 ng/ml, 2 ng/ml, or less than 1 ng/ml serum or a biopsy is considered to be predictive of a good outcome in a patient diagnosed with a disorder (e.g., a disorder associated with a deregulation of Pin1 activity). A serum level of the substrate in the cis or trans conformation that is greater than 5 ng/ml, 10 ng/ml, 20 ng/ml, 30 ng/ml, 40 ng/ml, or 50 ng/ml is considered diagnostic of a poor outcome in a subject already diagnosed with a disorder, e.g., associated with a deregulation of Pin1 activity.

For diagnoses based on relative levels of substrate in a particular conformation (e.g., a Pin1 substrate in the cis or trans conformation), a subject with a disorder (e.g., a disorder associated with a deregulation of PPIase activity) will show an alteration (e.g., an increase of 10%, 20%, 30%, 40%, 50%, 60%, 70%, 80%, 90%, or more) in the amount of the substrate in, for example, the cis conformation. A normal reference sample can be, for example, a prior sample taken from the same subject prior to the development of the disorder or of symptoms suggestive of the disorder, a sample from a subject not having the disorder, a sample from a subject not having symptoms of the disorder, or a sample of a purified reference polypeptide in a given conformation at a known normal concentration (i.e., not indicative of the disorder).

Standard methods may be used to measure levels of the substrate in any bodily fluid, including, but not limited to, urine, blood, serum, plasma, saliva, amniotic fluid, or cerebrospinal fluid. Such methods include immunoassay, ELISA, Western blotting, and quantitative enzyme immunoassay techniques.

For diagnostic purposes, the conformation-specific antibodies may be labeled. Labeling of the antibody is intended to encompass direct labeling of the antibody by coupling (e.g., physically linking) a detectable substance to the antibody, as well as indirect labeling the antibody by reacting the antibody with another reagent that is directly labeled. For example, the antibody can be labeled with a radioactive or fluorescent marker whose presence and location in a subject can be detected by standard imaging techniques.

The diagnostic and prognostic methods described herein can be used individually or in combination with any other diagnostic method described herein for a more accurate diagnosis of the presence or severity of a disorder (e.g., a cellular proliferation disorder or a neurological disorder). Examples of additional methods for diagnosing such disorders include, e.g., examining a subject's health history, immunohistochemical staining of tissues, computed tomography (CT) scans, or culture growths.

Diagnostic Assays

Diagnostic assays can be carried out in, e.g., subjects diagnosed or at risk of a Pin1-associated disorder (e.g., as described herein), which may be used to identify subjects that may be effectively treated with arsenic trioxide and/or a retinoic acid compound, for example, according to the methods of the invention. Pin1 activity levels can be determined, for example, by measuring the quantity of Pin1 protein and/or a nucleic acid encoding Pin1 in a sample (e.g., a sample obtained from a subject). An exemplary method for detecting the presence or absence of Pin1 protein or nucleic acid in a biological sample involves obtaining a biological sample from a test subject and contacting the biological sample with a compound or an agent capable of detecting Pin1 protein or a nucleic acid (e.g., mRNA, genomic DNA) that encodes Pin1 protein such that the presence of Pin1 protein or nucleic acid is detected in the biological sample. A preferred agent for detecting Pin1 mRNA or genomic DNA is a labeled nucleic acid probe capable of hybridizing to Pin1 mRNA or DNA. The nucleic acid probe can be, for example, a Pin1 nucleic acid or a corresponding nucleic acid such as an oligonucleotide of at least 15, 30, 50, 100, 250 or 500 nucleotides in length which is capable of specifically hybridizing under stringent conditions to Pin1 mRNA or genomic DNA. Other suitable probes for use in the diagnostic assays of the invention are described herein.

A preferred agent for detecting Pin1 marker is an antibody capable of binding to Pin1 protein, preferably an antibody with a detectable label. Antibodies can be polyclonal, or more preferably, monoclonal. An intact antibody, or a fragment thereof (e.g., Fab or F(ab')2) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

With respect to antibody-based detection techniques, one of skill in the art can raise anti-Pin1 antibodies against an appropriate immunogen, such as isolated and/or recombinant Pin1 or a portion or fragment thereof (including synthetic molecules, such as synthetic peptides) using no more than routine experimentation. Synthetic peptides can be designed and used to immunize animals, such as rabbits and mice, for antibody production. The nucleic and amino acid sequence of Pin1 is known (Hunter et al., WO 97/17986 (1997); Hunter et al., U.S. Pat. Nos. 5,952,467 and 5,972,697) and can be used to design nucleic acid constructs for producing proteins for immunization or in nucleic acid detection methods or for the synthesis of peptides for immunization.

Conditions for incubating an antibody with a test sample can vary depending upon the tissue or cellular type. Incubation conditions can depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques," Elsevier Science Publishers, Amsterdam, The Netherlands (1986); Bullock et al., "Techniques in Immunocytochemistry," Academic Press, Orlando, Fla. Vol. 1 (1982), Vol. 2 (1983), Vol. 3 (1985); Tijssen, "Practice and Theory of enzyme Immunoassays: Laboratory Techniques in Biochemistry and Molecular Biology," is Elsevier Science Publishers, Amsterdam, The Netherlands (1985).

The detection method of the invention can be used to detect Pin1 mRNA, protein, or genomic DNA in a biological sample in vitro as well as in vivo. For example, in vitro techniques for detection of Pin1 mRNA include Northern hybridizations and in situ hybridizations. In vitro techniques for detection of Pin1 protein include enzyme linked immunosorbent assays (ELISAs), Western blots, immunoprecipitations, immunofluorescence, or quantitative sequencing reactions. In vitro techniques for detection of Pin1 genomic DNA include Southern hybridizations. The detection of genomic mutations in Pin1 (or other genes that effect Pin1 marker levels) can be used to identify inherited or somatic mutations. Furthermore, in vivo techniques for detection of Pin1 protein include introducing into a subject a labeled anti-Pin1 antibody. For example, the antibody can be labeled with a radioactive marker whose presence and location in a subject can be detected by standard imaging techniques.

In another embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting Pin1 marker such that the presence of Pin1 marker is detected in the biological sample, and comparing the presence of Pin1 marker in the control sample with the presence of Pin1 marker in the test sample.

The immunological assay test samples of the present invention may include cells, protein or membrane extracts of cells, blood or biological fluids such as ascites fluid or brain fluid (e.g., cerebrospinal fluid). The test sample used in the above-described method is based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized. The invention also encompasses kits for detecting the presence of Pin1 in a biological sample. For example, the kit can include a labeled compound or agent capable of detecting Pin1 protein or mRNA in a biological sample; means for determining the amount of Pin1 in the sample; and means for comparing the amount of Pin1 in the sample with a standard. The compound or agent can be packaged in a suitable container. The kit can further include instructions for using the kit to detect Pin1 protein or nucleic acid.

Pin1 activity and/or marker levels can also be measured in an assay designed to evaluate a panel of target genes, e.g., a microarray or multiplex sequencing reaction. In the embodiments of the invention described herein, well known biomolecular methods such as northern blot analysis, RNase protection assays, southern blot analysis, western blot analysis, in situ hybridization, immunocytochemical procedures of tissue sections or cellular spreads, and nucleic acid amplification reactions (e.g., polymerase chain reactions) may be used interchangeably. One of skill in the art would be capable of performing these well-established protocols for the methods of the invention. (See, for example, Ausubel, et al., "Current Protocols in Molecular Biology," John Wiley & Sons, NY, N.Y. (1999)).

Prognostic Assays

The diagnostic methods described herein can furthermore be utilized to identify subjects having or at risk of developing a Pin1-associated disorder, which may be effectively treated with arsenic trioxide and/or a retinoic acid compound according to the methods of the invention. For example, the assays described herein, such as the preceding diagnostic assays or the following assays, can be utilized to identify a subject having or at risk of developing a disorder associated with elevated levels of Pin1 activity. Thus, the present invention provides a method for identifying a disease or disorder associated with aberrant Pin1 expression or activity in which a test sample is obtained from a subject and Pin1 protein or nucleic acid (e.g., mRNA, genomic DNA) is detected, wherein the presence of Pin1 protein or nucleic acid is diagnostic for a subject having or at risk of developing a Pin1-associated disorder and are, therefore, susceptible to treatment with a retinoic acid compound.

Furthermore, the present invention provides methods for determining whether a subject can be effectively treated with a retinoic acid compound for a disorder associated with aberrant Pin1 expression or activity in which a test sample is obtained and Pin1 protein or nucleic acid expression or activity is detected (e.g., wherein the abundance of Pin1 protein or nucleic acid expression or activity is diagnostic for a subject that can be administered the agent to treat a disorder Pin1-associated disorder).

Monitoring the Effects of Retinoic Acid Treatment, and Disease Progression

In one embodiment, the present invention features a method for monitoring the effectiveness of treatment of a subject with arsenic trioxide and/or a retinoic acid compound including the steps of (i) obtaining a pre-administration sample from a subject prior to administration of arsenic trioxide and/or a retinoic acid compound; (ii) detecting the level of expression or activity of a Pin1 protein, Pin1 phosphorylation on Ser71, mRNA, or genomic DNA in the pre-administration sample; (iii) obtaining one or more post-administration samples from the subject; (iv) detecting the level of expression or activity of the Pin1 protein, mRNA, or genomic DNA in the post-administration samples; (v) comparing the level of expression or activity of the Pin1 protein, mRNA, or genomic DNA in the pre-administration sample with the Pin1 protein, mRNA, or genomic DNA in the post administration sample or samples; and (vi) altering the administration of arsenic trioxide and/or a retinoic acid compound to the subject accordingly. According to such an embodiment, Pin1 expression, phosphorylation or activity may be used as an indicator of the effectiveness of the arsenic trioxide and/or a retinoic acid compound, even in the absence of an observable phenotypic response.

In another embodiment, the diagnostic methods described herein can also be used to measure the levels of, for example, polypeptides (e.g., Pin1 substrates listed in Table 4) with pSer/Thr-Pro motifs in the cis or trans conformation using conformation specific antibodies, The methods can include repeated measurements, using conformation specific antibodies, for diagnosing the disorder and monitoring the treatment or management of the disorder. In order to monitor the progression of the disorder in a subject, subject samples can be obtained at several time points and conformation specific antibodies can be used to monitor the levels of cis and trans isomers of Pin1 substrates (listed in Table 4). For example, the diagnostic methods can be used to monitor subjects during therapy with arsenic trioxide and/or a retinoic acid compound or other agent described herein. In this example, serum samples from a subject can be obtained before treatment, again during treatment, and again after treatment. In this example, the level of Pin1 substrate with a pSer/Thr-Pro motif in the cis conformation in a subject is closely monitored using the conformation-specific antibodies of the invention and, if the level of Pin1 substrate with a pSer/Thr-Pro motif in the cis conformation begins to increase during therapy, the therapeutic regimen for treatment of the disorder can be modified as determined by the clinician (e.g., the dosage of the therapy may be changed or a different therapeutic may be administered). The monitoring methods of the invention may also be used, for example, in assessing the efficacy of a particular drug or therapy in a subject, determining dosages, or in assessing progression, status, or stage of an infection.

TABLE 4

Exemplary Pin1 Substrates

| Substrates | Targeted sites | Consequences |
|---|---|---|
| Signal transduction | | |
| RAF1 | Multiple pS/T-P | Increase dephosphorylation, prolong activation |
| HER2 | Unknown | Increase stability |
| eNOS | pS116-P | Inhibit activity |
| SMAD2/3 | Multiple pS/T-P | Decrease stability |
| Notch1 | pT2512 | Increased processing, stability and activation |
| Notch3 | Unknown | Increased processing, stability and activation |
| AKT | pT92/450-P | Increased stability |
| FAK | pS910-P | Increase dephosphorylation |
| P70S6K | Unknown | Increased activity |
| PTP-PEST | p S571-P | Increase dephosphorylation |
| MEK1 | Unknown | Increase activity |
| GRK2 | pS670-p | Decrease stability |
| CDK10 | p133-P | Decrease stability |
| FBXW7 | pT205-P | Decrease stability |
| PIP4Ks | pT322/S326-P | Inhibit kinase activity |
| PKM2 | pS37-P | Increase nuclear localization |
| JNK1 | pT183-P | Decrease dephosphorylation |
| Gene transcription | | |
| SIN3-RPD3 | Unknown | Reducing histone deacetylases |
| JUN | pS63/73-P | Increase transactivation |
| β-catenin | pS246-P | Increase stability and transactivation |
| CF-2 | Unknown | Destabilization |
| hSPT5 | Unknown | Unknown |
| MYC | pT58-P | Increase expression, stability and transactivation |
|  | pT58/S62-P | Decrease stability |
| NF-κB | pT254-P | Increase stability and transactivation |
| FOS | Multiple S/T-P | Increase transactivation |
| RARα | pS77-P | Decrease stability and transactivation |
| SRC-3/AIB1 | Unknown | Increase transactivation |
| STAT3 | p S727-P | Increased transactivation |
| MYB | pS528-P | Increase transactivation |
| SMRT | pS1241/1469-P | Decrease stability |
| FOXO4 | Unknown | Decrease stability |
| KSRP | Unknown | Increase dephosphorylation and activation |
| SF-1 | pS203-P | Increase transactivation |
| Nanog | Multiple pS/T-P | Increased stability |
| PML | Multiple pS/T-P | Decrease stability |
| Mutant p53 | Unknown | Increased stability and activity |
| ΔNp63 | pT538-P equivalent | Increased stability and activity |
| Oct4 | p S12-P | Increased stability |
| ERα | p S118/294-P | Increase stability, DNA binding and transactivation |
| PKM2 | pS37-P | Increase nuclear localization |
| AR | pS81-P | Increase activity |
| SUV39H1 | pS391-P | Decrease stability |
| RUNX3 | Multiple pS/T-P | Decrease stability |
| KLF10 | pT93-P | Decrease stability |
| Osterix | pS76/80-P | Increased stability |
| PML-RARα | pS581-P | Increase stability |
| Cell cycle at the G1/S | | |
| Cyclin D1 | pT286-P | Increase stability and nuclear localization |
| KI67 | pT234-P | Unknown |
| Cyclin E | pS384-P | Decrease stability |
| p27 | pT187 | Increase stability |
| LSF | pS291/309/p Thr-P | Increase dephosphorylation |
| RB1 | S608/612-P | Increased phosphorylation and inhibit activity |

TABLE 4-continued

Exemplary Pin1 Substrates

| Substrates | Targeted sites | Consequences |
|---|---|---|
| Cell cycle at the G2/M and M | | |
| NIMA | Unknown | Regulate mitotic function |
| RAB4 | Unknown | |
| CDC25 | pThr48/67-P | Increase dephosphorylation and regulate activity |
| WEE1 | pT186-P | Inhibit Wee1 activity |
| PLK1 | Unknown | Unknown |
| MYT1 | Unknown | Unknown |
| CDC27 | Unknown | Unknown |
| CENP-F | Unknown | Unknown |
| INCENP | Unknown | Unknown |
| RPB1 | pS5-P | Regulate CTD dephosphorylation and activity |
| NHERF-1 | pS279/301-P | Increase dephosphorylation |
| KRMP1 | pT-1604-P | Regulate mitotic function |
| CK2 | Multiple pS/T-P | Inhibit kinase activity |
| TOPIIa | Unknown | Unknown |
| DAB2 | pT-1342 | Increase phosphorylation |
| p54NRB | Multiple pT-P | Unknown |
| SIL | Multiple pS/T-P | Regulate function |
| EMI1 | pS10-P | Increase stability |
| CEP55 | Unknown | Increase stability |
| BORA | pS274/278-P | Increase stability |
| Survivin | pT34-P | Increase activity |
| SEPT9 | Unknown | Increase activity |
| SP1 | pT739-P | Increase stability |
| SWI6 | Unknown | Increase nuclear localization |
| WHI5 | Unknown | Increase nuclear localization |
| Separase | Unknown | Increase stability and activity |
| DNA damage/stress response and apoptosis | | |
| p53 | Multiple pS/T-P | Increased stability and transactivation |
| BCL-2 | pS70/87-P | Unknown |
| p73 | Multiple pS/T-P | Increased stability and transactivation |
| BIMEL | pS65-P | Increased stability |
| p66SHC | Unknown | Increase mitochondrial import |
| DAXX | pS178-P | Decrease stability |
| MCL-1 | pT92/T163 | Increase stability |
| NUR77 | pS152-P | Increased transactivation |
| HIPK2 | pT880/882-P | Increased stability |
| RBBP8 | pS276/T315-P | Increased stability |
| p63 | pT538-P | Increased stability |
| HSF1 | pS326-P | Increase levels and activity |
| HIF-1α | Unknown | Increased transactivation |
| CHE-1 | pT144-P | Decrease stability |
| PGK1 | pS203-P | Increase mitochondrial translocation |
| Immune response | | |
| NFAT | Unknown | Unknown |
| AUF1 | Unknown | Protein interaction |
| IRF3 | pS339-P | Decrease stability |
| BTK | pS21/115-P | Decrease stability |
| BAX | p T167-P | Inhibit mitochondrial import |
| COX-2 | Unknown | Increase stability and expression |
| p47PHOX | pS345-P | Increase phosphorylation |
| IRAK1 | pS110/163/196-P | Increase activation |
| GR | pS203/211-P | Increased transactivation |
| FADD | pS194-P | Increase dephosphorylation |
| Viral or parasitic infection and transformation | | |
| HBX | pS41-P | Increase stability and activity |
| A3G | Unknown | Decrease protein stability and release inhibition |
| v-Rel | Unknown | Increase stability and activity |
| Tax | pS160-P | Increase stability and activity |
| Capsid protein | pS16-P | Increase capsid dissociation from the HIV-1 core |
| Integrase | pS57-P | Increase stability and activity |
| BALF5 | pT178-P | Increase viral replication |
| RTA | Unknown | Increase activity |
| FBXW7* | Unknown | Decrease stability |
| ORF1p | Multiple pS/T-P | Regulate L1 retrotransposition |
| Neuronal survival and degeneration | | |
| TAU | pT231-P | Dephosphorylation, Protein interaction |
| APP | pT668-P | Promote non-amyloidogenic APP processing |
| Synphilin-1 | pS211/215-P | Protein interaction |
| Gephyrin | pS188/194/200-P | Protein interaction |
| mGluR5 | pS1126-P | Increase its activity |

TABLE 4-continued

Exemplary Pin1 Substrates

| Substrates | Targeted sites | Consequences |
| --- | --- | --- |
| REST | pS861/864-P | Decrease stability |
| GRO/TLE1 | | Inhibit its activity |
| CRMP2A | pS27-P | Increase stability |

*Theileria* parasites secrete Pin1 homolog to act on the host cellular protein FBW7.

Additional examples of Pin1 substrates include the Pin1 substrates and/or Pin1 targets described, for example, in PCT Publication No. WO2012/125724, Zhou et al. (*Nat. Rev. Cancer* 16(7): 463-478, 2016), and Hunter et al. (*Cell Res.* 24: 1033-1049, 2014), each of which is incorporated herein by reference.

The following examples are intended to illustrate, rather than limit, the scope of invention.

EXAMPLES

Example 1. ATO Inhibits Pin1 Activity in a Dose-Dependent Manner

Recombinant Pin1 was incubated in vitro with increasing concentrations of arsenic trioxide (ATO). Dose-responsive inhibition of Pin1 activity (e.g., Pin1 enzymatic activity) was observed with increasing concentrations of arsenic trioxide (FIG. 1).

Pin1 activity (e.g., Pin1 enzymatic activity) was determined by a chymotrypsin-coupled PPIase assay. Chymotrypsin cleaves only the trans form of the Xaa-Pro bond in a model peptide, such as N-succinyl-Ala-Glu-Pro-Phe-p-nitroanilide. In aqueous solution, approximately 90% of the Xaa-Pro bond of this molecule is in trans-conformation. After addition of an excess amount of chymotrypsin, the trans form of Xaa-Pro bond is rapidly cleaved. The rate of hydrolysis of the remaining 10% Xaa-Pro bond is limited by its rate of cis-to-trans isomerization (e.g., Pin1 activity). Therefore, Pin1 activity is measured by the rate of release of p-nitroanilide by spectrophotometry.

Figure 2:
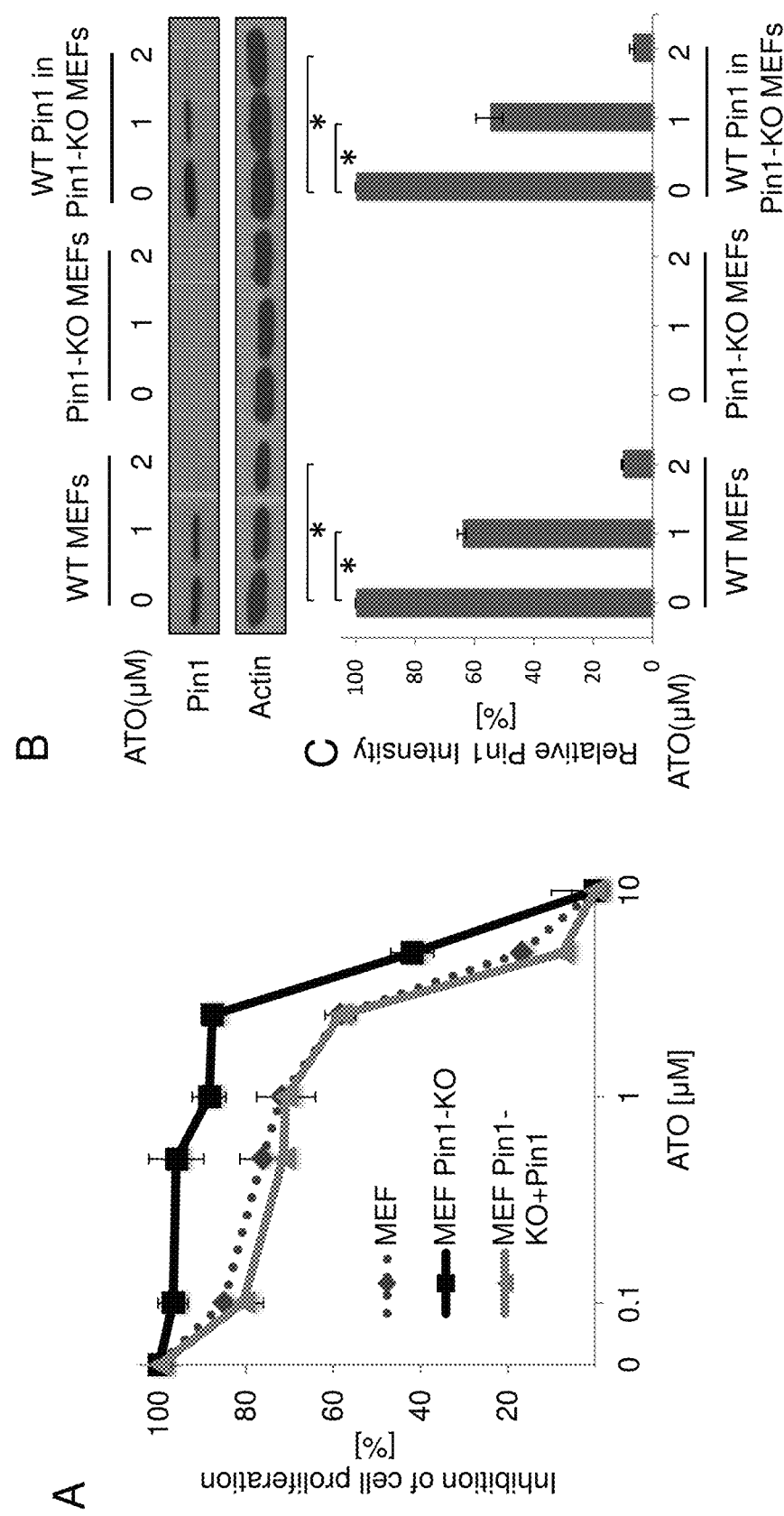
FIG. 2A-2C are images which show that a Pin1 knockout (Pin1 KO) is more resistant to arsenic trioxide, but can be rescued by restoring Pin1 expression.

Example 2. ATO Inhibits Cell Growth and Induces Pin1 Protein Degradation in a Dose-Dependent Manner in MEFs Three populations of mouse embryonic fibroblast cells (MEFs) including, wild-type (WT), Pin1 knockout (Pin1-KO), or Pin1 knockout reconstituted with Pin1 (WT Pin1 in Pin1-KO) were treated with different concentrations of ATO. Cell growth was assayed by counting cell number (FIG. 2A), and Pin1 protein expression levels were determined by immunoblotting (FIG. 2B), with quantification of corresponding Pin1 protein levels (FIG. 2C). The Pin1-KO population was more resistant to inhibition of cellular proliferation as compared to WT cells. Reintroduction of WT Pin1 (WT Pin1 in Pin1-KO) rescued sensitivity to treatment with ATO.

Figure 3:
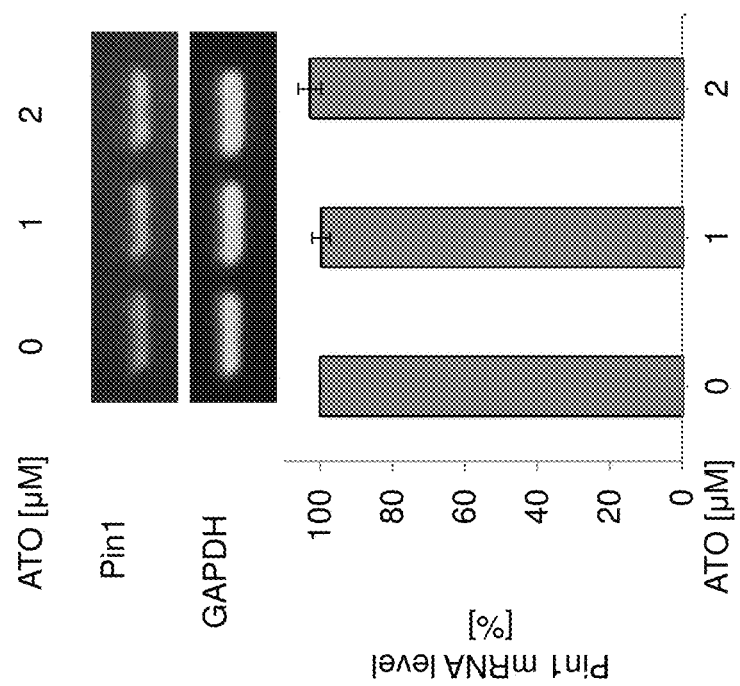
FIG. 3 is an RNA gel image and a corresponding graph of quantified mRNA expression level showing that treatment of Pin1 with arsenic trioxide does not affect Pin1 mRNA levels in MEF cells.

The effect of ATO on Pin1 mRNA levels in MEFs was also determined (FIG. 3). WT MEFs were treated with different concentrations of ATO, followed by assaying Pin1 mRNA levels using realtime PCR. ATO did not affect Pin1 mRNA levels in MEFs.

Figure 4:
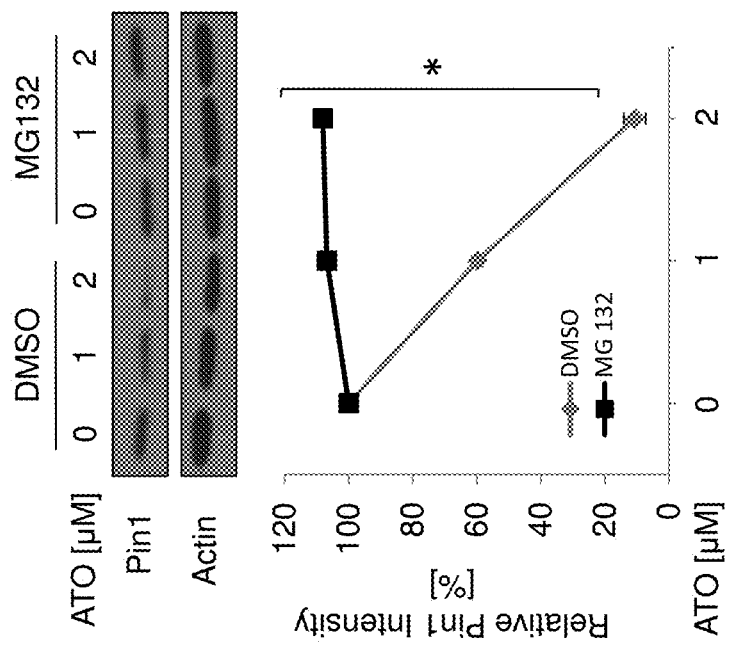
FIG. 4 is a western blot and corresponding graph of quantified protein expression levels showing that, in MEFs, arsenic trioxide-induced Pin1 degradation is blocked by the proteasome inhibitor, MG132.

Example 3. Proteasome Inhibitor, MG-132, Inhibits ATO-Induced Pin1 Degradation in MEFs WT MEFs were treated with increasing concentrations of ATO in the presence of the proteasome inhibitor MG132 or vehicle control DMSO. MEF cells were collected and lysed and levels of Pin1 protein expression were quantified by immunoblotting. The ability of ATO to induce Pin1 degradation was fully rescued by inhibition of the proteasome pathway using proteasome inhibitor, MG132, in MEFs (FIG. 4).

Figure 5:
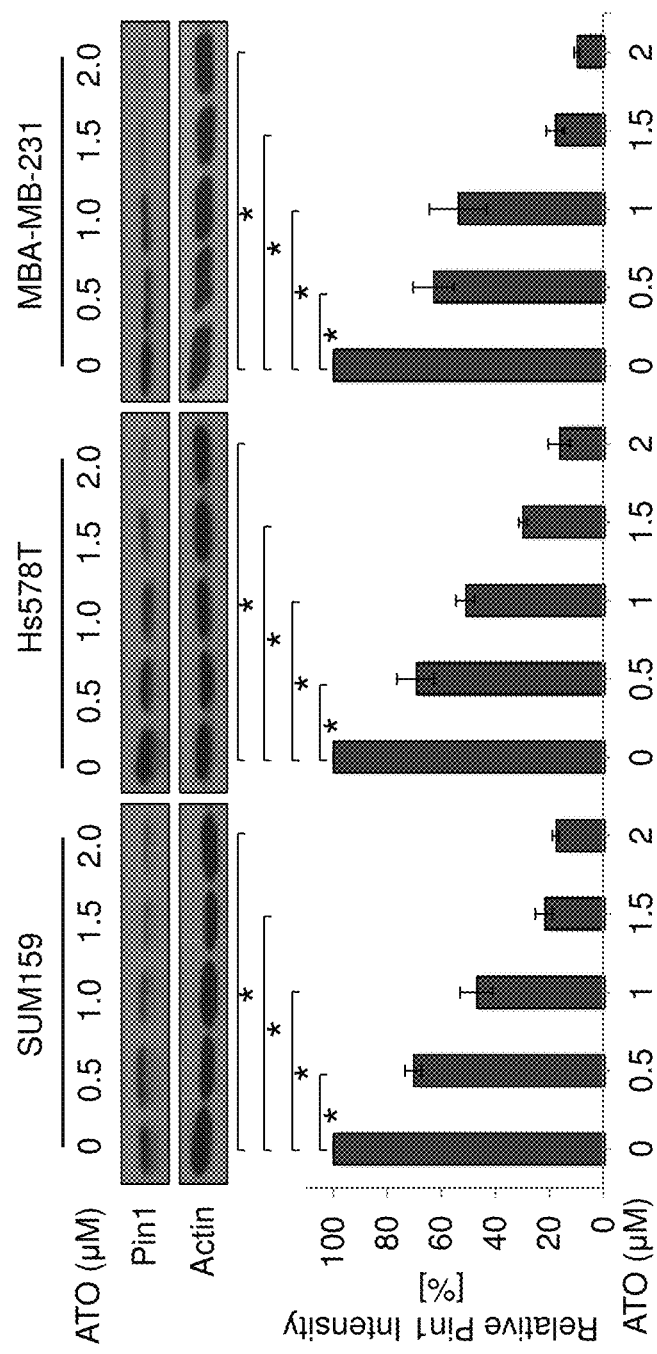
FIG. 5 is a series of western blots and corresponding graphs of quantified protein expression depicting arsenic trioxide-induce Pin1 degradation in triple-negative breast cancer cell lines (SUM159, Hs578T, and MBA-MB-231).

Example 4. ATO Induces Pin1 Degradation in Human Triple-Negative Breast Cancer Cell Lines Three different human triple negative breast cancer cell lines (SUM159, Hs578T and MBA-MB-231) were treated with increasing concentrations of ATO, followed by assaying Pin1 levels using immunoblotting. ATO induced Pin1 degradation in a dose-dependent manner in human triple negative breast cancer cells (FIG. 5).

Figure 6:
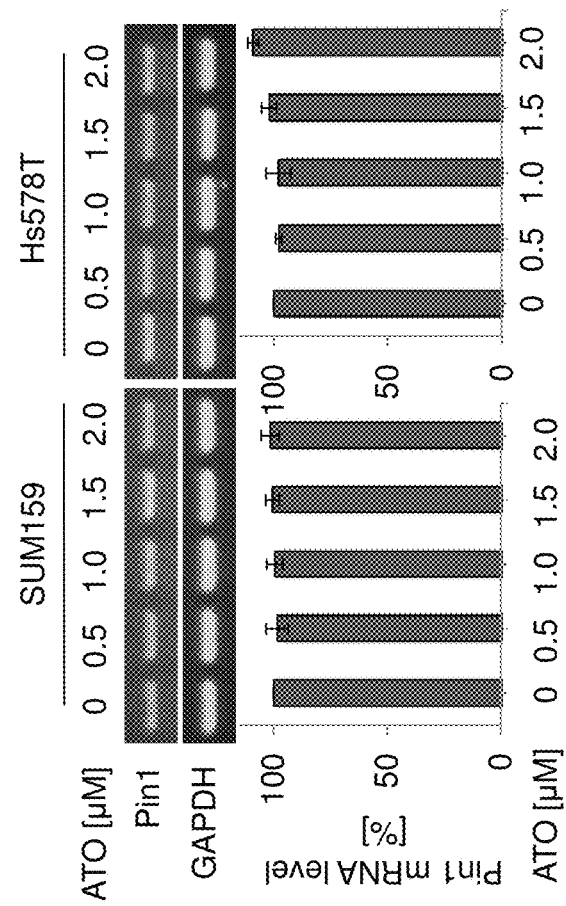
FIG. 6 is a series of RNA gel images and corresponding graphs of quantified mRNA expression levels showing that treatment with arsenic trioxide does not affect Pin1 mRNA levels in triple-negative breast cancer cell line (SUM159 and Hs578T).

Two different human triple negative breast cancer cell lines (SUM159 and Hs578T) were treated with different concentrations of ATO, followed by assaying Pin1 mRNA levels using realtime PCR. ATO did not affect Pin1 mRNA levels in human triple negative breast cancer cells (FIG. 6).

Figure 7:
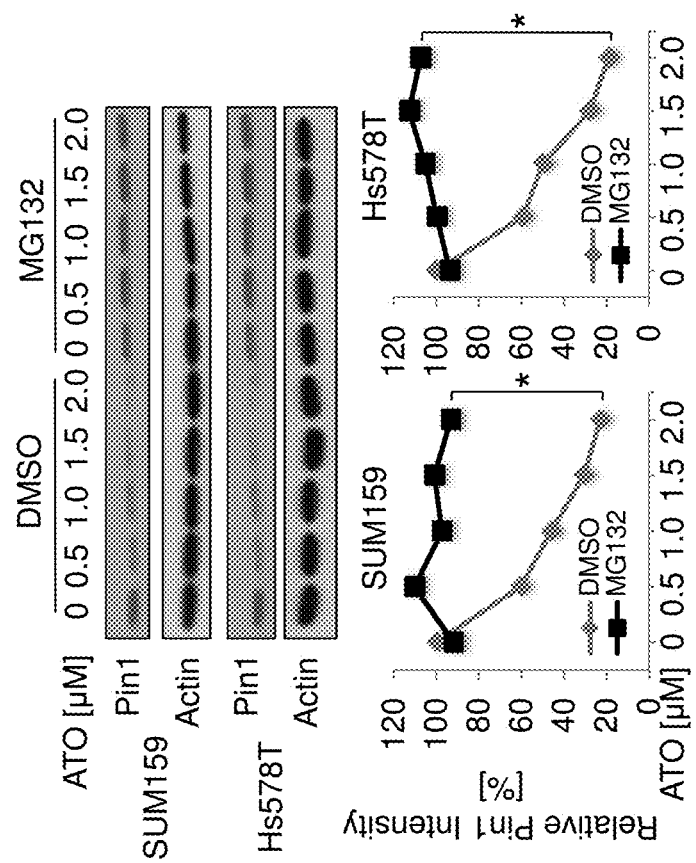
FIG. 7 is a series of western blots and corresponding graphs of quantified protein expression levels showing that, in triple-negative breast cancer cell lines (SUM159 and Hs578T), arsenic trioxide-induced Pin1 degradation is blocked by the proteasome inhibitor, MG132.

Two different human triple negative breast cancer cell lines (SUM159 and Hs578T) were treated with different concentrations of ATO in the presence of the proteasome inhibitor MG132 or vehicle control DMSO. MEF cells were collected and lysed and levels of Pin1 protein expression were quantified by immunoblotting. The ability of ATO to induce Pin1 degradation was fully rescued by inhibition of the proteasome pathway using MG132 in human triple negative breast cancer cells (FIG. 7).

Figure 8:
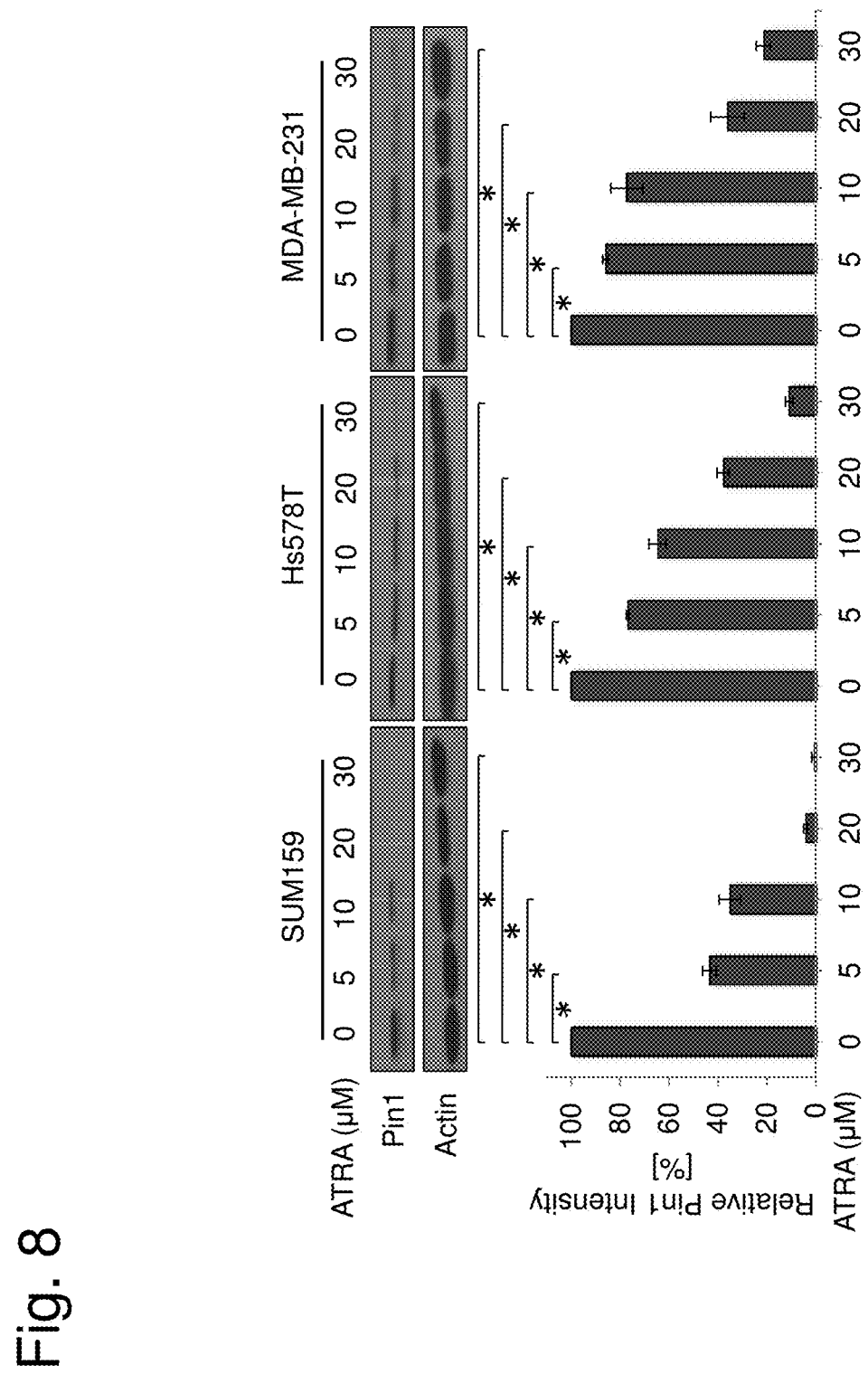
FIG. 8 is a series of western blots and corresponding graphs of quantified protein expression levels showing that all-trans retinoic acid (ATRA) induces Pin1 degradation in triple-negative breast cancer cell lines (SUM159, Hs578T, and MBA-MB-231).
Figure 9:
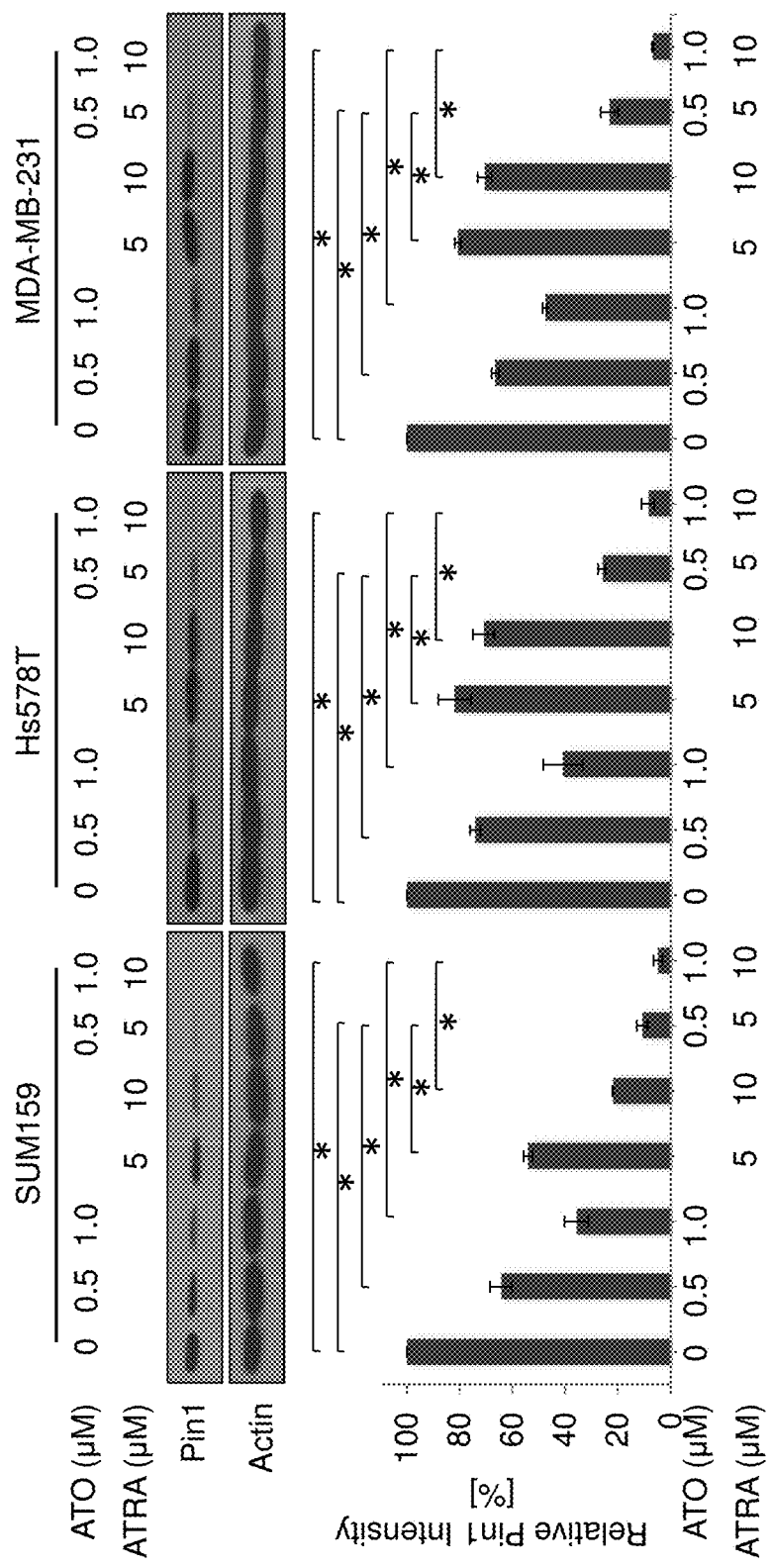
FIG. 9 is a series of western blots and corresponding graphs of quantified protein expression levels depicting decrease in Pin1 protein expression in triple-negative breast cancer cells (SUM159, Hs578T, and MBA-MB-231) following combination treatment with ATO and ATRA, as compared to treatment with either ATO or ATRA, alone.

Example 5. ATRA Induces Pin1 Degradation in Human Triple-Negative Breast Cancer Cell Lines Three different human triple negative breast cancer cell lines (SUM159, Hs578T and MBA-MB-231) were treated with different concentrations of all-trans retinoic acid (ATRA), followed by assaying Pin1 levels using immunoblotting. ATRA induced Pin1 degradation in a dose-dependent manner in human triple negative breast cancer cells (FIG. 8).

Figure 10:
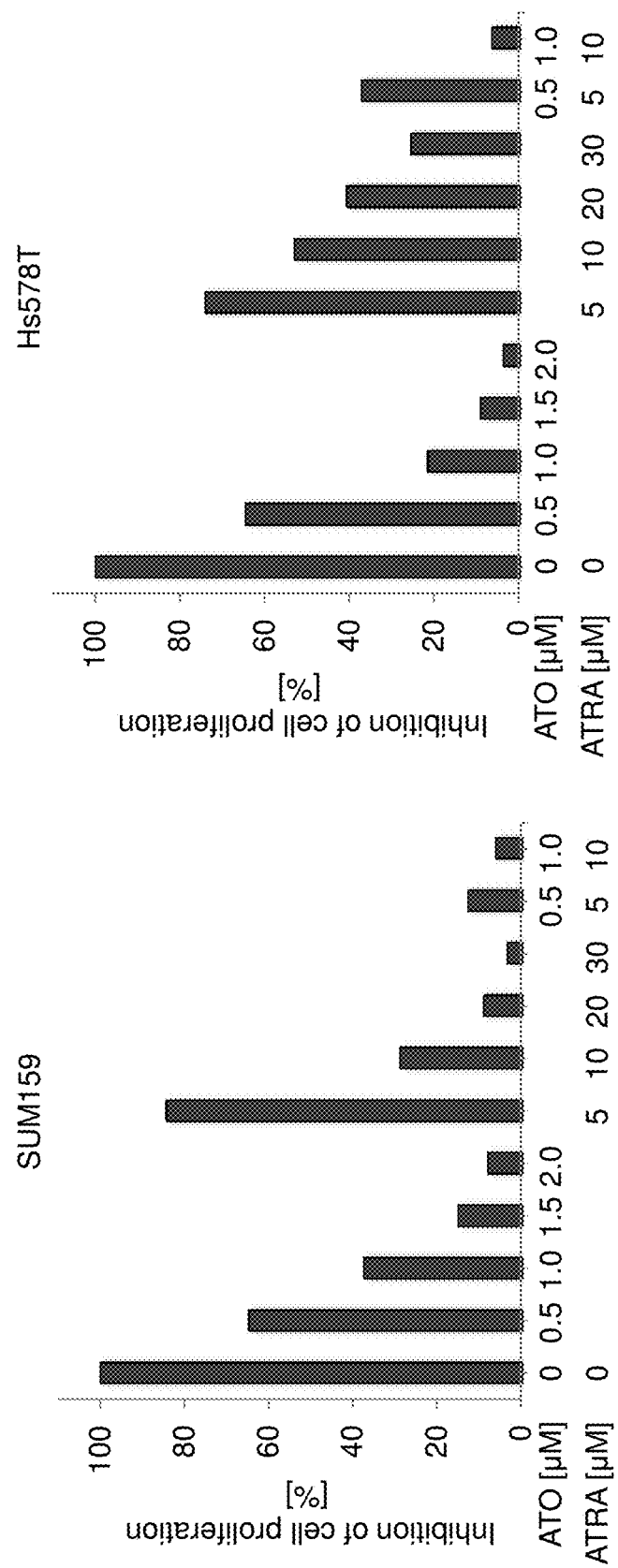
FIG. 10 is a set of graphs depicting an increase in inhibition of cell proliferation in triple-negative breast cancer cells (SUM159, Hs578T) following combination treatment with ATO and ATRA, as compared to treatment with either ATO or ATRA, alone.

Example 6. Administration of ATO and ATRA Synergistically Induces Pin1 Degradation and Inhibits Cell Proliferation in Human Triple-Negative Breast Cancer Cell Lines Three different human triple negative breast cancer cell lines (SUM159, Hs578T and MBA-MB-231) were treated with different concentrations of ATO or ATRA, or were treated with different concentrations of both ATO and ATRA. Pin1 levels were assayed by immunoblotting. The combination of ATO and ATRA synergistically induced Pin1 degradation in human triple negative breast cancer cells, as compared to treatment with equivalent amounts of either ATO or ATRA alone (FIG. 10).

Figure 11:
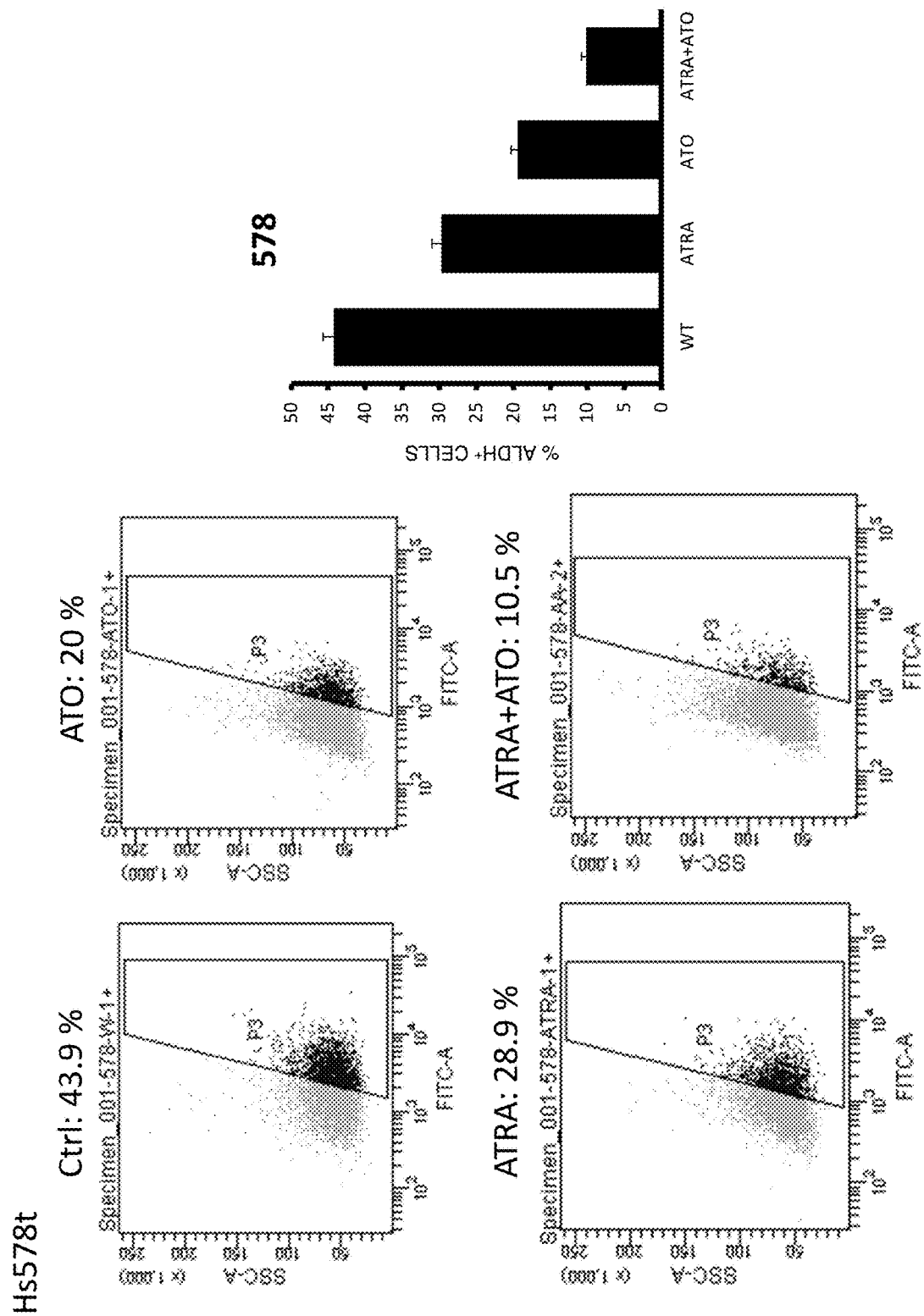
FIG. 11 is a series of plots generated by fluorescence-activated cell sorting (FACS) and a corresponding graph that depicts the quantification of aldehyde dehydrogenase-positive (ALDH+) cells following treatment with ATRA, ATO, or a combination of ATRA and ATO. ALDH is tumor marker associated with breast cancer stem cells. The fraction of ALDH+ cells is decreased in Hs578T cells treated with ATRA+ATO, as compared to those treated with either ATRA or ATO, alone.

Two different human triple negative breast cancer cell lines (SUM159 and Hs578T) were treated with different concentrations of ATO or ATRA separately, or were treated with different concentrations of both ATO and ATRA. Cell growth was assayed by counting cell number. The combination of ATO and ATRA synergistically inhibited cell growth of human triple negative breast cancer cells, as compared to treatment with equivalent amounts of either ATO or ATRA alone (FIG. 11).

Figure 12:
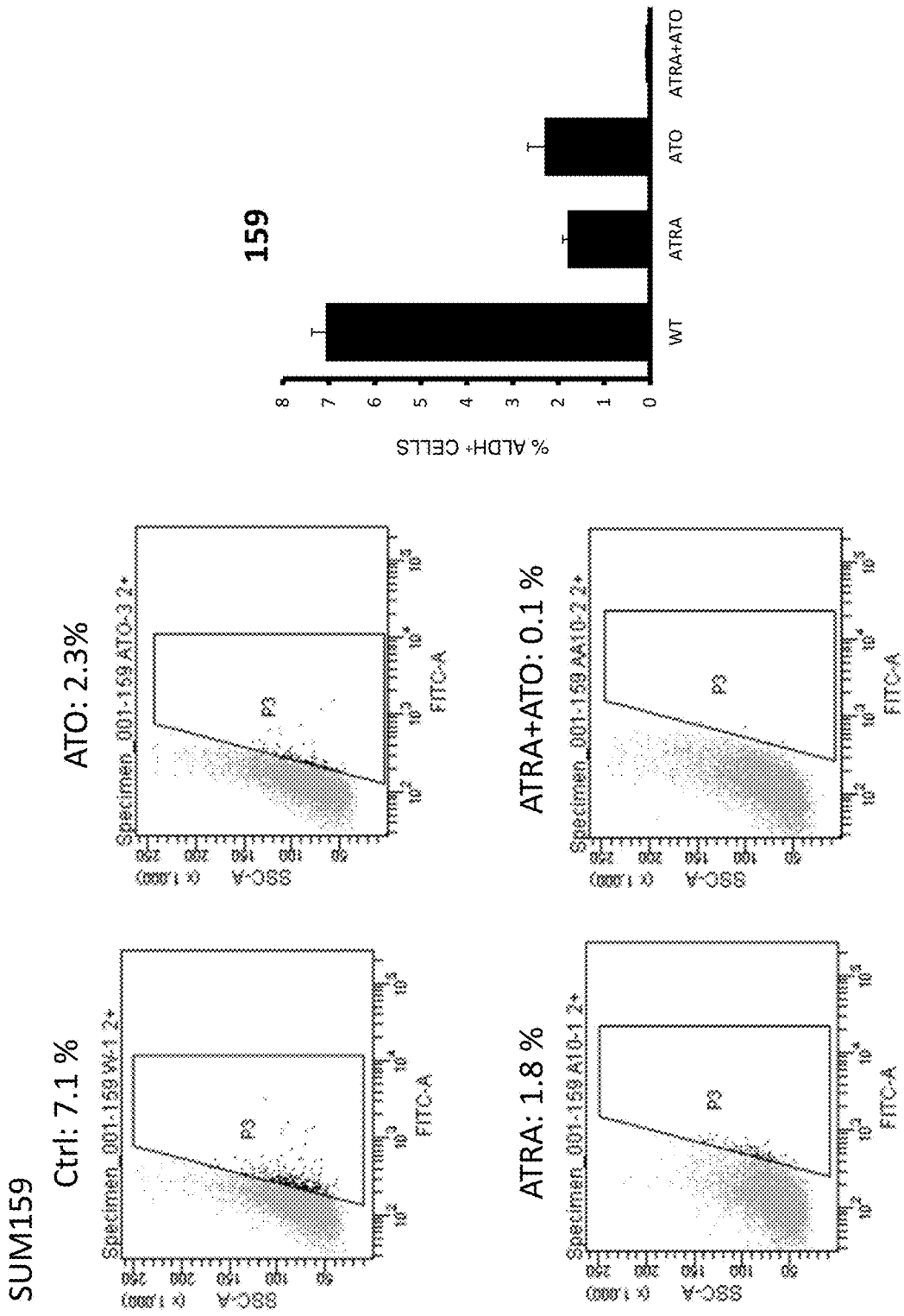
FIG. 12 is a series of plots generated by fluorescence-activated cell sorting (FACS) and a corresponding graph that depicts the quantification of aldehyde dehydrogenase-positive (ALDH+) cells following treatment with ATRA, ATO, or a combination of ATRA and ATO. ALDH is tumor marker associated with breast cancer stem cells. The fraction of ALDH+ cells is decreased in SUM159 cells treated with ATRA+ATO, as compared to those treated with either ATRA or ATO, alone.

Example 7. Combination Therapy with ATO and ATRA Synergistically Decreases the Percentage of ALDH+ Cells in Triple-Negative Breast Cancer Cell Lines Two different human triple negative breast cancer cell lines (Hs578t and SUM159) were treated with ATRA, ATO, or a combination of ATRA and ATO. Fluorescence-activated cell sorting (FACS) was used to quantify the proportion of aldehyde dehydrogenase-positive (ALDH+) cells following treatment. ALDH is tumor marker associated with breast cancer stem cells and a reduction in the proportion of ALDH+ cells may indicate inhibition, reduction, or reversing of a phenotype associated with elevated Pin1 activity (e.g., oncogenic transformation). Both ATO and ATRA, when administered alone, decreased the proportion of ALDH+ cells. The combination of ATO and ATRA synergistically decreased the proportion of ALDH+ inhibit both human triple negative breast cancer lines (FIG. 12).

Example 8. Combination Therapy with ATO and ATRA Synergistically Inhibits Tumor Growth of Human Triple Negative Breast Cancer Cells in Mice Human triple negative breast cancer MBA-MB-231 cells were xenografted into nude mice. A week after tumor growth was notable, mice were randomly grouped and treated with either ATO (2 mg/kg every other day), ATRA (5 mg 21 day slow releasing pellets), or a combination of both ATO (2 mg/kg every other day) and ATRA (5 mg 21 day slow releasing pellets). Tumor growth was measured weekly for 6 weeks and Pin1 levels were determined by immunoblotting. The combination of ATO and ATRA synergistically inhibited tumor growth of human triple negative breast cancer cells in mice (FIGS. 13A-C).

Example 9. AQP9 Overexpression Converts ATO Resistant Breast Cancer Cells to Become ATO-Sensitive The effects of ATO on cell growth were examined using 10 different human breast cancer cell lines. Sensitivity of each cell line to ATO was evaluated by treating the cells with increasing concentrations of ATO followed by assessment of cell viability (FIG. 14A).

Aquaporin 9 (AQP9) is a membrane transporter that mediates uptake of ATO and has been shown to correlate with ATO sensitivity in acute promyelocytic leukemia (APL). To demonstrate the functional significance of AQP9 expression in determining ATO sensitivity in breast cancer, AQP9 was overexpressed in three ATO-resistant human breast cancer cell lines: MCF-7, BT549, and T47D (FIG. 14B). Overexpression of AQP9 was found to potentiate the ability of ATO to inhibit cell growth in all three cell lines (FIG. 14C).

Example 10. AQP9 Overexpression Induces Pin1 Degradation in ATO-Resistant Cells

ATO-resistant breast cancer cell lines (MCF7, BT549, and T47D) overexpressing AQP9 were treated with increasing levels of ATO. It was found that AQP9 overexpression induces Pin1 degradation (FIGS. 15A-B), and that the ability of ATO to induce Pin1 degradation was tightly and positively correlated with its ability to inhibit cell growth (FIG. 14C). This further supports the notion that ATO-induced Pin1 degradation leads to cancer cell growth inhibition.

Example 11. ATRA Increases Intracellular Arsenic Concentration

Intracellular arsenic levels were measured by ICP-Masspec in breast cancer cells lines treated with either ATRA, shRNA knockdown of AQP9, or overexpression of AQP9. Treatment of an MDA-MB-231 breast cancer cell line with ATRA was found to increase intracellular arsenic concentrations relative to control (FIG. 16A). Knockdown of AQP9 expression with an AQP9 shRNA was found to decrease intracellular arsenic concentrations relative to control (FIG. 16B). Overexpression of AQP9 in an MCF-7 breast cancer cell line was found to increase intracellular arsenic concentrations relative to control (FIG. 16C).

Example 12. Combination Therapy with ATO and ATRA Inhibits Tumor Growth in Mouse Orthotopic Implantation Model Using Triple Negative Breast Cancer Cell, MDA-MB-231

Human triple negative breast cancer MBA-MB-231 cells were orthotopically implanted into nude mice. A week after tumor growth was notable, mice were randomly grouped and treated with either ATO (2 mg/kg every other day), ATRA (5 mg 21 day slow releasing pellets), or a combination of both ATO (2 mg/kg every other day) and ATRA (5 mg 21 day slow releasing pellets). Tumor growth was measured weekly for 6 weeks. Each of ATO, ATRA, and the combination of ATO and ATRA inhibited tumor growth, with the combination therapy showing the greatest reduction in tumor volume (FIGS. 17A-C).

Example 13. Combination Therapy with ATO and ATRA Inhibits Tumor Growth in Triple Negative Breast Cancer Patient Derived Xenograft (PDX) Mouse Model A PDX mouse model of triple negative breast cancer was treated with either ATO (2 mg/kg every other day), ATRA (5 mg 21 day slow releasing pellets), or a combination of both ATO (2 mg/kg every other day) and ATRA (5 mg 21 day slow releasing pellets). Treatment was initiated two weeks after implantation. Tumor growth was measured weekly for 7 weeks. Each of ATO, ATRA, and the combination of ATO and ATRA inhibited tumor growth, with the combination therapy showing the greatest reduction in tumor volume (FIGS. 18A-C). Furthermore, Pin1 levels were significantly decreased upon treatment with the ATO+ATRA combination therapy (FIG. 18D).

Furthermore, a PDX mouse model of triple negative breast cancer was treated with either ATO (2 mg/kg every other day), ATRA (5 mg 21 day slow releasing pellets), or a combination of both ATO (2 mg/kg every other day) and ATRA (5 mg 21 day slow releasing pellets). Treatment was initiated when the tumor volume reached 250 mm$^3$. Tumor growth was measured weekly for 6 weeks. Again, each of ATO, ATRA, and the combination of ATO and ATRA inhibited tumor growth, with the combination therapy showing the greatest reduction in tumor volume (FIGS. 19A-C).

Finally, a PDX mouse model of triple negative breast cancer was treated with either ATO (2 mg/kg every other day), ATRA (5 mg 21 day slow releasing pellets), or a combination of both ATO (2 mg/kg every other day) and ATRA (5 mg 21 day slow releasing pellets). Treatment was initiated when the tumor volume reached 300 mm$^3$. Tumor growth was measured weekly for 6 weeks. Again, each of ATO, ATRA, and the combination of ATO and ATRA inhibited tumor growth, with the combination therapy showing the greatest reduction in tumor volume (FIGS. 20A-C). Furthermore, Pin1 levels were decreased upon treatment with either ATO, ATRA, or the combination of ATO+ATRA (FIG. 20D).

Example 14. ATO and ATRA Synergistically Inhibit the Population and Self-Renewal of Tumor-Initiating Cells (TICs) in Triple-Negative Breast Cancer Cells (TNBCs)

As an independent but complementary approach to demonstrate that ATO has anticancer activity by targeting Pin1 oncogenic function and synergizes with ATRA, tumor initiating cells (TICs) of triple-negative breast cancer cells (TNBCs) were evaluated some these cells have been proposed to be the source of tumor initiation, growth and metastasis, but are not effectively targeted by current cancer drugs. To examine the effects of ATO and ATRA on TICs in TNBC, 231 and 159 cells were treated with ATO (1 µM), ATRA (10 µM) or their combination, followed by assaying the breast TIC-enriched CD24-CD44+ or ALDH+ population using fluorescence-activated cell sorting (FACS). While ATO and ATRA individually significantly reduced breast TIC-enriched population, their combination synergistically reduced the CD24-CD44+ or ALDH+ population (FIGS. 21A-B). To examine the effects of ATO and ATRA on self-renewal of breast TICs, different TNBC cells were treated with ATO, ATRA or their combination, followed by a serial mammosphere formation assay. Both TNBC 231 and 159 cells formed very fast growing spheres that did not decrease when propagated to M4, indicating that mammosphere-forming cells were self-renewing at a constant rate. However, after treatment with ATO or ATRA, the cells formed fewer and smaller mammospheres, displaying strongly impaired mammosphere formation efficiency at M2-3. Moreover, the co-treatment of ATO and ATRA displayed synergistic effects, almost completely inhibiting mammosphere formation efficiency at M1 (FIG. 21C).

Example 15. ATO and ATRA Synergistically Inhibit Taxol Resistance, Tumor Initiation and Tumor Growth of TICs in TNBC Breast TICs are notoriously resistant to cytotoxic chemotherapy drugs such as taxol, which is commonly used to treat TNBC. While taxol treatment kills non-TIC cancer cells, it is ineffective against TICs, leading to TIC-enriched taxol-resistant cells. Treatment with ATO and ATRA, especially in combination, not only potently inhibited the growth of taxol-resistant cells (FIG. 22A), but also effectively inhibited self-renewal of taxol-resistant breast TICs, as assayed by the serial mammosphere formation assay (FIG. 22B). Thus, the combination of ATO and ATRA inhibits the growth of taxol-resistant TNBCs. This raised the question of whether the combination of ATO and ATRA could inhibit tumor initiation and growth of breast TICs in vivo. Accordingly, the effects of ATO and ATRA combination therapy on tumor initiation of TNBCs were assayed using a limiting dilution assay in mice, a standard approach to determine tumor initiation. Importantly, ATO and ATRA co-treatment not only effectively reduced breast TIC frequency by ~90 fold (P<0.0001), but also dramatically reduced tumor growth (FIG. 22C).

OTHER EMBODIMENTS

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of inhibiting, reducing, or reversing the effect of increased Pin1 activity in one or more cells within a subject characterized as having a Pin1-associated disorder, said disorder resulting from increased Pin1 activity, said method comprising:
   administering, as treatment for said increased Pin1 activity in said one or more cells within said subject, arsenic trioxide alone, or arsenic trioxide and a retinoic acid compound;
   wherein said administration to said subject is sufficient to inhibit, reduce, or reverse the effect of increased Pin1 activity in said one or more cells within said subject,
   wherein said increased Pin1 activity is due to a somatic mutation of Pin1, wherein said somatic mutation comprises one or more of the following:
   a) Q33K;
   b) E100D;
   c) R36P;
   d) G39C;
   e) T143M; or
   f) E145K.

* * * * *